(12) United States Patent
Orme et al.

(10) Patent No.: US 12,037,334 B2
(45) Date of Patent: Jul. 16, 2024

(54) INHIBITORS OF VAP-1

(71) Applicant: ACUCELA INC., Seattle, WA (US)

(72) Inventors: Mark W. Orme, Seattle, WA (US); Edison S. Zuniga, Seattle, WA (US); Vladimir A. Kuksa, Seattle, WA (US); Russell Stuart Craft, Groningen (NL); Eduardo Moreno Saveedra, Groningen (NL); Johannes Wilhelm Georg Meissner, Groningen (NL); Jacobus Antonius Joseph den Hartog, Weesp (NL); Albert Cornelis Dros, Groningen (NL)

(73) Assignee: ACUCELA INC., Seattle, WA (US)

( * ) Notice: Subject to any disclaimer, the term of this patent is extended or adjusted under 35 U.S.C. 154(b) by 564 days.

(21) Appl. No.: 17/279,422

(22) PCT Filed: Sep. 27, 2019

(86) PCT No.: PCT/US2019/053487
§ 371 (c)(1),
(2) Date: Mar. 24, 2021

(87) PCT Pub. No.: WO2020/069335
PCT Pub. Date: Apr. 2, 2020

(65) Prior Publication Data
US 2022/0024915 A1 Jan. 27, 2022

Related U.S. Application Data

(60) Provisional application No. 62/738,933, filed on Sep. 28, 2018.

(51) Int. Cl.
C07D 471/04 (2006.01)
C07D 487/04 (2006.01)

(52) U.S. Cl.
CPC ......... C07D 471/04 (2013.01); C07D 487/04 (2013.01)

(58) Field of Classification Search
CPC .................................................. C07D 471/04
See application file for complete search history.

(56) References Cited

U.S. PATENT DOCUMENTS

| | | | |
|---|---|---|---|
| 6,139,870 A | 10/2000 | Verrecchia | |
| 6,503,497 B2 | 1/2003 | Chowhan et al. | |
| 11,649,233 B2 | 5/2023 | Wu | |
| 11,787,791 B2 * | 10/2023 | Orme | C07D 249/18 514/210.16 |
| 2002/0035251 A1 | 3/2002 | Zhang et al. | |
| 2003/0144294 A1 | 7/2003 | Zhang et al. | |
| 2007/0293548 A1 | 12/2007 | Wang et al. | |
| 2011/0269811 A1 | 11/2011 | Wang et al. | |
| 2011/0275684 A1 | 11/2011 | Nardi et al. | |
| 2012/0172392 A1 | 7/2012 | Salter-Cid et al. | |
| 2013/0143860 A1 | 6/2013 | Yoshihara et al. | |
| 2013/0324542 A1 | 12/2013 | Duan et al. | |
| 2016/0297799 A1 | 10/2016 | Brookings et al. | |
| 2017/0224663 A1 | 8/2017 | Nellore et al. | |
| 2021/0387975 A1 | 12/2021 | Orme et al. | |

FOREIGN PATENT DOCUMENTS

| | | |
|---|---|---|
| CN | 109988106 A | 7/2019 |
| WO | WO-2006015263 A2 | 2/2006 |
| WO | WO-2007120528 A2 | 10/2007 |
| WO | WO-2009066152 A2 | 5/2009 |
| WO | WO-2012124696 A1 | 9/2012 |
| WO | WO-2013163675 A1 | 11/2013 |
| WO | WO-2018073154 A1 | 4/2018 |
| WO | WO-2019101086 A1 | 5/2019 |
| WO | WO-2020069330 A2 | 4/2020 |
| WO | WO-2020069335 A2 | 4/2020 |
| WO | WO-2020069335 A3 | 7/2020 |

OTHER PUBLICATIONS

EP 19866802.2 Extended European Search Report dated Apr. 5, 2022.
PCT/US2019/053487 International Preliminary Report on Patentability dated Mar. 23, 2021.
Luo et al. Vascular adhesion protein 1 in the eye. J Ophthalmol 2013:925267 (2013).
RN2228931-88-0 Retrieved from STN Jun. 28, 2018.
Jeong et al. Biodegradable block copolymers as injectable drug-delivery systems. Nature 388:860-862 (1997).
Jeong et al. Drug release from biodegradable injectable thermosensitive hydrogel of PEG-PLGA-PEG triblock copolymers. Journal of Controlled Release 63:155-163 (2000).
Jeong et al. Thermosensitive sol-gel reversible hydrogels. Advanced Drug Delivery Reviews 54:37-51 (2002).
PCT/US2019/053487 International Search Report and Written Opinion dated Jan. 17, 2020.
Richard et al. Effects of sterilizing-grade filters on the physicochemical properties of onion-like vesicles. Int J Pharm 312(1-2):144-150 (2006).
Viegas et al. Osmotic behavior of poloxamer 407 and other nonionic surfactants in aqueous solutions. Int J Pharm 160:157-162 (1998).
Berge et al. Pharmaceutical Salts. Journal of Pharmaceutical Sciences 66(1):1-19 (Jan. 1977).
Glasoe et al. Use of glass electrodes to measure acidities in deuterium oxide. Journal of Physical Chemistry.64:188-190 (1960).
PCT/US2019/053481 International Invitation to Pay Additional Fees dated Nov. 14, 2019.
PCT/US2019/053481 International Search Report and Written Opinion dated Jan. 14, 2020.

(Continued)

Primary Examiner — Golam M Shameem
(74) Attorney, Agent, or Firm — WILSON SONSINI GOODRICH & ROSATI

(57) ABSTRACT

Provided herein are compounds and methods of use thereof for the modulation of VAP-1 activity.

18 Claims, No Drawings

(56) References Cited

OTHER PUBLICATIONS

PCT/US2019/053487 International Invitation to Pay Additional Fees dated Nov. 18, 2019.
RN:2228286-19-7 (Jun. 28, 2018).
RN:2228360-57-2 (Jun. 28, 2018).
The U. S. Food and Drug Administration has provided regulatory guidance in the publication: Guidance for Industry: Sterile Drug Products Produced by Aseptic Processing. Available at: http://www.fda.gov/cder/guidance/5882fn1.htm (Aug. 2003) (63 pgs.).
U.S. Appl. No. 17/279,382 Non-Final Office Action dated Jan. 10, 2023.

\* cited by examiner

INHIBITORS OF VAP-1

CROSS REFERENCE TO RELATED APPLICATIONS

This application is a U.S. National Stage of International Application No. PCT/US2019/053487, filed on Sep. 27, 2019, which claims the benefit of U.S. Provisional Application No. 62/738,933, filed Sep. 28, 2018; the disclosure of each of which is considered part of, and is incorporated by reference in its entirety, in the disclosure of this application.

BACKGROUND

A need exists in the medical art for compounds for the effective treatment of diseases and disorders mediated by VAP-1 protein activity, such as uveitis. Disclosed herein are solutions to this and other problems in the art.

BRIEF SUMMARY OF THE DISCLOSURE

In an aspect, provided herein is a compound having structural Formula (IV):

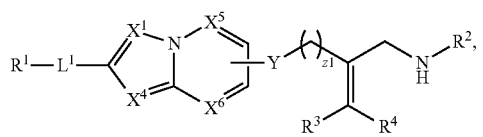

(IV)

or an alkene isomer, tautomer, or an isotopic variant thereof; or a pharmaceutically acceptable salt, solvate, hydrate, or prodrug thereof;

wherein:

$X^1$ and $X^4$ are independently =N or =CH—;

$X^5$ is =N or —$CR^5$—;

$X^6$ is =N or —$CR^6$—;

Y is a bond, —O—, —S—, —$NR^7$—, —$OCX_2$—, —$(CH_2)_{z2}W$—, —C(O)O—, or —C(O)NH—;

W is a bond, —O—, —S—, or —NH—;

z1 and z2 are independently an integer from 0 to 3;

n1, n2, n5, n6, and n7 are independently an integer from 0 to 4;

m1, m2, m5, m6, m7, v1, v2, v5, v6, and v7 are independently 1 or 2;

$L^1$ is a bond, —O—, —S—, —$NR^{1L}$—, substituted or unsubstituted alkylene, substituted or unsubstituted heteroalkylene, substituted or unsubstituted cycloalkylene, or substituted or unsubstituted heterocycloalkylene, substituted or unsubstituted arylene, or substituted or unsubstituted heteroarylene;

$R^{1L}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ is independently hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —NHC(O)$NHNR^{1B}R^{1C}$, —NHC(O)$NR^{1B}R^{1C}$, —N(O)$_{m1}$, —$NR^{1B}R^{1C}$, —C(O)$R^{1D}$, —C(C)$OR^{1D}$, —C(O)$NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl, or at least one amino acid;

$R^2$ is hydrogen, halogen, —$CX^{2.1}_3$, —$CHX^{2.1}_2$, —$CH_2X^{2.1}$, —CN, —$SO_{n2}R^{2A}$, —$SO_{v2}NR^{2B}R^{2C}$, —$NR^{2B}R^{2C}$, —C(O)$R^{2D}$, —C(O)$OR^{2D}$, —C(O)$NR^{2B}R^{2C}$, —$OR^{2A}$, —$OCX^{2.1}_3$, —$OCHX^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ and $R^4$ are independently hydrogen or —F;

$R^5$ is hydrogen, halogen, —$CX^{5.1}_3$, —$CHX^{5.1}_2$, —$CH_2X^{5.1}$, —CN, —$N_3$, —$SO_{n5}R^{5A}$, —$SO_{v5}NR^{5B}R^{5C}$, —$NHNR^{5B}R^{5C}$, —$ONR^{5B}R^{5C}$, —NHC(O)$NHNR^{5B}R^{5C}$, —NHC(O)$NR^{5B}R^{5C}$, —N(O)$_{m5}$, —$NR^{5B}R^{5C}$, —C(O)$R^{5D}$, —C(O)$OR^{5D}$, —C(O)$NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^{5.1}_3$, —$OCHX^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$CX^{6.1}_3$, —$CHX^{6.1}_2$, —$CH_2X^{6.1}$, —CN, —$N_3$, —$SO_{n6}R^{6A}$, —$SO_{v6}NR^{6B}R^{6C}$, —$NHNR^{6B}R^{6C}$, —$ONR^{6B}R^{6C}$, —NHC(O)$NHNR^{6B}R^{6C}$, —NHC(O)$NR^{6B}R^{6C}$, —N(O)$_{m6}$, —$NR^{6B}R^{6C}$, —C(O)$R^{6D}$, —C(O)—$OR^{6D}$, —C(O)$NR^{6B}R^{6C}$, —$OR^{6A}$, —$NR^{6B}SO_2R^{6A}$, —$NR^{6B}C(O)R^{6D}$, —$NR^{6B}C(O)OR^{6D}$, —$NR^{6B}OR^{6D}$, —$OCX^{6.1}_3$, —$OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, —$CX^{7.1}_3$, —$CHX^{7.1}_2$, —$CH_2X^{7.1}$, —CN, —$SO_{n7}R^{7A}$, —$SO_{v7}NR^{7B}R^{7C}$, —$NR^{7B}R^{7C}$, —C(O)$R^{7D}$, —C(O)$OR^{7D}$, —C(O)$NR^{7B}R^{7C}$, —$OR^{7A}$, —$OCX^{7.1}_3$, —$OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is hydrogen, halogen, —$CX^{12.1}_3$, —$CHX^{12.1}_2$, —$CH_2X^{12.1}$, —CN, —$SO_{n12}R^{12A}$, —$SO_{v12}NR^{12B}R^{12C}$, —$NR^{12B}R^{12C}$, —C(O)$R^{12D}$, —C(O)$OR^{12D}$, —C(O)$NR^{12B}R^{12C}$, —$OR^{12A}$, —$OCX^{12.1}_3$, —$OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$ is hydrogen, halogen, —$CF_3$, —$CCl_3$, —$CBr_3$, —$CI_3$, —COOH, —$CONH_2$, $R^{12A}$-substituted or unsubstituted alkyl, $R^{12A}$-substituted or unsubstituted heteroalkyl, $R^{12A}$-substituted or unsubstituted cycloalkyl, $R^{12A}$-substituted or unsubstituted heterocycloalkyl, $R^{12A}$-substituted or unsubstituted aryl, or $R^{12A}$-substituted or unsubstituted heteroaryl;

$R^{1B}$ is hydrogen, halogen, —$CF_3$, —$CCl_3$, —$CBr_3$, —$CI_3$, —COOH, —$CONH_2$, $R^{12B}$-substituted or unsubstituted alkyl, $R^{12B}$-substituted or unsubstituted heteroalkyl, $R^{12B}$-substituted or unsubstituted cycloalkyl, $R^{12B}$-substituted or unsubstituted heterocycloalkyl, $R^{12B}$-substituted or unsubstituted aryl, or $R^{12B}$-substituted or unsubstituted heteroaryl;

$R^{1C}$ is hydrogen, halogen, —$CF_3$, —$CCl_3$, —$CBr_3$, —$CI_3$, —COOH, —$CONH_2$, $R^{12C}$-substituted or unsubstituted alkyl, $R^{12C}$-substituted or unsubstituted heteroalkyl, $R^{12C}$-substituted or unsubstituted cycloalkyl, $R^{12C}$-substituted or unsubstituted heterocycloalkyl, $R^{12C}$-substituted or unsubstituted aryl, or $R^{12C}$-substituted or unsubstituted heteroaryl; or $R^{1B}$ and $R^{1C}$ substituents bonded to the same nitrogen atom may optionally be joined to form a substituted or unsubstituted heterocycloalkyl or substituted or unsubstituted heteroaryl;

$R^{1D}$ is hydrogen, halogen, —$CF_3$, —$CCl_3$, —$CBr_3$, —$CI_3$, —COOH, —$CONH_2$, $R^{12D}$-substituted or unsubstituted alkyl, $R^{12D}$-substituted or unsubstituted heteroalkyl, $R^{12D}$-substituted or unsubstituted cycloalkyl, $R^{12D}$-substituted or unsubstituted heterocycloalkyl, $R^{12D}$-substituted or unsubstituted aryl, or $R^{12D}$-substituted or unsubstituted heteroaryl;

$R^{2A}$, $R^{2B}$, $R^{2C}$, $R^{2D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{12A}$, $R^{12B}$, $R^{12C}$, and $R^{12D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{2B}$ and $R^{2C}$; $R^{5B}$ and $R^{5C}$; $R^{6B}$ and $R^{6C}$; $R^{7B}$ and $R^{7C}$; $R^{8B}$ and $R^{8C}$; or $R^{12B}$ and $R^{12C}$ substituents bonded to the same nitrogen atom may optionally be joined to form a substituted or unsubstituted heterocycloalkyl or substituted or unsubstituted heteroaryl; and X, $X^{1.1}$, $X^{2.1}$, $X^{5.1}$, $X^{6.1}$, $X^{7.1}$, and $X^{12.1}$ are independently —Cl, —Br, —I, or —F.

In another aspect is provided a pharmaceutical composition, comprising a compound of structural Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, and at least one pharmaceutically acceptable excipient.

In an aspect, there is provided a method of inhibiting vascular adhesion protein-1 (VAP-1) with a compound of structural Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof.

In an aspect, provided herein is a method of treating or preventing an ophthalmic disease or disorder in a subject in need thereof, comprising administering to the subject a therapeutically effective amount of a compound of structural Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof or a pharmaceutically acceptable salt thereof.

In another aspect, there is provided a method of treating or preventing uveitis a subject in need thereof, comprising administering to the subject a therapeutically effective amount of a compound of structural Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Provided herein are, for example, compounds and compositions for inhibition of vascular adhesion protein-1 (VAP-1), and pharmaceutical compositions comprising same. Also provided herein are, for example, methods of treating or preventing a disease, disorder, or condition, or a symptom thereof, mediated by modulation (e.g., inhibition) of VAP-1.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. "Cycloalkyl" is also meant to refer to bicyclic and polycyclic hydrocarbon rings such as, for example, bicyclo[2.2.1]heptane, bicyclo[2.2.2]octane, etc.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol  denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In some embodiments, the alkylarylene group has the formula:

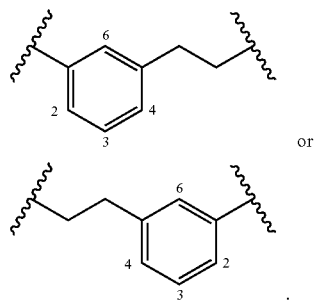

An alkylarylene moiety may be substituted (e.g., with a substituent group) on the alkylene moiety or the arylene linker (e.g., at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$ —SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl, or substituted or unsubstituted 2 to 5 membered heteroalkyl). In some embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Certain substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NRC(O)—OR", —NR'OR", in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R''', and R'''' groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties: (A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
  (i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
    (a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in the art to be too unstable to synthesize and/or isolate. The present disclosure is intended to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers that exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example, tritium ($^3$H), iodine-125 ($^{125}$I), or carbon-14 ($^{14}$C). All isotopic variations of the compounds of the present disclosure, whether radioactive or not, are encompassed within the scope of the present disclosure.

The term "isotopic variant" refers to a compound that contains an unnatural proportion of an isotope at one or more of the atoms that constitute such a compound. In certain embodiments, an "isotopic variant" of a compound contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}Cl$), bromine-79 ($^{79}Br$), bromine-81 ($^{81}Br$), and iodine-127 ($^{127}I$). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^{3}H$), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$) iodine-125 ($^{125}I$), iodine-129 ($^{129}I$), and iodine-131 ($^{131}I$). It will be understood that, in a compound as provided herein, any hydrogen can be $^{2}H$, for example, or any carbon can be $^{13}C$, for example, or any nitrogen can be $^{15}N$, for example, or any oxygen can be $^{18}O$, for example, where feasible according to the judgment of one of skill. In certain embodiments, an "isotopic variant" of a compound contains unnatural proportions of deuterium (D).

It should be noted that throughout the application alternatives are written in Markush groups, for example, each amino acid position contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as, Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with pharmaceutically acceptable acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to, sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to, those derived from inorganic acids such as hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration.

Certain compounds of the present disclosure can exist in unsolvated forms as well as solvated forms, including hydrated forms.

"Pharmaceutically acceptable excipient" and "pharmaceutically acceptable carrier" refer to a substance that aids the administration of a compound to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as, Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

A "VAP-1 inhibitor" refers to a compound (e.g., compounds described herein) that reduces the activity of VAP-1 when compared to a control, such as absence of the compound or a compound with known inactivity.

Vascular adhesion protein-1 (VAP-1) is a member of the family of copper-containing amine oxidases/semicarbazide-sensitive amine oxidase (AOC/SSAO), found in humans as a membrane-bound form and a soluble form. The membrane-bound form of VAP-1 is mainly expressed in endothelial cells, smooth muscle cells, and adipocytes, whereas the soluble VAP-1 is released into plasma mainly from vascular endothelial cells. VAP-1 has a distal adhesion domain and an enzymatically active amine oxidase site outside of the membrane. As an adhesion molecule, VAP-1 is involved in leukocyte rolling, adhesion and transmigration, which are important in leukocyte extravasation to sites of inflammation. VAP-1 also acts as an amine oxidase. It possesses topaquinone (TPQ) in the active site as a cofactor, and catalyzes the conversion of primary amines, for example, methylamine and aminoacetone, into the corresponding aldehydes, for example, formaldehyde and methylglyoxal, while releasing ammonia and hydrogen peroxide.

$$RCH_2NH_2 + O_2 + H_2O \rightarrow RCHO + H_2O_2 + NH_3$$

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme (e.g., VAP-1).

As defined herein, the terms "activation," "activate," and/or "activating" and the like in reference to a protein refer to conversion of a protein into a biologically active derivative from an initial inactive or deactivated state. The terms reference activation, or activating, sensitizing, or up-regulating signal transduction or enzymatic activity or the amount of a protein decreased in a disease.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist. In some embodiments, an agonist is a molecule that interacts with a target to cause or promote an increase in the activation of the target. In some embodiments, activators are molecules that increase, activate, facilitate, enhance activation, sensitize, or up-regulate, e.g., a gene, protein, ligand, receptor, or cell.

As defined herein, the terms "inhibition," "inhibit," "inhibiting," and the like, in reference to a protein-inhibitor interaction mean negatively affecting (e.g., decreasing) the activity or function of the protein relative to the activity or function of the protein in the absence of the inhibitor. In some embodiments, inhibition means negatively affecting (e.g., decreasing) the concentration or levels of the protein relative to the concentration or level of the protein in the absence of the inhibitor. In some embodiments, inhibition refers to reduction of a disease or symptoms of disease. In some embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In some embodiments, inhibition refers to a reduction of activity of a target protein resulting from a direct interaction (e.g., an inhibitor binds to the target protein). In some embodiments, inhibition refers to a reduction of activity of a target protein from an indirect interaction (e.g., an inhibitor binds to a protein that activates the target protein, thereby preventing target protein activation).

The terms "inhibitor," "repressor," "antagonist," or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist. An antagonist prevents, reduces, inhibits, or neutralizes the activity of an agonist, and an antagonist can also prevent, inhibit, or reduce constitutive activity of a target, e.g., a target receptor, even where there is no identified agonist. In some embodiments, inhibitors are molecules that decrease, block, prevent, delay activation, inactivate, desensitize, or down-regulate, e.g., a gene, protein, ligand, receptor, or cell. An inhibitor may also be defined as a molecule that reduces, blocks, or inactivates a constitutive activity. An "antagonist" is a molecule that opposes the action(s) of an agonist.

The terms "disease" or "condition" refer to a state of being or health status of a patient or subject capable of being treated with the compounds or methods provided herein. The disease may be an autoimmune disease. The disease may be an inflammatory disease.

As used herein, the term "inflammatory disease" refers to a disease or condition characterized by aberrant inflammation (e.g., an increased level of inflammation compared to a control such as a healthy person not suffering from a disease). Examples of inflammatory diseases include autoimmune diseases and uveitis (e.g., anterior uveitis including iridocyclitis and iritis, intermediate uveitis or pars planitis, posterior uveitis or chorioretinitis, and pan-uveitis). Such conditions are frequently inextricably intertwined with other diseases, disorders, and conditions. A non-limiting list of inflammatory-related diseases, disorders, and conditions include, Behcet's disease, Crohn's disease, Fuchs heterochromic iridocyclitis, Granulomatosis with polyangiitis, HLA-B27 related uveitis, arthritis (e.g., Juvenile idiopathic arthritis), Sarcoidosis, Spondyloarthritis, Sympathetic ophthalmia, Tubulointerstitial nephritis, uveitis syndrome, ankylosing spondylitis, chronic granulomatous disease, enthesitis, inflammatory bowel disease, Kawasaki's disease, multiple sclerosis, polyarteritis nodosa, psoriatic arthritis, reactive arthritis, sarcoidosis, systemic lupus erythematosus, Vogt-Koyanagi-Harada disease, Whipple's disease, white dot syndromes, and Masquerade syndromes. Uveitis can also be associated with infectious disease such as brucellosis, herpes viruses (herpes simplex), varicella zoster, leptospirosis, Lyme disease, presumed ocular histoplasmosis syndrome, syphilis, toxocariasis, toxoplasmic chorioretinitis, tuberculosis, and Zika fever.

White dot syndromes include, but are not limited to, acute posterior multifocal placoid pigment epitheliopathy, birdshot chorioretinopathy, multifocal choroiditis and panuveitis, multiple evanescent white dot syndrome, punctate inner choroiditis, serpiginous choroiditis, and acute zonal occult outer retinopathy.

Masquerade syndromes are divided into non-neoplastic and neoplastic conditions. Non-limiting examples of non-neoplastic masquerade syndromes include retinitis pigmentosa, intraocular foreign body, juvenile xanthogranuloma, and retinal detachment. Non-limiting examples of neoplastic masquerade syndromes include retinoblastoma, lymphoma, malignant melanoma, leukemia, and reticulum cell sarcoma.

The terms "treating" or "treatment" refer to any indicia of success in the therapy or amelioration of an injury, disease, pathology, or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In some embodiments, treating is preventing. In some embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of disease symptoms in a patient. As indicated above, the prevention may be complete (no detectable symptoms) or partial, such that fewer symptoms are observed than would likely occur absent treatment. In some embodiments, prevent refers to slowing the progression of the disease, disorder or condition or inhibiting progression thereof to a harmful or otherwise undesired state.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of a VAP-1 inhibitor (or, e.g., a metabolite thereof) at a particular time post-administration may be indicative of whether a therapeutically effective amount has been administered.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration or topical administration. The compositions of the present disclosure can be delivered by a topical route, formulated as solutions, suspensions, emulsions, gels, and ointments. Oral preparations include tablets, pills, and capsules, etc., suitable for ingestion by the patient.

For any compound described herein, the therapeutically effective amount can be initially determined from cell culture assays. Target concentrations will be those concentrations of active compound(s) that are capable of achieving the methods described herein, as measured using the methods described herein or known in the art.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include, but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "associated" or "associated with" in the context of a substance or substance activity or function associated with a disease (e.g., a VAP-1 associated disease (e.g., uveitis) means that the disease (e.g., uveitis) is caused by (in whole or in part), or a symptom of the disease is caused by (in whole or in part) the substance or substance activity or function. For example, a uveitis associated with VAP-1 activity or function may be a uveitis that results (entirely or partially) from aberrant VAP-1 function (e.g., enzyme activity, protein-protein interaction, signaling pathway) or a uveitis wherein a particular symptom of the disease is caused (entirely or partially) by aberrant VAP-1 activity or function. As used herein, what is described as being associated with a disease, if a causative agent, could be a target for treatment of the disease. For example, a uveitis associated with VAP-1 activity or function or a VAP-1 associated disease (e.g., uveitis), may be treated with a compound described herein (e.g., VAP-1 modulator or VAP-1 inhibitor), in the instance where increased VAP-1 activity or function (e.g. signaling pathway activity) causes the disease (e.g., uveitis). For example, an inflammatory disease associated with VAP-1 activity or function or a VAP-1 associated inflammatory disease, may be treated with a VAP-1 modulator or VAP-1 inhibitor, in the instance where increased VAP-1 activity or function (e.g., signaling pathway activity) causes the disease.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g., by administering a compound or using a method as described herein), results in reduction of the disease or one or more disease symptoms.

As used herein, the terms "VAP-1 inhibitor," "VAP-1 antagonist," "Vascular adhesion protein-1 inhibitor," "Vascular adhesion protein-1 antagonist," and all other related art-accepted terms, many of which are set forth below, refer to a compound capable of modulating, either directly or indirectly, the VAP-1 receptor in an in vitro assay, an in vivo model, and/or other means indicative of therapeutic efficacy. The terms also refer to a compound that exhibits at least some therapeutic benefit in a human subject.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like.

"Substantially pure" indicates that a component makes up greater than about 50% of the total content of the composition, and typically greater than about 60% of the total composition content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition (percentage in a weight per weight basis).

The term "uveitis" is used because the diseases often affect a part of the eye called the uvea. Nevertheless, uveitis is not limited to the uvea. These diseases also affect the lens, retina, optic nerve, and vitreous, producing reduced vision or blindness. Common symptoms of uveitis include decreased vision, pain, light sensitivity, and increased floaters. Uveitis is a general term describing a group of inflammatory diseases that produces swelling and destroys eye tissues.

II. Compounds

In some embodiments, a compound as described herein may include multiple instances of a substituent (e.g., $R^3$, $R^5$, or $R^6$ and/or other variables). In such embodiments, each variable may optional be different and be appropriately labeled to distinguish each group for greater clarity. For example, where each $R^3$, $R^5$, $R^6$ is different, they may be referred to, for example, as $R^{3.1}$, $R^{3.2}$, $R^{3.3}$, $R^{3.4}$, $R^{3.5}$, $R^{5.1}$, $R^{5.2}$, $R^{5.3}$, $R^{5.4}$, or $R^{6.1}$, $R^{6.2}$, $R^{6.3}$, $R^{6.4}$, $R^{6.5}$, $R^{6.6}$, $R^{6.7}$, $R^{6.8}$, $R^{6.9}$, or $R^{61.0}$, respectively, wherein the definition of $R^3$ is assumed by (independently assigned to) $R^{3.4}$, $R^{3.2}$, $R^{3.3}$, $R^{3.4}$, $R^{3.5}$; $R^5$ is assumed by (independently assigned to) $R^{5.1}$, $R^{5.2}$, $R^{5.3}$, $R^{5.4}$; or $R^6$ is assumed by (independently assigned to) $R^{6.1}$, $R^{6.2}$, $R^{6.3}$, $R^{6.4}$, $R^{6.5}$, $R^{6.6}$, $R^{6.7}$, $R^{6.8}$, $R^{6.9}$, or $R^{6.10}$. The variables used within a definition of $R^3$, $R^5$, or $R^6$, and/or other variables that appear at multiple instances and are different may similarly be appropriately labeled to distinguish each group for greater clarity.

In some embodiments, unless otherwise indicated, a compound described herein is a racemic mixture of all stereoisomers. In some embodiments, unless otherwise indicated, a compound described herein is a racemic mixture of all enantiomers. In some embodiments, unless otherwise indicated, a compound described herein is a racemic mixture of two opposite stereoisomers. In some embodiments, unless otherwise indicated, a compound described herein is a racemic mixture of two opposite enantiomers. In some embodiments, unless otherwise indicated, a compound described herein is a single stereoisomer. In some embodiments, unless otherwise indicated, a compound described herein is a single enantiomer. In some embodiments, the compound is a compound described herein (e.g., in an aspect, embodiment, example, figure, table, scheme, or claim).

In an aspect, provided herein is a compound having structural Formula (IV):

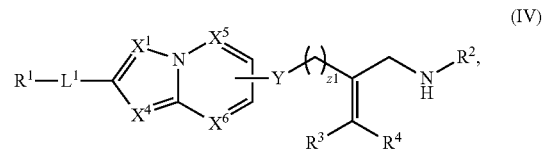

(IV)

or an alkene isomer, tautomer, or an isotopic variant thereof; or a pharmaceutically acceptable salt, solvate, hydrate, or prodrug thereof;

wherein:

$X^1$ and $X^4$ are independently =N— or =CH—;

$X^5$ is =N— or —$CR^5$—;

$X^6$ is =N— or —$CR^6$—;

Y is a bond, —O—, —S—, —$NR^7$—, —$OCX_2$—, —$(CH_2)_{z2}W$—, —C(O)O—, or —C(O)NH—;

W is a bond, —O—, —S—, or —NH—;

z1 and z2 are independently an integer from 0 to 3;

n1, n2, n5, n6, and n7 are independently an integer from 0 to 4;

m1, m2, m5, m6, m7, v1, v2, v5, v6, and v7 are independently 1 or 2;

$L^1$ is a bond, —O—, —S—, —$NR^{1L}$—, substituted or unsubstituted alkylene, substituted or unsubstituted heteroalkylene, substituted or unsubstituted cycloalkylene, or substituted or unsubstituted heterocycloalkylene, substituted or unsubstituted arylene, or substituted or unsubstituted heteroarylene;

$R^{1L}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ is independently hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —$NHC(O)NR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl, or at least one amino acid;

$R^2$ is hydrogen, halogen, —$CX^{2.1}_3$, —$CHX^{2.1}_2$, —$CH_2X^{2.1}$, —CN, —$SO_{n2}R^{2A}$, —$SO_{v2}NR^{2B}R^{2C}$, —$NR^{2B}R^{2C}$, —$C(O)R^{2D}$, —$C(O)OR^{2D}$, —$C(O)NR^{2B}R^{2C}$, —$OR^{2A}$, —$OCX^{2.1}_3$, —$OCHX^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ and $R^4$ are independently hydrogen or —F;

$R^5$ is hydrogen, halogen, —$CX^{5.1}_3$, —$CHX^{5.1}_2$, —$CH_2X^{5.1}$, —CN, —$N_3$, —$SO_{n5}R^{5A}$, —$SO_{v5}NR^{5B}R^{5C}$, —$NHNR^{5B}R^{5C}$, —$ONR^{5B}R^{5C}$, —$NHC(O)NHNR^{5B}R^{5C}$, —$NHC(O)NR^{5B}R^{5C}$, —$N(O)_{m5}$, —$NR^{5B}R^{5C}$, —$C(O)R^{5D}$, —$C(O)OR^{5D}$, —$C(O)NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^{5.1}_3$, —$OCHX^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$CX^{6.1}_3$, —$CHX^{6.1}_2$, —$CH_2X^{6.1}$, —CN, —$N_3$, —$SO_{m6}R^{6A}$, —$SO_{v6}NR^{6B}R^{6C}$, —$NHNR^{6B}R^{6C}$, —$ONR^{6B}R^{6C}$, —$NHC(O)NHNR^{6B}R^{6C}$, —$NHC(O)NR^{6B}R^{6C}$, —$N(O)_{m6}$, —$NR^{6B}R^{6C}$, —$C(O)R^{6D}$, —$C(O)OR^{6D}$, —$C(O)NR^{6B}R^{6C}$, —$OR^{6A}$, —$NR^{6B}SO_2R^{6A}$, —$NR^{6B}C(O)R^{6D}$, —$NR^{6B}C(O)OR^{6D}$, —$NR^{6B}OR^{6D}$, —$OCX^{6.1}_3$, —$OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, —$CX^{7.1}_3$, —$CHX^{7.1}_2$, —$CH_2X^{7.1}$, —CN, —$SO_{n7}R^{7A}$, —$SO_{v7}NR^{7B}R^{7C}$, —$NR^{7B}R^{7C}$, —$C(O)R^{7D}$, —$C(O)OR^{7D}$, —$C(O)NR^{7B}R^{7C}$, —$OR^{7A}$, —$OCX^{7.1}_3$, —$OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is hydrogen, halogen, —$CX^{12.1}_3$, —$CHX^{12.1}_2$, —$CH_2X^{12.1}$, —CN, —$SO_{n12}R^{12A}$, —$SO_{v12}NR^{12B}R^{12C}$, —$NR^{12B}R^{12C}$, —$C(O)R^{12D}$, —$C(O)OR^{12D}$, —$C(O)_{NR}^{12B}R^{12C}$, —$OR^{12A}$, —$OCX^{12.1}_3$, —$OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$ is hydrogen, halogen, —$CF_3$, —$CCl_3$, —$CBr_3$, —$CI_3$, —COOH, —$CONH_2$, $R^{12A}$-substituted or unsubstituted alkyl, $R^{12A}$-substituted or unsubstituted heteroalkyl, $R^{12A}$-substituted or unsubstituted cycloalkyl, $R^{12A}$-substituted or unsubstituted heterocycloalkyl, $R^{12A}$-substituted or unsubstituted aryl, or $R^{12A}$-substituted or unsubstituted heteroaryl;

$R^{1B}$ is hydrogen, halogen, —$CF_3$, —$CCl_3$, —$CBr_3$, —$CI_3$, —COOH, —$CONH_2$, $R^{12B}$-substituted or unsubstituted alkyl, $R^{12B}$-substituted or unsubstituted heteroalkyl, $R^{12B}$-substituted or unsubstituted cycloalkyl, $R^{12B}$-substituted or unsubstituted heterocycloalkyl, $R^{12B}$-substituted or unsubstituted aryl, or $R^{12B}$-substituted or unsubstituted heteroaryl;

$R^{1C}$ is hydrogen, halogen, —$CF_3$, —$CCl_3$, —$CBr_3$, —$CI_3$, —COOH, —$CONH_2$, $R^{12C}$-substituted or unsubstituted alkyl, $R^{12C}$-substituted or unsubstituted heteroalkyl, $R^{12C}$-substituted or unsubstituted cycloalkyl, $R^{12C}$-substituted or unsubstituted heterocycloalkyl, $R^{12C}$-substituted or unsubstituted aryl, or $R^{12C}$-substituted or unsubstituted heteroaryl; or $R^{1B}$ and $R^{1C}$ substituents bonded to the same nitrogen atom may optionally be joined to form a substituted or unsubstituted heterocycloalkyl or substituted or unsubstituted heteroaryl;

$R^{1D}$ is hydrogen, halogen, —$CF_3$, —$CCl_3$, —$CBr_3$, —$CI_3$, —COOH, —$CONH_2$, $R^{12D}$-substituted or unsubstituted alkyl, $R^{12D}$-substituted or unsubstituted heteroalkyl, $R^{12D}$-substituted or unsubstituted cycloalkyl, $R^{12D}$-substituted or unsubstituted heterocycloalkyl, $R^{12D}$-substituted or unsubstituted aryl, or $R^{12D}$-substituted or unsubstituted heteroaryl;

$R^{2A}$, $R^{2B}$, $R^{2C}$, $R^{2D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{12A}$, $R^{12B}$, $R^{12C}$, and $R^{12D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{2B}$ and $R^{2C}$; $R^{5B}$ and $R^{5C}$; $R^{6B}$ and $R^{6C}$; $R^{7B}$ and $R^{7C}$; $R^{8B}$ and $R^{8C}$; or $R^{12B}$ and $R^{12C}$ substituents bonded to the same nitrogen atom may optionally be joined to form a substituted or unsubstituted heterocycloalkyl or substituted or unsubstituted heteroaryl; and X, $X^{1.1}$, $X^{2.1}$, $X^{5.1}$, $X^{6.1}$, $X^{7.1}$, and $X^{12.1}$ are independently —Cl, —Br, —I, or —F.

In some embodiments, the compound of Formula (IV) has structural Formula (IV-A):

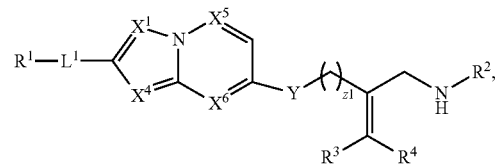

(IV-A)

or an alkene isomer, tautomer, or an isotopic variant thereof; or a pharmaceutically acceptable salt, solvate, hydrate, or prodrug thereof.

In some embodiments, the compound of Formula (IV) has structural Formula (IV-B):

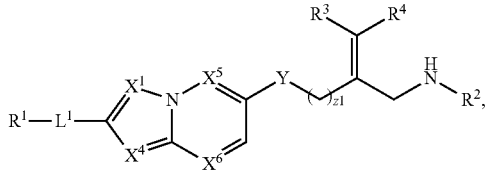

(IV-B)

or an alkene isomer, tautomer, or an isotopic variant thereof; or a pharmaceutically acceptable salt, solvate, hydrate, or prodrug thereof.

In some embodiments, the compound of Formula (IV) has structural Formula (V-A):

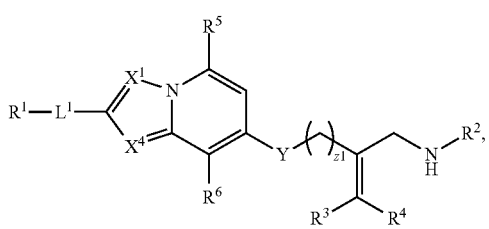

(V-A)

or an alkene isomer, tautomer, or an isotopic variant thereof; or a pharmaceutically acceptable salt, solvate, hydrate, or prodrug thereof.

In some embodiments, the compound of Formula (IV) has structural Formula (V-B):

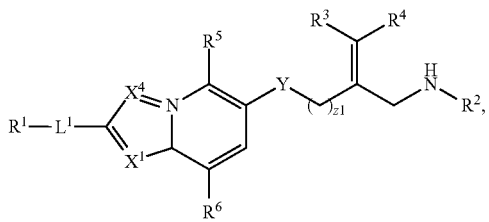

(V-B)

or an alkene isomer, tautomer, or an isotopic variant thereof, or a pharmaceutically acceptable salt, solvate, hydrate, or prodrug thereof.

In some embodiments, the compound of Formula (IV) has structural Formula (VI-A):

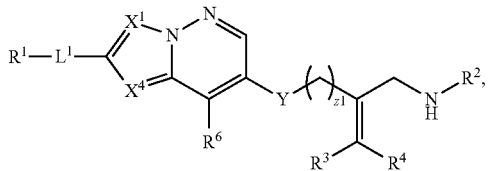

(VI-A)

or an alkene isomer, tautomer, or an isotopic variant thereof, or a pharmaceutically acceptable salt, solvate, hydrate, or prodrug thereof.

In some embodiments, the compound of Formula (IV) has structural Formula (VI-B):

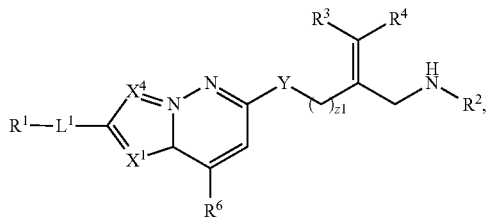

(VI-B)

or an alkene isomer, tautomer, or an isotopic variant thereof; or a pharmaceutically acceptable salt, solvate, hydrate, or prodrug thereof.

In some embodiments, the compound of Formula (IV) has structural Formula (VII-A):

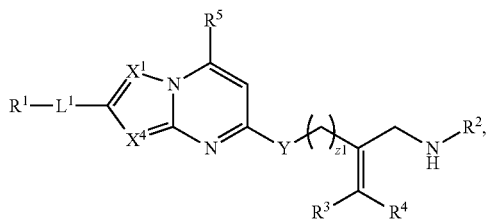

(VII-A)

or an alkene isomer, tautomer, or an isotopic variant thereof; or a pharmaceutically acceptable salt, solvate, hydrate, or prodrug thereof.

In some embodiments, the compound of Formula (IV) has structural Formula (VII-B):

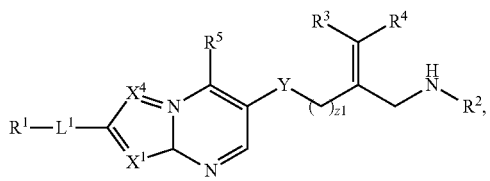

(VII-B)

or an alkene isomer, tautomer, or an isotopic variant thereof; or a pharmaceutically acceptable salt, solvate, hydrate, or prodrug thereof.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $X^1$ is =N—.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $X^1$=CH—.

In some embodiments of the compound of Formula (IV), (IV-A), (IV-B), (V-A), (V-B), (VI-A), (VI-B), (VII-A), and/ or (VII-B), or an alkene isomer, tautomer, or an isotopic variant thereof; or a pharmaceutically acceptable salt, solvate, hydrate, or prodrug thereof, $X^4$ is =N—.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $X^4$ is =CH—.

In some embodiments of the compound of Formula (IV) and/or (V-A),
a partial structure represented by

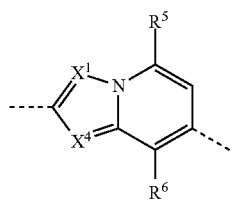

is

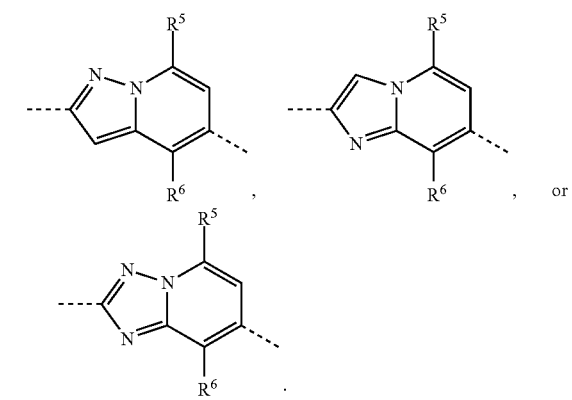

In some embodiments of the compound of Formula (IV) and/or (V-B),
a partial structure represented by

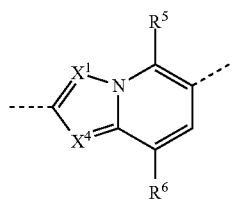

is

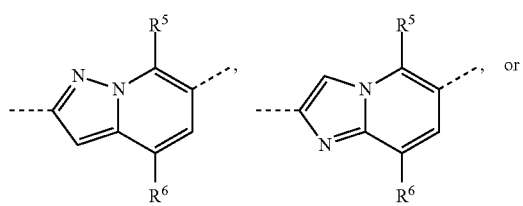

In some embodiments of the compound of Formula (IV) and/or (VI-A),
a partial structure represented by

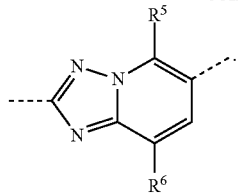

is

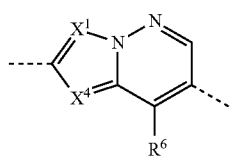

In some embodiments of the compound of Formula (IV) and/or (VII-A),
a partial structure represented by

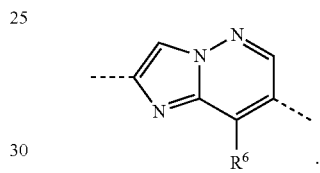

is

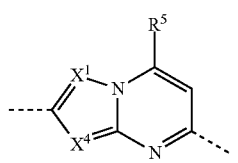

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, Y is a bond.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, Y is —$OCF_2$—.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, Y is —O—.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, Y is —S—.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, Y is —NH—.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, Y is —CH$_2$O—.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, Y is —C(O)NH—.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, z1 is 0. In some embodiments, of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, z1 is 1. In some embodiments, of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, z1 is 2.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $R^5$ and $R^6$ are independently hydrogen, halogen, or unsubstituted alkyl.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $R^5$ and $R^6$ are independently hydrogen, —F, —Br, or —CH$_3$.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $R^3$ is —F.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $R^3$ is hydrogen.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $R^4$ is —F.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $R^4$ is hydrogen.

In some embodiments, the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, is a mixture of compounds having:
$R^3$ is —F and $R^4$ is hydrogen; and
$R^3$ is hydrogen and $R^4$ is —F.

In some embodiments, the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, comprises a mixture of (E)- and (Z)-alkene isomers.

In some embodiments, of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, the ratio of the (E)-isomer, or tautomer, or an isotopic variant thereof; or a pharmaceutically acceptable salt, solvate, hydrate, or prodrug thereof, to the (Z)-isomer, or tautomer, or an isotopic variant thereof; or a pharmaceutically acceptable salt, solvate, hydrate, or prodrug thereof, is from about 10:1 to about 1:10.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, the ratio of the (E)-isomer, or tautomer, or an isotopic variant thereof; or a pharmaceutically acceptable salt, solvate, hydrate, or prodrug thereof, to the (Z)-isomer, or tautomer, or an isotopic variant thereof; or a pharmaceutically acceptable salt, solvate, hydrate, or prodrug thereof, is from about 5:1 to about 1:5.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, the ratio of the (E)-isomer, or tautomer, or an isotopic variant thereof; or a pharmaceutically acceptable salt, solvate, hydrate, or prodrug thereof, to the (Z)-isomer, or tautomer, or an isotopic variant thereof; or a pharmaceutically acceptable salt, solvate, hydrate, or prodrug thereof, is about 1:1.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $R^2$ is hydrogen.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $L^1$ is a bond, —NR$^{1L}$—, substituted or unsubstituted alkylene, substituted or unsubstituted heteroalkylene, substituted or unsubstituted cycloalkylene, or substituted or unsubstituted heterocycloalkylene.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $L^1$ is a bond.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $L^1$ is —$NR^{1L}$—.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $R^{1L}$ is hydrogen or substituted or unsubstituted alkyl.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $L^1$ is substituted or unsubstituted alkylene, substituted or unsubstituted heteroalkylene, substituted or unsubstituted cycloalkylene, or substituted or unsubstituted heterocycloalkylene.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $R^1$ is —$NR^{1B}R^{1C}$, —$C(O)NR^{1B}R^{1C}$, —$OR^{1A}$, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $R^1$ is $R^{12}$-substituted or unsubstituted $C_1$-$C_6$ alkyl.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $R^1$ is —$(CH_2)_3CH_3$.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $R^{12}$-substituted or unsubstituted cycloalkyl.

In some embodiments of the compound of Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, $R^{12}$ is substituted or unsubstituted alkyl, or substituted or unsubstituted aryl.

In an aspect, provided herein is a compound, wherein the compound is:

or an alkene isomer, tautomer, or an isotopic variant thereof; or a pharmaceutically acceptable salt, solvate, hydrate, or prodrug thereof.

In certain embodiments, $L^1$ is a bond, —O—, —S—, —$NR^{1L}$—, substituted or unsubstituted alkylene, substituted or unsubstituted heteroalkylene, substituted or unsubstituted cycloalkylene, or substituted or unsubstituted heterocycloalkylene, substituted or unsubstituted arylene, or substituted or unsubstituted heteroarylene.

In certain embodiments, $L^1$ is $R^9$-substituted or unsubstituted alkylene (e.g., $C_1$-$C_8$ alkylene, $C_1$-$C_6$ alkylene, or $C_1$-$C_4$ alkylene). In certain embodiments, $L^1$ is $R^9$-substituted alkylene (e.g., $C_1$-$C_8$ alkylene, $C_1$-$C_6$ alkylene, or $C_1$-$C_4$ alkylene). In certain embodiments, $L^1$ is an unsubstituted alkylene (e.g., $C_1$-$C_8$ alkylene, $C_1$-$C_6$ alkylene, or $C_1$-$C_4$ alkylene).

In certain embodiments, $L^1$ is $R^9$-substituted or unsubstituted heteroalkylene (e.g., 2 to 8 membered heteroalkylene, 2 to 6 membered heteroalkylene, or 2 to 4 membered heteroalkylene). In certain embodiments, $L^1$ is $R^9$-substituted heteroalkylene (e.g., 2 to 8 membered heteroalkylene, 2 to 6 membered heteroalkylene, or 2 to 4 membered heteroalkylene). In certain embodiments, $L^1$ is an unsubstituted heteroalkylene (e.g., 2 to 8 membered heteroalkylene, 2 to 6 membered heteroalkylene, or 2 to 4 membered heteroalkylene).

In certain embodiments, $L^1$ is $R^9$-substituted or unsubstituted cycloalkylene (e.g., $C_3$-$C_8$ cycloalkylene, $C_3$-$C_6$ cycloalkylene, or $C_5$-$C_6$ cycloalkylene). In certain embodiments, $L^1$ is $R^9$-substituted cycloalkylene (e.g., $C_3$-$C_8$ cycloalkylene, $C_3$-$C_6$ cycloalkylene, or $C_5$-$C_6$ cycloalkylene). In certain embodiments, $L^1$ is an unsubstituted cycloalkylene (e.g., $C_3$-$C_8$ cycloalkylene, $C_3$-$C_6$ cycloalkylene, or $C_5$-$C_6$ cycloalkylene).

In certain embodiments, $L^1$ is $R^9$-substituted or unsubstituted heterocycloalkylene (e.g., 3 to 8 membered heterocycloalkylene, 3 to 6 membered heterocycloalkylene, or 5 to 6 membered heterocycloalkylene). In certain embodiments, $L^1$ is $R^9$-substituted heterocycloalkylene (e.g., 3 to 8 membered heterocycloalkylene, 3 to 6 membered heterocycloalkylene, or 5 to 6 membered heterocycloalkylene). In certain embodiments, $L^1$ is an unsubstituted heterocycloalkylene (e.g., 3 to 8 membered heterocycloalkylene, 3 to 6 membered heterocycloalkylene, or 5 to 6 membered heterocycloalkylene).

In certain embodiments, $L^1$ is $R^9$-substituted or unsubstituted arylene (e.g., $C_6$-$C_{10}$ arylene, $C_{10}$ arylene, or phenylene). In certain embodiments, $L^1$ is $R^9$-substituted arylene (e.g., $C_6$-$C_{10}$ arylene, $C_{10}$ arylene, or phenylene). In certain embodiments, $L^1$ is an unsubstituted arylene (e.g., $C_6$-$C_{10}$ arylene, $C_{10}$ arylene, or phenylene).

In certain embodiments, $L^1$ is $R^9$-substituted or unsubstituted heteroarylene (e.g., 5 to 10 membered heteroarylene, 5 to 9 membered heteroarylene, or 5 to 6 membered heteroarylene). In certain embodiments, $L^1$ is $R^9$-substituted heteroarylene (e.g., 5 to 10 membered heteroarylene, 5 to 9 membered heteroarylene, or 5 to 6 membered heteroarylene). In certain embodiments, $L^1$ is an unsubstituted heteroarylene (e.g., 5 to 10 membered heteroarylene, 5 to 9 membered heteroarylene, or 5 to 6 membered heteroarylene).

In certain embodiments, $R^1$ is independently hydrogen, halogen, $-CX^{1.1}{}_3$, $-CHX^{1.1}{}_2$, $-CH_2X^{1.1}$, $-CN$, $-SO_{n1}R^{1A}$, $SO_{v1}NR^{1B}R^{1C}$, $-NR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^{1.1}{}_3$, $-OCHX^{1.1}{}_2$, $R^{12}$-substituted or unsubstituted alkyl (e.g., $C_1$-$C_8$ alkyl, $C_1$-$C_6$ alkyl, or $C_1$-$C_4$ alkyl), $R^{12}$-substituted or unsubstituted heteroalkyl (e.g., 2 to 8 membered heteroalkyl, 2 to 6 membered heteroalkyl, or 2 to 4 membered heteroalkyl), $R^{12}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{12}$-substituted or unsubstituted heterocycloalkyl (e.g., 3 to 8 membered heterocycloalkyl, 3 to 6 membered heterocycloalkyl, or 5 to 6 membered heterocycloalkyl), $R^{12}$-substituted or unsubstituted aryl (e.g., $C_6$-$C_{10}$ aryl, $C_{10}$ aryl, or phenyl), or $R^{12}$-substituted or unsubstituted heteroaryl (e.g., 5 to 10 membered heteroaryl, 5 to 9 membered heteroaryl, or 5 to 6 membered heteroaryl).

In certain embodiments, $R^1$ is $R^{12}$-substituted or unsubstituted alkyl (e.g., $C_1$-$C_8$ alkyl, $C_1$-$C_6$ alkyl, or $C_1$-$C_4$ alkyl). In certain embodiments, $R^1$ is $R^{12}$-substituted alkyl (e.g., $C_1$-$C_8$ alkyl, $C_1$-$C_6$ alkyl, or $C_1$-$C_4$ alkyl). In certain embodiments, $R^1$ is an unsubstituted alkyl (e.g., $C_1$-$C_8$ alkyl, $C_1$-$C_6$ alkyl, or $C_1$-$C_4$ alkyl).

In certain embodiments, $R^1$ is $R^{12}$-substituted or unsubstituted heteroalkyl (e.g., 2 to 8 membered heteroalkyl, 2 to 6 membered heteroalkyl, or 2 to 4 membered heteroalkyl). In certain embodiments, $R^1$ is $R^{12}$-substituted heteroalkyl (e.g., 2 to 8 membered heteroalkyl, 2 to 6 membered heteroalkyl, or 2 to 4 membered heteroalkyl). In certain embodiments, $R^1$ is an unsubstituted heteroalkyl (e.g., 2 to 8 membered heteroalkyl, 2 to 6 membered heteroalkyl, or 2 to 4 membered heteroalkyl).

In certain embodiments, $R^1$ is $R^{12}$-substituted or unsubstituted cycloalkyl (e.g., $C_3$-$C_8$ cycloalkyl, $C_3$-$C_6$ cycloalkyl, or $C_5$-$C_6$ cycloalkyl). In certain embodiments, $R^1$ is $R^{12}$-substituted cycloalkyl (e.g., $C_3$-$C_8$ cycloalkyl, $C_3$-$C_6$ cycloalkyl, or $C_5$-$C_6$ cycloalkyl). In certain embodiments, $R^1$ is an unsubstituted cycloalkyl (e.g., $C_3$-$C_8$ cycloalkyl, $C_3$-$C_6$ cycloalkyl, or $C_5$-$C_6$ cycloalkyl).

In certain embodiments, $R^1$ is $R^{12}$-substituted or unsubstituted heterocycloalkyl (e.g., 3 to 8 membered heterocycloalkyl, 3 to 6 membered heterocycloalkyl, or 5 to 6 membered heterocycloalkyl). In certain embodiments, $R^1$ is $R^{12}$-substituted heterocycloalkyl (e.g., 3 to 8 membered heterocycloalkyl, 3 to 6 membered heterocycloalkyl, or 5 to 6 membered heterocycloalkyl). In certain embodiments, $R^1$ is an unsubstituted heterocycloalkyl (e.g., 3 to 8 membered heterocycloalkyl, 3 to 6 membered heterocycloalkyl, or 5 to 6 membered heterocycloalkyl).

In certain embodiments, $R^1$ is $R^{12}$-substituted or unsubstituted aryl (e.g., $C_6$-$C_{10}$ aryl, $C_{10}$ aryl, or phenyl). In certain embodiments, $R^1$ is $R^{12}$-substituted aryl (e.g., $C_6$-$C_{10}$ aryl, $C_{10}$ aryl, or phenyl). In certain embodiments, $R^1$ is an unsubstituted aryl (e.g., $C_6$-$C_{10}$ aryl, $C_{10}$ aryl, or phenyl).

In certain embodiments, $R^1$ is $R^{12}$-substituted or unsubstituted heteroaryl (e.g., 5 to 10 membered heteroaryl, 5 to 9 membered heteroaryl, or 5 to 6 membered heteroaryl). In certain embodiments, $R^1$ is $R^{12}$-substituted heteroaryl (e.g., 5 to 10 membered heteroaryl, 5 to 9 membered heteroaryl, or 5 to 6 membered heteroaryl). In certain embodiments, $R^1$ is an unsubstituted heteroaryl (e.g., 5 to 10 membered heteroaryl, 5 to 9 membered heteroaryl, or 5 to 6 membered heteroaryl).

In certain embodiments, $R^{1A}$ is hydrogen, halogen, $-CF_3$, $-CCl_3$, $-CBr_3$, $-CI_3$, $-COOH$, $-CONH_2$, $R^{12A}$-substituted or unsubstituted alkyl (e.g., $C_1$-$C_8$ alkyl, $C_1$-$C_6$ alkyl, or $C_1$-$C_4$ alkyl), $R^{12A}$-substituted or unsubstituted heteroalkyl (e.g., 2 to 8 membered heteroalkyl, 2 to 6 membered heteroalkyl, or 2 to 4 membered heteroalkyl), $R^{12A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{12A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{12A}$-substituted or unsubstituted aryl (e.g., $C_6$-$C_{10}$ aryl, $C_{10}$ aryl, or phenyl), or $R^{12A}$-substituted or unsubstituted heteroaryl (e.g., 5 to 10 membered heteroaryl, 5 to 9 membered heteroaryl, or 5 to 6 membered heteroaryl).

In certain embodiments, $R^{1B}$ is hydrogen, halogen, $-CF_3$, $-CCl_3$, $-CBr_3$, $-CI_3$, $-COOH$, $-CONH_2$, $R^{12B}$-substituted or unsubstituted alkyl (e.g., $C_1$-$C_8$ alkyl, $C_1$-$C_6$ alkyl, or $C_1$-$C_4$ alkyl), $R^{12B}$-substituted or unsubstituted heteroalkyl (e.g., 2 to 8 membered heteroalkyl, 2 to 6 membered heteroalkyl, or 2 to 4 membered heteroalkyl), $R^{12B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{12B}$- substituted or unsubstituted heterocycloalkyl (e.g., 3 to 8 membered heterocycloalkyl, 3 to 6 membered heterocycloalkyl, or 5 to 6 membered heterocycloalkyl), $R^{12B}$-substituted or unsubstituted aryl (e.g., $C_6$-$C_{10}$ aryl, $C_{10}$ aryl, or phenyl), or $R^{12B}$-substituted or unsubstituted heteroaryl (e.g., 5 to 10 membered heteroaryl, 5 to 9 membered heteroaryl, or 5 to 6 membered heteroaryl). In certain embodiments, $R^{1B}$ and $R^{1C}$ substituents bonded to the same nitrogen atom may optionally be joined to form a $R^{12B}$-substituted or unsubstituted heterocycloalkyl (e.g., 3 to 8 membered heterocycloalkyl, 3 to 6 membered heterocycloalkyl, or 5 to 6 membered heterocycloalkyl), or $R^{12B}$-substituted or unsubstituted heteroaryl (e.g., 5 to 10 membered heteroaryl, 5 to 9 membered heteroaryl, or 5 to 6 membered heteroaryl).

In certain embodiments, $R^{1C}$ is hydrogen, halogen, —$CF_3$, —$CCl_3$, —$CBr_3$, —$CI_3$, —COOH, —$CONH_2$, $R^{12C}$-substituted or unsubstituted alkyl (e.g., $C_1$-$C_8$ alkyl, $C_1$-$C_6$ alkyl, or $C_1$-$C_4$ alkyl), $R^{12C}$-substituted or unsubstituted heteroalkyl (e.g., 2 to 8 membered heteroalkyl, 2 to 6 membered heteroalkyl, or 2 to 4 membered heteroalkyl), $R^{12C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{12C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{12C}$-substituted or unsubstituted aryl (e.g., $C_6$-$C_{10}$ aryl, $C_{10}$ aryl, or phenyl), or $R^{12C}$-substituted or unsubstituted heteroaryl (e.g., 5 to 10 membered heteroaryl, 5 to 9 membered heteroaryl, or 5 to 6 membered heteroaryl). In certain embodiments, $R^{1B}$ and $R^{1C}$ substituents bonded to the same nitrogen atom may optionally be joined to form a $R^{12C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{12C}$-substituted or unsubstituted heteroaryl (e.g., 5 to 10 membered heteroaryl, 5 to 9 membered heteroaryl, or 5 to 6 membered heteroaryl).

In certain embodiments, $R^{1D}$ is hydrogen, halogen, —$CF_3$, —$CCl_3$, —$CBr_3$, —$CI_3$, —COOH, —$CONH_2$, $R^{12D}$-substituted or unsubstituted alkyl (e.g., $C_1$-$C_8$ alkyl, $C_1$-$C_6$ alkyl, or $C_1$-$C_4$ alkyl), $R^{12D}$-substituted or unsubstituted heteroalkyl (e.g., 2 to 8 membered heteroalkyl, 2 to 6 membered heteroalkyl, or 2 to 4 membered heteroalkyl), $R^{12D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{12D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{12D}$-substituted or unsubstituted aryl (e.g., $C_6$-$C_{10}$ aryl, $C_{10}$ aryl, or phenyl), or $R^{12D}$-substituted or unsubstituted heteroaryl (e.g., 5 to 10 membered heteroaryl, 5 to 9 membered heteroaryl, or 5 to 6 membered heteroaryl).

$R^9$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{10}$-substituted or unsubstituted alkyl (e.g., $C_1$-$C_8$ alkyl, $C_1$-$C_6$ alkyl, or $C_1$-$C_4$ alkyl), $R^{10}$-substituted or unsubstituted heteroalkyl (e.g., 2 to 8 membered heteroalkyl, 2 to 6 membered heteroalkyl, or 2 to 4 membered heteroalkyl), $R^{10}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{10}$-substituted or unsubstituted heterocycloalkyl (e.g., 3 to 8 membered heterocycloalkyl, or 5 to 6 membered heterocycloalkyl), $R^{10}$-substituted or unsubstituted aryl (e.g., $C_6$-$C_{10}$ aryl, $C_{10}$ aryl, or phenyl), or $R^{10}$-substituted or unsubstituted heteroaryl (e.g., 5 to 10 membered heteroaryl, 5 to 9 membered heteroaryl, or 5 to 6 membered heteroaryl).

In embodiments, $R^9$ is $R^{10}$-substituted or unsubstituted alkyl (e.g., $C_1$-$C_8$ alkyl, $C_1$-$C_6$ alkyl, or $C_1$-$C_4$ alkyl). In embodiments, $R^9$ is $R^{10}$-substituted alkyl (e.g., $C_1$-$C_8$ alkyl, $C_1$-$C_6$ alkyl, or $C_1$-$C_4$ alkyl). In embodiments, $R^9$ is an unsubstituted alkyl (e.g., $C_1$-$C_8$ alkyl, $C_1$-$C_6$ alkyl, or $C_1$-$C_4$ alkyl).

In embodiments, $R^9$ is $R^{10}$-substituted or unsubstituted heteroalkyl (e.g., 2 to 8 membered heteroalkyl, 2 to 6 membered heteroalkyl, or 2 to 4 membered heteroalkyl). In embodiments, $R^9$ is $R^{10}$-substituted heteroalkyl (e.g., 2 to 8 membered heteroalkyl, 2 to 6 membered heteroalkyl, or 2 to 4 membered heteroalkyl). In embodiments, $R^9$ is an unsubstituted heteroalkyl (e.g., 2 to 8 membered heteroalkyl, 2 to 6 membered heteroalkyl, or 2 to 4 membered heteroalkyl).

In embodiments, $R^9$ is $R^{10}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^9$ is $R^{10}$-substituted cycloalkyl (e.g., $C_3$-$C_8$ cycloalkyl, $C_3$-$C_6$ cycloalkyl, or $C_5$-$C_6$ cycloalkyl). In embodiments, $R^9$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^9$ is $R^{10}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^9$ is $R^{10}$-substituted heterocycloalkyl (e.g., 3 to 8 membered heterocycloalkyl, 3 to 6 membered heterocycloalkyl, or 5 to 6 membered heterocycloalkyl). In embodiments, $R^9$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^9$ is $R^{10}$-substituted or unsubstituted aryl (e.g., $C_6$-$C_{10}$ aryl, $C_{10}$ aryl, or phenyl). In embodiments, $R^9$ is $R^{10}$-substituted aryl (e.g., $C_6$-$C_{10}$ aryl, $C_{10}$ aryl, or phenyl). In embodiments, $R^9$ is an unsubstituted aryl (e.g., $C_6$-$C_{10}$ aryl, $C_{10}$ aryl, or phenyl).

In embodiments, $R^9$ is $R^{10}$-substituted or unsubstituted heteroaryl (e.g., 5 to 10 membered heteroaryl, 5 to 9 membered heteroaryl, or 5 to 6 membered heteroaryl). In embodiments, $R^9$ is $R^{10}$-substituted heteroaryl (e.g., 5 to 10 membered heteroaryl, 5 to 9 membered heteroaryl, or 5 to 6 membered heteroaryl). In embodiments, $R^9$ is an unsubstituted heteroaryl (e.g., 5 to 10 membered heteroaryl, 5 to 9 membered heteroaryl, or 5 to 6 membered heteroaryl).

$R^{10}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{11}$-substituted or unsubstituted alkyl (e.g., $C_1$-$C_8$ alkyl, $C_1$-$C_6$ alkyl, or $C_1$-$C_4$ alkyl), $R^{11}$-substituted or unsubstituted heteroalkyl (e.g., 2 to 8 membered heteroalkyl, 2 to 6 membered heteroalkyl, or 2 to 4 membered heteroalkyl), $R^{11}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{11}$-substituted or unsubstituted heterocycloalkyl (e.g., 3 to 8 membered heterocycloalkyl, 3 to 6 membered heterocycloalkyl, or 5 to 6 membered heterocycloalkyl), $R^{11}$-substituted or unsubstituted aryl (e.g., $C_6$-$C_{10}$ aryl, $C_{10}$ aryl, or phenyl), or $R^{11}$-substituted or unsubstituted heteroaryl (e.g., 5 to 10 membered heteroaryl, 5 to 9 membered heteroaryl, or 5 to 6 membered heteroaryl).

In embodiments, $R^{10}$ is $R^{11}$-substituted or unsubstituted alkyl (e.g., $C_1$-$C_8$ alkyl, $C_1$-$C_6$ alkyl, or $C_1$-$C_4$ alkyl). In embodiments, $R^{10}$ is $R_{11}$-substituted alkyl (e.g., $C_1$-$C_8$ alkyl, $C_1$-$C_6$ alkyl, or $C_1$-$C_4$ alkyl). In embodiments, $R^{10}$ is an unsubstituted alkyl (e.g., $C_1$-$C_8$ alkyl, $C_1$-$C_6$ alkyl, or $C_1$-$C_4$ alkyl).

In embodiments, $R^{10}$ is $R^{11}$-substituted or unsubstituted heteroalkyl (e.g., 2 to 8 membered heteroalkyl, 2 to 6 membered heteroalkyl, or 2 to 4 membered heteroalkyl). In embodiments, $R^{10}$ is $R^{11}$-substituted heteroalkyl (e.g., 2 to 8 membered heteroalkyl, 2 to 6 membered heteroalkyl, or 2 to 4 membered heteroalkyl). In embodiments, $R^{10}$ is an unsubstituted heteroalkyl (e.g., 2 to 8 membered heteroalkyl, 2 to 6 membered heteroalkyl, or 2 to 4 membered heteroalkyl).

In embodiments, $R^{10}$ is $R^{11}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{10}$ is $R^{11}$-substituted cycloalkyl (e.g., $C_3$-$C_8$ cycloalkyl, $C_3$-$C_6$ cycloalkyl, or $C_5$-$C_6$ cycloalkyl). In embodiments, $R^{10}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{10}$ is $R^{11}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{10}$ is $R^{11}$-substituted heterocycloalkyl (e.g., 3 to 8 membered heterocycloalkyl, 3 to 6 membered heterocycloalkyl, or 5 to 6 membered heterocycloalkyl). In embodiments, $R^{10}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{10}$ is $R^{11}$-substituted or unsubstituted aryl (e.g., $C_6$-$C_{10}$ aryl, $C_{10}$ aryl, or phenyl). In embodiments, $R^{10}$ is $R^{11}$-substituted aryl (e.g., $C_6$-$C_{10}$ aryl, $C_{10}$ aryl, or phenyl). In embodiments, $R^{10}$ is an unsubstituted aryl (e.g., $C_6$-$C_{10}$ aryl, $C_{10}$ aryl, or phenyl).

In embodiments, $R^{10}$ is $R^{11}$-substituted or unsubstituted heteroaryl (e.g., 5 to 10 membered heteroaryl, 5 to 9 membered heteroaryl, or 5 to 6 membered heteroaryl). In embodiments, $R^{10}$ is $R^{11}$-substituted heteroaryl (e.g., 5 to 10 membered heteroaryl, 5 to 9 membered heteroaryl, or 5 to 6 membered heteroaryl). In embodiments, $R^{10}$ is an unsubstituted heteroaryl (e.g., 5 to 10 membered heteroaryl, 5 to 9 membered heteroaryl, or 5 to 6 membered heteroaryl).

$R^{12}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{13}$-substituted or unsubstituted alkyl (e.g., $C_1$-$C_8$ alkyl, $C_1$-$C_6$ alkyl, or $C_1$-$C_4$ alkyl), $R^{13}$-substituted or unsubstituted heteroalkyl (e.g., 2 to 8 membered heteroalkyl, 2 to 6 membered heteroalkyl, or 2 to 4 membered heteroalkyl), $R^{13}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{13}$-substituted or unsubstituted heterocycloalkyl (e.g., 3 to 8 membered heterocycloalkyl, 3 to 6 membered heterocycloalkyl, or 5 to 6 membered heterocycloalkyl), $R^{13}$-substituted or unsubstituted aryl (e.g., $C_6$-$C_{10}$ aryl, $C_{10}$ aryl, or phenyl), or $R^{13}$ substituted or unsubstituted heteroaryl (e.g., 5 to 10 membered heteroaryl, 5 to 9 membered heteroaryl, or 5 to 6 membered heteroaryl).

In certain embodiments, $R^{12}$ is $R^{13}$-substituted or unsubstituted alkyl (e.g., $C_1$-$C_8$ alkyl, $C_1$-$C_6$ alkyl, or $C_1$-$C_4$ alkyl). In certain embodiments, $R^{12}$ is $R^{13}$-substituted alkyl (e.g., $C_1$-$C_8$ alkyl, $C_1$-$C_6$ alkyl, or $C_1$-$C_4$ alkyl). In certain embodiments, $R^{12}$ is an unsubstituted alkyl (e.g., $C_1$-$C_8$ alkyl, $C_1$-$C_6$ alkyl, or $C_1$-$C_4$ alkyl).

In certain embodiments, $R^{12}$ is $R^{13}$-substituted or unsubstituted heteroalkyl (e.g., 2 to 8 membered heteroalkyl, 2 to 6 membered heteroalkyl, or 2 to 4 membered heteroalkyl). In certain embodiments, $R^{12}$ is $R^{13}$-substituted heteroalkyl (e.g., 2 to 8 membered heteroalkyl, 2 to 6 membered heteroalkyl, or 2 to 4 membered heteroalkyl). In certain embodiments, $R^{12}$ is an unsubstituted heteroalkyl (e.g., 2 to 8 membered heteroalkyl, 2 to 6 membered heteroalkyl, or 2 to 4 membered heteroalkyl).

In certain embodiments, $R^{12}$ is $R^{13}$-substituted or unsubstituted cycloalkyl (e.g., $C_3$-$C_8$ cycloalkyl, $C_3$-$C_6$ cycloalkyl, or $C_5$-$C_6$ cycloalkyl). In certain embodiments, $R^{12}$ is $R^{13}$-substituted cycloalkyl (e.g., $C_3$-$C_8$ cycloalkyl, $C_3$-$C_6$ cycloalkyl, or $C_5$-$C_6$ cycloalkyl). In certain embodiments, $R^{12}$ is an unsubstituted cycloalkyl (e.g., $C_3$-$C_8$ cycloalkyl, $C_3$-$C_6$ cycloalkyl, or $C_5$-$C_6$ cycloalkyl).

In certain embodiments, $R^{12}$ is $R^{13}$-substituted or unsubstituted heterocycloalkyl (e.g., 3 to 8 membered heterocycloalkyl, 3 to 6 membered heterocycloalkyl, or 5 to 6 membered heterocycloalkyl). In certain embodiments, $R^{12}$ is $R^{13}$-substituted heterocycloalkyl (e.g., 3 to 8 membered heterocycloalkyl, 3 to 6 membered heterocycloalkyl, or 5 to 6 membered heterocycloalkyl). In certain embodiments, $R^{12}$ is an unsubstituted heterocycloalkyl (e.g., 3 to 8 membered heterocycloalkyl, 3 to 6 membered heterocycloalkyl, or 5 to 6 membered heterocycloalkyl).

In certain embodiments, $R^{12}$ is $R^{13}$-substituted or unsubstituted aryl (e.g., $C_6$-$C_{10}$ aryl, $C_{10}$ aryl, or phenyl). In certain embodiments, $R^{12}$ is $R^{13}$-substituted aryl (e.g., $C_6$-$C_{10}$ aryl, $C_{10}$ aryl, or phenyl). In certain embodiments, $R^{12}$ is an unsubstituted aryl (e.g., $C_6$-$C_{10}$ aryl, $C_{10}$ aryl, or phenyl).

In certain embodiments, $R^{12}$ is $R^{13}$-substituted or unsubstituted heteroaryl (e.g., 5 to 10 membered heteroaryl, 5 to 9 membered heteroaryl, or 5 to 6 membered heteroaryl). In certain embodiments, $R^{12}$ is $R^{13}$-substituted heteroaryl (e.g., 5 to 10 membered heteroaryl, 5 to 9 membered heteroaryl, or 5 to 6 membered heteroaryl). In certain embodiments, $R^{12}$ is an unsubstituted heteroaryl (e.g., 5 to 10 membered heteroaryl, 5 to 9 membered heteroaryl, or 5 to 6 membered heteroaryl).

$R^{13}$ is independently oxo, halogen, —$CCl_3$, —$ClBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{14}$-substituted or unsubstituted alkyl (e.g., $C_1$-$C_8$ alkyl, $C_1$-$C_6$ alkyl, or $C_1$-$C_4$ alkyl), $R^{14}$-substituted or unsubstituted heteroalkyl (e.g., 2 to 8 membered heteroalkyl, 2 to 6 membered heteroalkyl, or 2 to 4 membered heteroalkyl), $R^{14}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{14}$-substituted or unsubstituted heterocycloalkyl (e.g., 3 to 8 membered heterocycloalkyl, 3 to 6 membered heterocycloalkyl, or 5 to 6 membered heterocycloalkyl), $R^{14}$-substituted or unsubstituted aryl (e.g., $C_6$-$C_{10}$ aryl, $C_{10}$ aryl, or phenyl), or $R^{14}$-substituted or unsubstituted heteroaryl (e.g., 5 to 10 membered heteroaryl, 5 to 9 membered heteroaryl, or 5 to 6 membered heteroaryl).

In certain embodiments, $R^{13}$ is $R^{14}$-substituted or unsubstituted alkyl (e.g., $C_1$-$C_8$ alkyl, $C_1$-$C_6$ alkyl, or $C_1$-$C_4$ alkyl). In certain embodiments, $R^{13}$ is $R^{14}$-substituted alkyl (e.g., $C_1$-$C_8$ alkyl, $C_1$-$C_6$ alkyl, or $C_1$-$C_4$ alkyl). In certain embodiments, $R^{13}$ is an unsubstituted alkyl (e.g., $C_1$-$C_8$ alkyl, $C_1$-$C_6$ alkyl, or $C_1$-$C_4$ alkyl).

In certain embodiments, $R^{13}$ is $R^{14}$-substituted or unsubstituted heteroalkyl (e.g., 2 to 8 membered heteroalkyl, 2 to 6 membered heteroalkyl, or 2 to 4 membered heteroalkyl). In certain embodiments, $R^{13}$ is $R^{14}$-substituted heteroalkyl (e.g., 2 to 8 membered heteroalkyl, 2 to 6 membered heteroalkyl, or 2 to 4 membered heteroalkyl). In certain embodiments, $R^{13}$ is an unsubstituted heteroalkyl (e.g., 2 to 8 membered heteroalkyl, 2 to 6 membered heteroalkyl, or 2 to 4 membered heteroalkyl).

In certain embodiments, $R^{13}$ is $R^{14}$-substituted or unsubstituted cycloalkyl (e.g., $C_3$-$C_8$ cycloalkyl, $C_3$-$C_6$ cycloalkyl, or $C_5$-$C_6$ cycloalkyl). In certain embodiments, $R_{13}$ is $R^{14}$-substituted cycloalkyl (e.g., $C_3$-$C_8$ cycloalkyl, $C_3$-$C_6$ cycloalkyl, or $C_5$-$C_6$ cycloalkyl). In certain embodiments, $R^{13}$ is an unsubstituted cycloalkyl (e.g., $C_3$-$C_8$ cycloalkyl, $C_3$-$C_6$ cycloalkyl, or $C_5$-$C_6$ cycloalkyl).

In certain embodiments, $R^{13}$ is $R^{14}$-substituted or unsubstituted heterocycloalkyl (e.g., 3 to 8 membered heterocycloalkyl, 3 to 6 membered heterocycloalkyl, or 5 to 6 membered heterocycloalkyl). In certain embodiments, $R^{13}$ is $R^{14}$-substituted heterocycloalkyl (e.g., 3 to 8 membered heterocycloalkyl, 3 to 6 membered heterocycloalkyl, or 5 to 6 membered heterocycloalkyl). In certain embodiments, $R^{13}$ is an unsubstituted heterocycloalkyl (e.g., 3 to 8 membered heterocycloalkyl, 3 to 6 membered heterocycloalkyl, or 5 to 6 membered heterocycloalkyl).

In certain embodiments, $R^{13}$ is $R^{14}$-substituted or unsubstituted aryl (e.g., $C_6$-$C_{10}$ aryl, $C_{10}$ aryl, or phenyl). In certain embodiments, $R^{13}$ is $R^{14}$-substituted aryl (e.g., $C_6$-$C_{10}$ aryl, $C_{10}$ aryl, or phenyl). In certain embodiments, $R^{13}$ is an unsubstituted aryl (e.g., $C_6$-$C_{10}$ aryl, $C_{10}$ aryl, or phenyl).

In certain embodiments, $R^{13}$ is $R^{14}$-substituted or unsubstituted heteroaryl (e.g., 5 to 10 membered heteroaryl, 5 to 9 membered heteroaryl, or 5 to 6 membered heteroaryl). In certain embodiments, $R^{13}$ is $R^{14}$-substituted heteroaryl (e.g., 5 to 10 membered heteroaryl, 5 to 9 membered heteroaryl, or 5 to 6 membered heteroaryl). In certain embodiments, $R^{13}$ is an unsubstituted heteroaryl (e.g., 5 to 10 membered heteroaryl, 5 to 9 membered heteroaryl, or 5 to 6 membered heteroaryl). $R^{11}$, $R^{12A}$, $R^{12B}$, $R^{12C}$, $R^{12D}$, and $R^{14}$ are independently hydrogen, oxo, halogen, —$CCl_3$, —$CBr_3$, —$CF_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

III. Pharmaceutical Compositions

In an aspect is provided a pharmaceutical composition, comprising the structural Formula (IV), (IV-A), (IV-B), (V-A), (V-B), (VI-A), (VI-B), (VII-A), and/or (VII-B), or an alkene isomer, tautomer, or an isotopic variant thereof; or a pharmaceutically acceptable salt, solvate, hydrate, or prodrug thereof, and at least one pharmaceutically acceptable excipient.

In an aspect, provided herein is a pharmaceutical composition, comprising a compound, wherein the compound is:

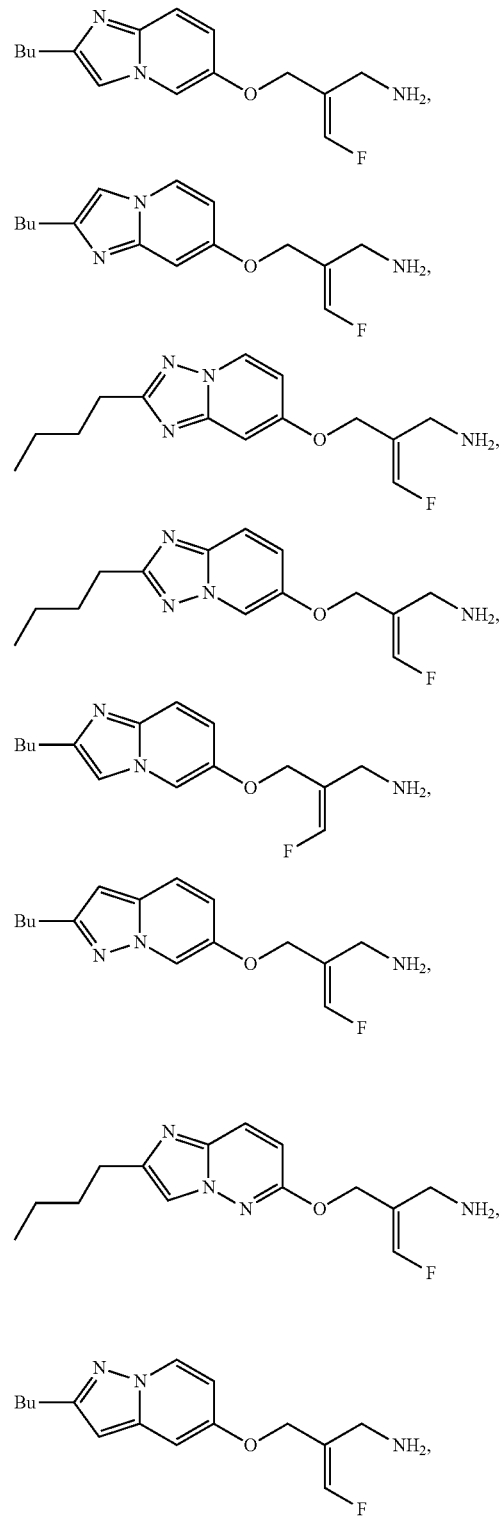

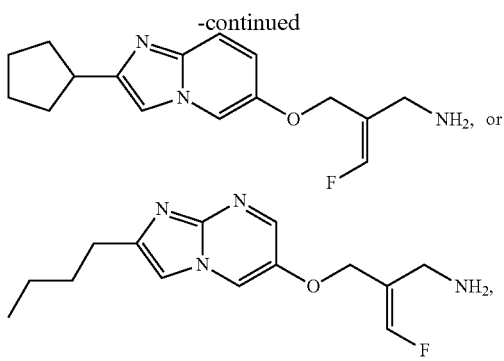

or an alkene isomer, tautomer, or an isotopic variant thereof; or a pharmaceutically acceptable salt, solvate, hydrate, or prodrug thereof and at least one pharmaceutically acceptable excipient.

In some embodiments, the at least one pharmaceutically acceptable excipient is a pharmaceutically acceptable ophthalmic carrier.

The compounds (e.g., VAP-1 inhibitors) of the present disclosure may be in the form of compositions suitable for administration to a subject. In general, such compositions are "pharmaceutical compositions" comprising a compound (e.g., VAP-1 inhibitor(s)) and one or more pharmaceutically acceptable or physiologically acceptable diluents, carriers, or excipients. In certain embodiments, the compounds (e.g., VAP-1 inhibitors) are present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein.

The pharmaceutical compositions containing the active ingredient (e.g., an inhibitor of VAP-1 function) may be in a form suitable for oral use, for example, as tablets or capsules, (e.g., hard or soft capsules). Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture thereof. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

The pharmaceutical compositions typically comprise a therapeutically effective amount of a VAP-1 inhibitor contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate-buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer; N-(2-Hydroxyethyl)piperazine-N'-(2-ethanesulfonic acid) (HEPES); 2-(N-Morpholino)ethanesulfonic acid (MES); 2-(N-Morpholino)ethanesulfonic acid sodium salt (MES); 3-(N-Morpholino)propanesulfonic acid (MOPS); and N-tris[Hydroxymethyl]methyl-3-aminopropanesulfonic acid (TAPS).

Formulations can also include carriers to protect the composition against rapid degradation or elimination from the body, such as a controlled release formulation, including liposomes, hydrogels, prodrugs and microencapsulated delivery systems. For example, a time-delay material such as glyceryl monostearate or glyceryl stearate alone, or in combination with a wax, may be employed. Any drug delivery apparatus may be used to deliver a VAP-1 inhibitor, including implants (e.g., implantable pumps) and catheter systems, slow injection pumps and devices, all of which are well known to the skilled artisan.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor® EL (BASF, Parsippany, NJ) or phosphate buffered saline (PBS), ethanol, polyol (e.g., glycerol, propylene glycol, and liquid polyethylene glycol), and suitable mixtures thereof. In addition, sterile fixed oils are conventionally employed as a solvent or suspending medium; for this purpose, any bland fixed oil may be employed, including synthetic mono- or diglycerides. Moreover, fatty acids, such as oleic acid, find use in the preparation of injectables. Prolonged absorption of particular injectable formulations can be achieved by including an agent that delays absorption (e.g., aluminum monostearate or gelatin).

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

The VAP-1 compounds used in the methods described herein are, in some instances, in the form of a sterile injectable aqueous or oleagenous suspension. This suspension may be formulated according to know methods using those suitable dispersing or wetting agents and suspending agents that have been mentioned above. The sterile injectable preparation may also be formulated as a suspension in a non toxic parenterally-acceptable diluent or solvent, for example as a solution in 1,3-butanediol. Among the acceptable vehicles and solvents that may be employed are water, Ringers solution and isotonic sodium chloride solution. For this purpose any bland fixed oil may be employed including synthetic mono- or diglycerides. In addition fatty acids such as oleic acid find use in the preparation of injectables.

In some embodiments, the composition is in a form of a solution (e.g., an aqueous solution).

In some instances, the composition described herein further comprises a preservative. In some cases, a preservative is added at a concentration to a composition described herein to prevent the growth of or to destroy a microorganism introduced into the composition.

In some embodiments, the preservative is selected from benzalkonium chloride, cetrimonium, sodium perborate, stabilized oxychloro complex, SofZia (Alcon), polyquaternium-1, chlorobutanol, edetate disodium, and polyhexamethylene biguanide.

In some instances, the composition described herein further comprises a disinfecting agent. In some cases, disinfecting agents include polymeric biguanides, polymeric quarternary ammonium compounds, chlorites, bisbiguanides, chlorite compounds (e.g., potassium chlorite, sodium chlorite, calcium chlorite, magnesium chlorite, or mixtures thereof), and a combination thereof.

In some embodiments, the ophthalmic composition further comprises a buffer agent. In some embodiments, the buffer agent is selected from borates, borate-polyol complexes, phosphate buffering agents, citrate buffering agents, acetate buffering agents, carbonate buffering agents, organic buffering agents, amino acid buffering agents, or combinations thereof.

In some instances, borates include boric acid, salts of boric acid, other pharmaceutically acceptable borates, and combinations thereof. In some cases, borates include boric acid, sodium borate, potassium borate, calcium borate, magnesium borate, manganese borate, and other such borate salts.

As used herein, the term polyol includes any compound having at least one hydroxyl group on each of two adjacent carbon atoms that are not in trans configuration relative to each other. In some embodiments, the polyols is linear or cyclic, substituted or unsubstituted, or mixtures thereof, so long as the resultant complex is water soluble and pharmaceutically acceptable. In some instances, examples of polyol include: sugars, sugar alcohols, sugar acids and uronic acids. In some cases, polyols include, but are not limited to: mannitol, glycerin, xylitol, and sorbitol.

In some embodiments, phosphate buffering agents include phosphoric acid; alkali metal phosphates such as disodium hydrogen phosphate, sodium dihydrogen phosphate, trisodium phosphate, dipotassium hydrogen phosphate, potassium dihydrogen phosphate, and tripotassium phosphate; alkaline earth metal phosphates such as calcium phosphate, calcium hydrogen phosphate, calcium dihydrogen phosphate, monomagnesium phosphate, dimagnesium phosphate (magnesium hydrogen phosphate), and trimagnesium phosphate; ammonium phosphates such as diammonium hydrogen phosphate and ammonium dihydrogen phosphate; or a combination thereof. In some instances, the phosphate buffering agent is an anhydride. In some instances, the phosphate buffering agent is a hydrate.

In some embodiments, borate-polyol complexes include those described in U.S. Pat. No. 6,503,497. In some instances, the borate-polyol complexes comprise borates in an amount of from about 0.01 to about 2.0% w/v, and one or more polyols in an amount of from about 0.01% to about 5.0% w/v.

In some cases, citrate buffering agents include citric acid and sodium citrate.

In some instances, acetate buffering agents include acetic acid, potassium acetate, and sodium acetate.

In some instances, carbonate buffering agents include sodium bicarbonate and sodium carbonate.

In some cases, organic buffering agents include Good's Buffer, such as for example 2-(N-morpholino)ethanesulfonic acid (MES), N-(2-Acetamido)iminodiacetic acid, N-(Carbamoylmethyl)iminodiacetic acid (ADA), piperazine-N,N'-bis(2-ethanesulfonic acid (PIPES), N-(2-acetamido)-2-aminoethanesulfonic acid (ACES), β-Hydroxy-4-morpholinepropanesulfonic acid, 3-Morpholino-2-hydroxypropanesulfonic acid (MOPSO), cholamine chloride, 3-(N-morpholino)propansulfonic acid (MOPS), N,N-bis(2-hydroxyethyl)-2-aminoethanesulfonic acid (BES), 2-[(2-Hydroxy-1,1-bis(hydroxymethyl)ethyl)amino]ethanesulfonic acid (TES), 4-(2-hydroxyethyl)-1-piperazineethanesulfonic acid (HEPES), 3-(N,N-Bis[2-hydroxyethyl]amino)-2-hydroxypropanesulfonic acid (DIPSO), acetamidoglycine, 3-{[1,3-Dihydroxy-2-(hydroxymethyl)-2-propanyl]amino}-2-hydroxy-1-propanesulfonic acid (TAPSO), piperazine-1,4,-bis (2-hydroxypropanesulphonic acid) (POPSO), 4-(2-hydroxyethyl)piperazine-1-(2-hydroxypropanesulfonic acid) hydrate (HEPPSO), 3-[4-(2-hydroxyethyl)-1-piperazinyl]propanesulfonic acid (HEPPS), tricine, glycinamide, bicine or N-tris(hydroxymethyl)methyl-3-aminopropanesulfonic acid sodium (TAPS); glycine; and diethanolamine (DEA).

In some cases, amino acid buffering agents include taurine, aspartic acid and its salts (e.g., potassium salts, etc), E-aminocaproic acid, and the like.

In some instances, the composition described herein further comprises a tonicity adjusting agent. Tonicity adjusting agent is an agent introduced into a preparation such as an ophthalmic composition to reduce local irritation by preventing osmotic shock at the site of application. In some instances, buffer solution and/or a pD adjusting agent that broadly maintains the ophthalmic solution at a particular ion concentration and pD are considered as tonicity adjusting agents. In some cases, tonicity adjusting agents include various salts, such as halide salts of a monovalent cation. In some cases, tonicity adjusting agents include mannitol, sorbitol, dextrose, sucrose, urea, and glycerin. In some instances, suitable tonicity adjustors comprise sodium chloride, sodium nitrate, sodium sulfate, sodium bisulfate, potassium chloride, calcium chloride, magnesium chloride, zinc chloride, potassium acetate, sodium acetate, sodium bicarbonate, sodium carbonate, sodium thiosulfate, magnesium sulfate, disodium hydrogen phosphate, sodium dihydrogen phosphate, potassium dihydrogen phosphate, dextrose, mannitol, sorbitol, dextrose, sucrose, urea, propylene glycol, glycerin, or a combination thereof.

In some instances, the concentration of the tonicity adjusting agent in a composition described herein is between about 0.5% and about 10.0%. In some cases, the percentage is a weight percentage.

In some cases, the composition described herein further comprises a pD adjusting agent. In some embodiments, the pD adjusting agent used is an acid or a base. In some embodiments, the base is oxides, hydroxides, carbonates, bicarbonates, and the likes. In some instances, the oxides are metal oxides such as calcium oxide, magnesium oxide, and the likes; hydroxides are of alkali metals and alkaline earth metals such as sodium hydroxide, potassium hydroxide, calcium hydroxide, and the likes or their deuterated equivalents; and carbonates are sodium carbonate, sodium bicarbonates, potassium bicarbonates, and the likes. In some instances, the acid is mineral acid and organic acids such as hydrochloric acid, nitric acid, phosphoric acid, acetic acid, citric acid, fumaric acid, malic acid tartaric acid and the likes or their deuterated equivalents. In some instances, the pD adjusting agent includes, but is not limited to, acetate, bicarbonate, ammonium chloride, citrate, phosphate, pharmaceutically acceptable salts thereof and combinations or mixtures thereof.

In some instances, the composition described herein further comprises a disinfecting agent. In some cases, disinfecting agents include polymeric biguanides, polymeric quarternary ammonium compounds, chlorites, bisbiguanides, chlorite compounds (e.g., potassium chlorite, sodium chlorite, calcium chlorite, magnesium chlorite, or mixtures thereof), and a combination thereof.

In some instances, the composition described herein further comprises a stabilizing agent or stabilizer. Stabilizers that are useful in the ophthalmically acceptable formulations disclosed herein include, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used. In further embodiments, the chosen stabilizer changes the hydrophobicity of the formulation, improves the mixing of various components in the formulation, controls the moisture level in the formula, or controls the mobility of the phase.

In other embodiments, stabilizers are present in sufficient amounts to inhibit the degradation of the ophthalmic agent. Examples of such stabilizing agents, include, but are not limited to: glycerol, methionine, monothioglycerol, EDTA, ascorbic acid, polysorbate 80, polysorbate 20, arginine, heparin, dextran sulfate, cyclodextrins, pentosan polysulfate and other heparinoids, divalent cations such as magnesium and zinc, or combinations thereof.

Additional useful stabilization agents for ophthalmically acceptable formulations include one or more anti-aggregation additives to enhance stability of ophthalmic formulations by reducing the rate of protein aggregation. The anti-aggregation additive selected depends upon the nature of the conditions to which the ophthalmic agents, for example a VAP-1 inhibitor, are exposed. For example, certain formulations undergoing agitation and thermal stress require a different anti-aggregation additive than a formulation undergoing lyophilization and reconstitution. Useful anti-aggregation additives include, by way of example only, urea, guanidinium chloride, simple amino acids such as glycine or arginine, sugars, polyalcohols, polysorbates, polymers such as polyethylene glycol and dextrans, alkyl saccharides, such as alkyl glycoside, and surfactants.

Other useful formulations optionally include one or more ophthalmically acceptable antioxidants to enhance chemical stability where required. Suitable antioxidants include, by way of example only, ascorbic acid, methionine, sodium thiosulfate and sodium metabisulfite. In one embodiment, antioxidants are selected from metal chelating agents, thiol-containing compounds, and other general stabilizing agents.

Still other useful compositions include one or more ophthalmically acceptable surfactants to enhance physical stability or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

In other embodiments, an additional surfactant (co-surfactant) and/or buffering agent is combined with one or more of the pharmaceutically acceptable vehicles previously described herein so that the surfactant and/or buffering agent maintains the product at an optimal pD for stability. Suitable co-surfactants include, but are not limited to: a) natural and synthetic lipophilic agents, e.g., phospholipids, cholesterol, and cholesterol fatty acid esters and derivatives thereof; b) nonionic surfactants, which include for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethyleneglycerol triiricinoleate, and any combinations or mixtures thereof c) anionic surfactants include, but are not limited to, calcium carboxymethylcellulose, sodium carboxymethylcellulose, sodium sulfosuccinate, dioctyl, sodium alginate, alkyl polyoxyethylene sulfates, sodium lauryl sulfate, triethanolamine stearate, potassium laurate, bile salts, and any combinations or mixtures thereof and d) cationic surfactants such as cetyltrimethylammonium bromide, and lauryldimethylbenzyl-ammonium chloride.

In some embodiments, the pD of a composition described herein is adjusted (e.g., by use of a buffer and/or a pD adjusting agent) to an ophthalmically compatible pD range of from about 4 to about 8, about 4.5 to about 7.5, or about 5 to about 7. In some embodiments, the ophthalmic composition has a pD of from about 5.0 to about 7.0. In some embodiments, the ophthalmic composition has a pD of from about 5.5 to about 7.0. In some embodiments, the ophthalmic composition has a pD of from about 6.0 to about 7.0.

In some embodiments, useful formulations include one or more pD adjusting agents or buffering agents. Suitable pD adjusting agents or buffers include, but are not limited to acetate, bicarbonate, ammonium chloride, citrate, phosphate, deuterated forms of acetate, bicarbonate, ammonium chloride, citrate, phosphate, pharmaceutically acceptable salts thereof and combinations or mixtures thereof.

In one embodiment, when one or more buffers are utilized in the formulations of the present disclosure, they are combined, e.g., with a pharmaceutically acceptable vehicle and are present in the final formulation, e.g., in an amount ranging from about 0.1% to about 20% or from about 0.5% to about 10%. In certain embodiments of the present disclosure, the amount of buffer included in the gel formulations are an amount such that the pD of the gel formulation does not interfere with the body's natural buffering system.

In one embodiment, diluents are also used to stabilize compounds because they provide a more stable environment. In some instances, salts dissolved in buffered solutions (which also provides pD control or maintenance) are utilized as diluents in the art, including, but not limited to a phosphate buffered saline solution.

In some embodiments, the pD is calculated according to the formula disclosed in Glasoe et al., "Use of glass electrodes to measure acidities in deuterium oxide," J. Physical Chem. 64(1): 188-190 (1960).

Aqueous Solution Dose-To-Dose Uniformity

Typical ophthalmic aqueous solutions are packaged in eye drop bottles and administered as drops. For example, a single administration (i.e., a single dose) of an ophthalmic aqueous solution includes a single drop, two drops, three drops, or more into the eyes of the patient or subject. In some embodiments, one dose of the ophthalmic aqueous solution described herein is one drop of the aqueous solution composition from the eye drop bottle.

In some cases, described herein include ophthalmic aqueous compositions which provide a dose-to-dose uniform concentrations. In some instances, the dose-to-dose uniform concentration does not present significant variations of drug content from one dose to another. In some instances, the dose-to-dose uniform concentration does provide consistent drug content from one dose to another.

In some embodiments, the composition has a dose-to-dose ophthalmic agent concentration variation of less than 50%. In some embodiments, the composition has a dose-to-dose ophthalmic agent concentration variation of less than 40%. In some embodiments, the composition has a dose-to-dose ophthalmic agent concentration variation of less than 30%. In some embodiments, the composition has a dose-to-dose ophthalmic agent concentration variation of less than 20%. In some embodiments, the composition has a dose-to-dose ophthalmic agent concentration variation of less than 10%. In some embodiments, the composition has a dose-to-dose ophthalmic agent concentration variation of less than 5%.

In some embodiments, the dose-to-dose ophthalmic agent concentration variation is based on 10 consecutive doses. In some embodiments, the dose-to-dose ophthalmic agent concentration variation is based on 8 consecutive doses. In some embodiments, the dose-to-dose ophthalmic agent concentration variation is based on 5 consecutive doses. In some embodiments, the dose-to-dose ophthalmic agent concentration variation is based on 3 consecutive doses. In some embodiments, the dose-to-dose ophthalmic agent concentration variation is based on 2 consecutive doses.

A nonsettling formulation should not require shaking to disperse drug uniformly. A "no-shake" formulation is potentially advantageous over formulations that require shaking since patients' shaking behavior is a major source of variability in the amount of drug dosed. It has been reported that patients often times do not or forget to shake their ophthalmic compositions that requires shaking before administering a dose, despite the instructions to shake that were clearly marked on the label. On the other hand, even for those patients who do shake the product, it is normally not possible to determine whether the shaking is adequate in intensity and/or duration to render the product uniform. In some embodiments, the ophthalmic gel compositions and ophthalmic ointment compositions described herein are "no-shake" formulations that maintained the dose-to-dose uniformity described herein.

Aqueous Solution Viscosity

In some embodiments, the composition has a Brookfield RVDV viscosity of from about 10 to about 50,000 cps at about 20° C. and sheer rate of 1 $s^{-1}$. In some embodiments, the composition has a Brookfield RVDV viscosity of from about 100 to about 40,000 cps at about 20° C. and sheer rate of 1 $s^{-1}$. In some embodiments, the composition has a Brookfield RVDV viscosity of from about 500 to about 30,000 cps at about 20° C. and sheer rate of 1 $s^{-1}$. In some embodiments, the composition has a Brookfield RVDV viscosity of from about 1000 to about 20,000 cps at about 20° C. and sheer rate of 1 $s^{-1}$. In some embodiments, the composition has a Brookfield RVDV viscosity of from about 2000 to about 10,000 cps at about 20° C. and sheer rate of 1 $s^{-1}$. In some embodiments, the composition has a Brookfield RVDV viscosity of from about 4000 to about 8000 cps at about 20° C. and sheer rate of 1 s$^{-1}$.

In some embodiments, the ophthalmic aqueous formulation contains a viscosity enhancing agent sufficient to provide a viscosity of between about 500 and 50,000 centipoise; between about 750 and 50,000 centipoise; between about 1000 and 50,000 centipoise; between about 1000 and 40,000 centipoise; between about 2000 and 30,000 centipoise; between about 3000 and 20,000 centipoise; between about 4000 and 10,000 centipoise; or between about 5000 and 8000 centipoise.

In some embodiments, the compositions described herein are low viscosity compositions at body temperature. In some embodiments, low viscosity compositions contain from about 1% to about 10% of a viscosity-enhancing agent (e.g., gelling components such as polyoxyethylene-polyoxypropylene copolymers). In some embodiments, low viscosity compositions contain from about 2% to about 10% of a viscosity enhancing agent (e.g., gelling components such as polyoxyethylene-polyoxypropylene copolymers). In some embodiments, low viscosity compositions contain from about 5% to about 10% of a viscosity enhancing agent (e.g., gelling components such as polyoxyethylene-polyoxypropylene copolymers). In some embodiments, low viscosity compositions are substantially free of a viscosity enhancing agent (e.g., gelling components such as polyoxyethylene-polyoxypropylene copolymers). In some embodiments, a low viscosity ophthalmic agent composition described herein provides an apparent viscosity of from about 100 cP to about 10,000 cP. In some embodiments, a low viscosity ophthalmic agent composition described herein provides an apparent viscosity of from about 500 cP to about 10,000 cP. In some embodiments, a low viscosity ophthalmic agent composition described herein provides an apparent viscosity of from about 1000 cP to about 10,000 cP.

Osmolarity

In some embodiments, a composition disclosed herein is formulated in order to not disrupt the ionic balance of the eye. In some embodiments, a composition disclosed herein has an ionic balance that is the same as or substantially the same as the eye. In some embodiments, a composition disclosed herein does not does not disrupt the ionic balance of the eye.

As used herein, "practical osmolarity/osmolality" or "deliverable osmolarity/osmolality" means the osmolarity/osmolality of a composition as determined by measuring the osmolarity/osmolality of the ophthalmic agent and all excipients except the gelling and/or the thickening agent (e.g., polyoxyethylene-polyoxypropylene copolymers, carboxymethylcellulose or the like). The practical osmolarity of a composition disclosed herein is measured by a suitable method, e.g., a freezing point depression method as described in Viegas et. al., Int. J. Pharm., 1998, 160, 157-162. In some instances, the practical osmolarity of a composition disclosed herein is measured by vapor pressure osmometry (e.g., vapor pressure depression method) that allows for determination of the osmolarity of a composition at higher temperatures. In some instances, vapor pressure depression method allows for determination of the osmolarity of a composition comprising a gelling agent (e.g., a thermoreversible polymer) at a higher temperature wherein the gelling agent is in the form of a gel.

In some embodiments, the osmolarity at a target site of action (e.g., the eye) is about the same as the delivered osmolarity of a composition described herein. In some embodiments, a composition described herein has a deliverable osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L.

The practical osmolality of an ophthalmic composition disclosed herein is from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, a composition described herein has a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L.

In some embodiments, suitable tonicity adjusting agents include, but are not limited to any pharmaceutically acceptable sugar, salt or any combinations or mixtures thereof, such as, but not limited to dextrose, glycerin, mannitol, sorbitol, sodium chloride, and other electrolytes. In some instances, the tonicity adjusting agent is selected from sodium chloride, sodium nitrate, sodium sulfate, sodium bisulfate, potassium chloride, calcium chloride, magnesium chloride, zinc chloride, potassium acetate, sodium acetate, sodium bicarbonate, sodium carbonate, sodium thiosulfate, magnesium sulfate, disodium hydrogen phosphate, sodium dihydrogen phosphate, potassium dihydrogen phosphate, dextrose, mannitol, sorbitol, dextrose, sucrose, urea, propylene glycol, glycerin, or a combination thereof.

In some embodiment, the ophthalmic compositions described herein include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Sterility

In some embodiments, the compositions are sterilized. Included within the embodiments disclosed herein are means and processes for sterilization of a pharmaceutical composition disclosed herein for use in humans. The goal is to provide a safe pharmaceutical product, relatively free of infection causing micro-organisms. The U. S. Food and Drug Administration has provided regulatory guidance in the publication "Guidance for Industry: Sterile Drug Products Produced by Aseptic Processing" available at: http://www.fda.gov/cder/guidance/5882fnl.htm, which is incorporated herein by reference in its entirety.

As used herein, sterilization means a process used to destroy or remove microorganisms that are present in a product or packaging. Any suitable method available for sterilization of objects and compositions is used. Available methods for the inactivation of microorganisms include, but are not limited to, the application of extreme heat, lethal chemicals, or gamma radiation. In some embodiments, a process for the preparation of an ophthalmic formulation comprises subjecting the formulation to a sterilization method selected from heat sterilization, chemical sterilization, radiation sterilization or filtration sterilization. The method used depends largely upon the nature of the device or composition to be sterilized. Detailed descriptions of many methods of sterilization are given in Chapter 40 of Remington: The Science and Practice of Pharmacy published by Lippincott, Williams & Wilkins, and is incorporated by reference with respect to this subject matter.

Filtration

Filtration sterilization is a method used to remove but not destroy microorganisms from solutions. Membrane filters are used to filter heat-sensitive solutions. Such filters are thin, strong, homogenous polymers of mixed cellulosic esters (MCE), polyvinylidene fluoride (PVF; also known as PVDF), or polytetrafluoroethylene (PTFE) and have pore sizes ranging from 0.1 to 0.22 µm. Solutions of various characteristics are optionally filtered using different filter membranes. For example, PVF and PTFE membranes are well suited to filtering organic solvents while aqueous solutions are filtered through PVF or MCE membranes. Filter apparatus are available for use on many scales ranging from the single point-of-use disposable filter attached to a syringe up to commercial scale filters for use in manufacturing plants. The membrane filters are sterilized by autoclave or chemical sterilization. Validation of membrane filtration systems is performed following standardized protocols (Microbiological Evaluation of Filters for Sterilizing Liquids, Vol 4, No. 3. Washington, D.C: Health Industry Manufacturers Association, 1981) and involve challenging the membrane filter with a known quantity (ca. $10^7/cm^2$) of unusually small microorganisms, such as Brevundimonas diminuta (ATCC 19146).

Pharmaceutical compositions are optionally sterilized by passing through membrane filters. Formulations comprising nanoparticles (U.S. Pat. No. 6,139,870) or multilamellar vesicles (Richard et al., International Journal of Pharmaceutics (2006), 312(1-2):144-50) are amenable to sterilization by filtration through 0.22 µm filters without destroying their organized structure.

In some embodiments, the methods disclosed herein comprise sterilizing the formulation (or components thereof) by means of filtration sterilization. In ophthalmic gel compositions that includes thermosetting polymers, filtration is carried out below (e.g., about 5° C.) the gel temperature (Tgel) of a formulation described herein and with viscosity that allows for filtration in a reasonable time using a peristaltic pump (e.g., below a theoretical value of 100 cP).

Radiation Sterilization

One advantage of radiation sterilization is the ability to sterilize many types of products without heat degradation or other damage. The radiation commonly employed is beta radiation or alternatively, gamma radiation from a $^{60}Co$ source. The penetrating ability of gamma radiation allows its use in the sterilization of many product types, including solutions, compositions, and heterogeneous mixtures. The germicidal effects of irradiation arise from the interaction of gamma radiation with biological macromolecules. This interaction generates charged species and free-radicals. Subsequent chemical reactions, such as rearrangements and cross-linking processes, result in the loss of normal function for these biological macromolecules. The formulations described herein are also optionally sterilized using beta irradiation.

Sterilization by Heat

Many methods are available for sterilization by the application of high heat. One method is through the use of a saturated steam autoclave. In this method, saturated steam at a temperature of at least 121° C. is allowed to contact the object to be sterilized. The transfer of heat is either directly to the microorganism, in the case of an object to be sterilized, or indirectly to the microorganism by heating the bulk of an aqueous solution to be sterilized. This method is widely practiced as it allows flexibility, safety, and economy in the sterilization process.

Microorganisms

In some embodiments, the compositions are substantially free of microorganisms. Acceptable bioburden or sterility levels are based on applicable standards that define therapeutically acceptable compositions, including but not limited to United States Pharmacopeia Chapters <1111> et seq. For example, acceptable sterility (e.g., bioburden) levels include about 10 colony forming units (cfu) per gram of formulation, about 50 cfu per gram of formulation, about 100 cfu per gram of formulation, about 500 cfu per gram of formulation, or about 1000 cfu per gram of formulation. In some embodiments, acceptable bioburden levels or sterility for formulations include less than 10 cfu/mL, less than 50 cfu/mL, less than 500 cfu/mL, or less than 1000 cfu/mL microbial agents. In addition, acceptable bioburden levels or sterility include the exclusion of specified objectionable microbiological agents. By way of example, specified objectionable microbiological agents include but are not limited to Escherichia coli (E. coli), Salmonella sp., Pseudomonas aeruginosa (P. aeruginosa), and/or other specific microbial agents.

An important component of the sterility assurance quality control, quality assurance and validation process is the method of sterility testing. Sterility testing, by way of example only, is performed by two methods. The first is direct inoculation wherein a sample of the composition to be tested is added to growth medium and incubated for a period of time up to 21 days. Turbidity of the growth medium indicates contamination. Drawbacks to this method include the small sampling size of bulk materials which reduces sensitivity, and detection of microorganism growth based on a visual observation. An alternative method is membrane filtration sterility testing. In this method, a volume of product is passed through a small membrane filter paper. The filter paper is then placed into media to promote the growth of microorganisms. This method has the advantage of greater sensitivity as the entire bulk product is sampled. The commercially available Millipore Steritest sterility testing system is optionally used for determinations by membrane filtration sterility testing. For the filtration testing of creams or ointments Steritest filter system No. TLHVSL210 are used. For the filtration testing of emulsions or viscous products Steritest filter system No. TLAREM210 or TDAREM210 are used. For the filtration testing of pre-filled syringes Steritest filter system No. TTHASY210 are used. For the filtration testing of material dispensed as an aerosol or foam Steritest filter system No. TTHVA210 are used. For the filtration testing of soluble powders in ampoules or vials Steritest filter system No. TTHADA210 or TTHADV210 are used.

Testing for E. coli and Salmonella includes the use of lactose broths incubated at 30-35° C. for 24-72 hours, incubation in MacConkey and/or EMB agars for 18-24 hours, and/or the use of Rappaport medium. Testing for the detection of P. aeruginosa includes the use of NAC agar. United States Pharmacopeia Chapter <62> further enumerates testing procedures for specified objectionable microorganisms.

Ophthalmic Gel VAP-1 Composition

Gels have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

In some embodiments, gels are also classified as being hydrophobic or hydrophilic. In certain embodiments, the base of a non-limiting example of a hydrophobic gel includes a liquid paraffin with polyethylene or fatty oils gelled with colloidal silica, or aluminum or zinc soaps. In contrast, the base of a non-limiting example of a hydrophilic gel includes water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions disclosed herein is pseudo plastic, plastic, thixotropic, or dilatant.

In some embodiments, the ophthalmic composition is an ophthalmic gel, and wherein the ophthalmically acceptable carrier comprises water and at least one viscosity-enhancing agent. In some embodiments, the viscosity-enhancing agent is selected from cellulose-based polymers, polyoxyethylene-polyoxypropylene triblock copolymers, dextran-based polymers, polyvinyl alcohol, dextrin, polyvinylpyrrolidone, polyalkylene glycols, chitosan, collagen, gelatin, hyaluronic acid, or combinations thereof.

In some embodiment, the ophthalmic gel composition described herein is a semi-solid or is in a gelled state before it is topically administered (e.g., at room temperature). For example, suitable viscosity-enhancing agents for such gels include by way of example only, gelling agents and suspending agents. In one embodiment, the enhanced viscosity formulation does not include a buffer. In other embodiments, the enhanced viscosity formulation includes a pharmaceutically acceptable buffer. Sodium chloride or other tonicity agents are optionally used to adjust tonicity, if necessary.

By way of example only, the ophthalmically acceptable viscosity agent includes hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity enhancing agents compatible with the targeted ocular site include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethylcellulose (HPMC), sodium carboxymethyl-cellulose (CMC), silicon dioxide, polyvinylpyrrolidone (PVP: povidone), Splenda® (dextrose, maltodextrin and sucralose) or combinations thereof. In specific embodiments, the viscosity-enhancing excipient is a combination of MCC and CMC. In another embodiment, the viscosity-enhancing agent is a combination of carboxymethylated chitosan, or chitin, and alginate. The combination of chitin and alginate with the ophthalmic agents disclosed herein acts as a controlled release formulation, restricting the diffusion of the ophthalmic agents from the formulation. Moreover, the combination of carboxymethylated chitosan and alginate is optionally used to assist in increasing the permeability of the ophthalmic agents in the eye.

In some embodiments is an enhanced viscosity formulation, comprising from about 0.1 mM and about 100 mM of an ophthalmic agent, a pharmaceutically acceptable viscosity agent, and water for injection, the concentration of the viscosity agent in the water being sufficient to provide an enhanced viscosity formulation with a final viscosity from about 100 to about 100,000 cP. In certain embodiments, the viscosity of the gel is in the range from about 100 to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, about 15,000 cP to about 1,000,000 cP. In other embodiments, when an even more viscous medium is desired, the biocompatible gel comprises at least about 35%, at least about 45%, at least about 55%, at least about 65%, at least about 70%, at least about 75%, or even at least about 80% or so by weight of the ophthalmic agent. In highly concentrated samples, the biocompatible enhanced viscosity formulation comprises at least about 25%, at least about 35%, at least about 45%, at least about 55%, at least about 65%, at least about 75%, at least about 85%, at least about 90%, or at least about 95% or more by weight of the ophthalmic agent.

In one embodiment, the pharmaceutically acceptable enhanced viscosity ophthalmically acceptable formulation comprises at least one ophthalmic agent and at least one gelling agent. Suitable gelling agents for use in preparation of the gel formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, or methylcellulose), guar gum, xanthan gum, locust bean gum, alginates (e.g., alginic acid), silicates, starch, tragacanth, carboxyvinyl polymers, carrageenan, paraffin, petrolatum, and any combinations or mixtures thereof. In some other embodiments, hydroxypropylmethylcellulose (Methocel®) is utilized as the gelling agent. In certain embodiments, the viscosity enhancing agents described herein are also utilized as the gelling agent for the gel formulations presented herein.

In some embodiments, the ophthalmic gel composition described herein is an in situ gel formulation. In some instances, the in situ gel formation is based on increased pre-corneal residence time of the ophthalmic composition, which improves ocular bioavailability, corneal mucoadhesion, lysosomal interaction and ionic gelation, improved corneal absorption, thermal gelation, or a combination thereof. In some instances, the in situ gel formulation is activated by pH, temperature, ion, UV, or solvent exchange.

In some instances, the ophthalmic gel composition comprises a VAP-1 inhibitor and one or more gelling agents. In some instances, the gelling agent includes, but is not limited to, poloxamer (e.g. Poloxamer 407), tetronics, ethyl (hydroxyethyl) cellulose, cellulose acetate phthalate (CAP), carbopol (e.g. Carbopol 1342P NF, Carbopol 980 NF), alginates (e.g. low acetyl gellan gum (Gelrite®)), gellan, hyaluronic acid, pluronics (e.g. Pluronic F-127), chitosan, polyvinyl alcohol (PVA), polyvinylpyrrolidone (PVP), dextran, hydroxy propyl methyl cellulose (HPMC), hydroxyethylcellulose (HEC), methylcellulose (MC), thiolated xyloglucan, polymethacrilic acid (PMMA), polyethylene glycol (PEG), pseudolatexes, xyloglucans, or combinations thereof.

In some instances, the in situ gel formation further comprises a permeation enhancer. In some instances, the permeation enhancer includes surfactants (e.g. non-ionic surfactants), benzalkonium chloride, EDTA, surface-active heteroglycosides, calcium chelators, hydroxyl propyl beta cyclodextrin (HP beta CD), bile salts, and the like.

In some embodiments, other gel formulations are useful depending upon the particular ophthalmic agent, other pharmaceutical agent or excipients/additives used, and as such are considered to fall within the scope of the present disclosure. For example, other commercially-available glycerin-based gels, glycerin-derived compounds, conjugated, or crosslinked gels, matrices, hydrogels, and polymers, as well as gelatins and their derivatives, alginates, and alginate-based gels, and even various native and synthetic hydrogel and hydrogel-derived compounds are all expected to be useful in the ophthalmic agent formulations described herein. In some embodiments, ophthalmically acceptable gels include, but are not limited to, alginate hydrogels SAF®-Gel (ConvaTec, Princeton, N.J.), Duoderm® Hydroactive Gel (ConvaTec), Nu-gel® (Johnson & Johnson Medical, Arlington, Tex.); Carrasyn® (V) Acemannan Hydrogel (Carrington Laboratories, Inc., Irving, Tex.); glycerin gels Elta® Hydrogel (Swiss-American Products, Inc., Dallas, Tex.) and K-Y® Sterile (Johnson & Johnson). In further embodiments, biodegradable biocompatible gels also represent compounds present in ophthalmically acceptable formulations disclosed and described herein.

In some embodiments, the viscosity-enhancing agent is a cellulose-based polymer selected from cellulose gum, alkylcellulose, hydroxyl-alkyl cellulose, hydroxyl-alkyl alkylcellulose, carboxy-alkyl cellulose, or combinations thereof. In some embodiments, the viscosity-enhancing agent is hydroxyl-alkyl alkylcellulose. In some embodiment, the viscosity-enhancing agent is hydroxypropyl methylcellulose.

In certain embodiments, the enhanced viscosity formulation is characterized by a phase transition between room temperature and body temperature (including an individual with a serious fever, e.g., up to about 42° C.). In some embodiments, the phase transition occurs at 1° C. below body temperature, at 2° C. below body temperature, at 3° C. below body temperature, at 4° C. below body temperature, at 6° C. below body temperature, at 8° C. below body temperature, or at 10° C. below body temperature. In some embodiments, the phase transition occurs at about 15° C. below body temperature, at about 20° C. below body temperature or at about 25° C. below body temperature. In specific embodiments, the gelation temperature (Tgel) of a formulation described herein is about 20° C., about 25° C., or about 30° C. In certain embodiments, the gelation temperature (Tgel) of a formulation described herein is about 35° C., or about 40° C. Included within the definition of body temperature is the body temperature of a healthy individual, or an unhealthy individual, including an individual with a fever (up to ~42° C.). In some embodiments, the pharmaceutical compositions described herein are liquids at about room temperature and are administered at or about room temperature.

Copolymers polyoxypropylene and polyoxyethylene (e.g., polyoxyethylene-polyoxypropylene triblock copolymers) form thermosetting gels when incorporated into aqueous solutions. These polymers have the ability to change from the liquid state to the gel state at temperatures close to body temperature, therefore allowing useful formulations that are applied to the targeted ocular site. The liquid state-to-gel state phase transition is dependent on the polymer concentration and the ingredients in the solution.

In some embodiments, the amount of thermosetting polymer in any formulation described herein is about 10%, about 15%, about 20%, about 25%, about 30%, about 35% or about 40% of the total weight of the formulation. In some embodiments, the amount of thermosetting polymer in any formulation described herein is about 10%, about 11%, about 12%, about 13%, about 14%, about 15%, about 16%, about 17%, about 18%, about 19%, about 20%, about 21%, about 22%, about 23%, about 24% or about 25% of the total weight of the formulation. In some embodiments, the amount of thermosetting polymer (e.g., Poloxamer 407) in any formulation described herein is about 7.5% of the total weight of the formulation. In some embodiments, the amount of thermosetting polymer (e.g., Poloxamer 407) in any formulation described herein is about 10% of the total weight of the formulation. In some embodiments, the amount of thermosetting polymer (e.g., Poloxamer 407) in any formulation described herein is about 11% of the total weight of the formulation. In some embodiments, the amount of thermosetting polymer (e.g., Poloxamer 407) in any formulation described herein is about 12% of the total weight of the formulation. In some embodiments, the amount of thermosetting polymer (e.g., Poloxamer 407) in any formulation described herein is about 13% of the total weight of the formulation. In some embodiments, the amount of thermosetting polymer (e.g., Poloxamer 407) in any formulation described herein is about 14% of the total weight of the formulation. In some embodiments, the amount of thermosetting polymer (e.g., Poloxamer 407) in any formulation described herein is about 15% of the total weight of the formulation. In some embodiments, the amount of thermosetting polymer (e.g., Poloxamer 407) in any formulation described herein is about 16% of the total weight of the formulation. In some embodiments, the amount of thermosetting polymer (e.g., Poloxamer 407) in any formulation described herein is about 17% of the total weight of the formulation. In some embodiments, the amount of thermosetting polymer (e.g., Poloxamer 407) in any formulation described herein is about 18% of the total weight of the formulation. In some embodiments, the amount of thermosetting polymer (e.g., Poloxamer 407) in any formulation described herein is about 19% of the total weight of the formulation. In some embodiments, the amount of thermosetting polymer (e.g., Poloxamer 407) in any formulation described herein is about 20% of the total weight of the formulation. In some embodiments, the amount of thermosetting polymer (e.g., Poloxamer 407) in any formulation described herein is about 21% of the total weight of the formulation. In some embodiments, the amount of thermosetting polymer (e.g., Poloxamer 407) in any formulation described herein is about 23% of the total weight of the formulation. In some embodiments, the amount of thermosetting polymer (e.g., Poloxamer 407) in any formulation described herein is about 25% of the total weight of the formulation. In some embodiments, the amount of thickening agent (e.g., a gelling agent) in any formulation described herein is about 1%, about 5%, about 10%, or about 15% of the total weight of the formulation. In some embodiments, the amount of thickening agent (e.g., a gelling agent) in any formulation described herein is about 0.5%, about 1%, about 1.5%, about 2%, about 2.5%, about 3%, about 3.5%, about 4%, about 4.5%, or about 5% of the total weight of the formulation.

In an alternative embodiment, the thermogel is a PEG-PLGA-PEG triblock copolymer (Jeong et al., Nature (1997), 388:860-2; Jeong et al., J. Control. Release (2000), 63:155-63; Jeong et al., Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting coploymers are soluble in water and form a free-flowing liquid at room temperature, but form a hydrogel at body temperature. A commercially available PEG-PLGA-PEG triblock copolymer is RESOMER RGP t50106 manufactured by Boehringer Ingelheim. This material is composed of a PLGA copolymer of 50:50 poly(DL-lactide-co-glycolide) and is 10% w/w of PEG and has a molecular weight of about 6000.

Additional biodegradable thermoplastic polyesters include AtriGel® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly(DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt. % of the composition; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Since the polymer systems of thermosetting gels dissolve more completely at reduced temperatures, methods of solubilization include adding the required amount of polymer to the amount of water to be used at reduced temperatures. Generally after wetting the polymer by shaking, the mixture is capped and placed in a cold chamber or in a thermostatic container at about 0-10° C. in order to dissolve the polymer. The mixture is stirred or shaken to bring about a more rapid dissolution of the thermosetting gel polymer. The ophthalmic agent and various additives such as buffers, salts, and preservatives are subsequently added and dissolved. In some instances the pharmaceutically agent is suspended if it is insoluble in water. The pD is modulated by the addition of appropriate buffering agents.

Ophthalmic Ointment VAP-1 Inhibitor Composition

An ointment is a homogeneous, viscous, semi-solid preparation, most commonly a greasy, thick oil (e.g., oil 80%-water 20%) with a high viscosity, intended for external application to the skin or mucous membranes. Ointments have a water number that defines the maximum amount of water that it contains. They are used as emollients or for the application of active ingredients to the skin for protective, therapeutic, or prophylactic purposes and where a degree of occlusion is desired. Ointments are used topically on a variety of body surfaces including the mucous membranes of the eye (an eye ointment).

The vehicle of an ointment is known as the ointment base. The choice of a base depends upon the clinical indication for the ointment. The different types of ointment bases are: hydrocarbon bases, e.g. hard paraffin, soft paraffin, microcrystalline wax and ceresine; absorption bases, e.g., wool fat, beeswax; water soluble bases, e.g., macrogols 200, 300, 400; emulsifying bases, e.g., emulsifying wax, cetrimide; vegetable oils, e.g., olive oil, coconut oil, sesame oil, almond oil, and peanut oil.

Ointments are formulated using hydrophobic, hydrophilic, or water-emulsifying bases to provide preparations that are immiscible, miscible, or emulsifiable with skin secretions. In some embodiments, they are also derived from hydrocarbon (fatty), absorption, water-removable, or water-soluble bases. The active agents are dispersed in the base, and later they get divided after the drug penetration into the target sites (e.g., membranes, etc.).

The present disclosure recognizes that it is sometimes difficult to incorporate into the ointment a drug of low concentration with sufficient dose-to-dose uniformity for effectively treating a disorder or disease. In some embodiments, poly(ethylene-glycols), polyethoxylated castor oils (Cremophor® EL), alcohols having 12 to 20 carbon atoms or a mixture of two or more of said components are effective excipients for dispersing and/or dissolving effective amounts of ophthalmic drugs, in particular of ascomycins and staurosporine derivatives, in an ointment base, in particular in an ointment base substantially comprising oleaginous and hydrocarbon components, and that the resulting ointments are excellently tolerated by the skin and by ocular tissue.

The present disclosure further recognizes that ophthalmic drugs, such as a VAP-1 inhibitor, incorporated in the ointment compositions describes herein target the choroid and/or retina in a patient when the compositions are topically administered to the ocular surface, in particular to the sclera of said patient. In some embodiments, an ophthalmic ointment composition includes an ophthalmic drug, an ointment base, and an agent for dispersing and/or dissolving said drug in the ointment base, selected from a poly(ethylene-glycol), a polyethoxylated castor oil, an alcohol having 12 to 20 carbon atoms, and a mixture of two or more of said components.

In some embodiments, the ointment bases include ophthalmically acceptable oil and fat bases, such as natural wax, e.g., white and yellow bees wax, carnauba wax, wool wax (wool fat), purified lanolin, anhydrous lanolin; petroleum wax, e.g., hard paraffin, microcrystalline wax; hydrocarbons, e.g., liquid paraffin, white and yellow soft paraffin, white petrolatum, yellow petrolatum; or combinations thereof.

The above mentioned oil and fat bases are described in more detail, for instance, in the British Pharmacopoeia, Edition 2001, or the European Pharmacopoeia, $3^{rd}$ Edition.

In some embodiments, the ointment base is present in amounts of about 50 to about 95, preferably of 70 to 90% by weight based on the total weight of the composition.

A preferred ointment base comprises a combination of one or more of one or more natural waxes like those indicated above, preferably wool wax (wool fat), and one or more hydrocarbons like those indicated above, preferably a soft paraffin or a petrolatum, more preferably in combination with liquid paraffin.

A special embodiment of the aforementioned ointment base comprises, e.g., 5 to 17 parts by weight of wool fat, and 50 to 65 parts by weight of white petrolatum as well as 20 to 30 parts by weight of liquid paraffin.

In some embodiments, the agent for dispersing and/or dissolving the ophthalmic drug in the ointment base is selected from a poly(ethylene-glycol), a polyethoxylated castor oil, an alcohol having 12 to 20 carbon atoms, and a mixture of two or more of said components. The agent is preferably used in amounts of 1 to 20 percent, more preferably 1 to 10 percent by weight of the entire semisolid ophthalmic composition.

Alcohols having 12 to 20 carbon atoms include particularly stearyl alcohol ($C_{18}H_{37}OH$), cetyl alcohol ($C_{16}H_{33}OH$) and mixtures thereof. Preferred are so-called cetostearyl alcohols, mixtures of solid alcohols substantially consisting of stearyl and cetyl alcohol and preferably comprising not less than 40 percent by weight of stearyl alcohol and a sum of stearyl alcohol and cetyl alcohol amounting to at least 90 percent by weight, and compositions comprising not less than 80 percent by weight of cetylstearyl alcohol and an emulsifier, in particular sodium cetostearyl sulfate and/or sodium lauryl sulfate, preferably in amounts not less than 7 percent by weight of emulsifier.

Polyethoxylated castor oils are reaction products of natural or hydrogenated castor oils and ethylene glycol. In some instances, such products are obtained in known manner, e.g. by reaction of a natural or hydrogenated castor oil or fractions thereof with ethylene oxide, e.g. in a molar ratio of from about 1:30 to about 1:60, with optional removal of free polyethylene glycol components from the product, e.g. in accordance with the methods disclosed in German Auslegeschriften 1,182,388 and 1,518,819. Especially suitable and preferred is a product commercially available under the trade name Cremophor® EL having a molecular weight (by steam osmometry)=ca. 1630, a saponification no.=ca. 65-70, an acid no.=ca. 2, an iodine no.=ca. 28-32 and an nD 25=ca.1.471. Also suitable for use in this category is, for instance, Nikkol® HCO-60, a reaction product of hydrogenated castor oil and ethylene oxide exhibiting the following characteristics: acid no.=ca. 0.3; saponification no.=ca. 47.4; hydroxy value=ca. 42.5. pH (5%)=ca. 4.6; Color APHA=ca. 40; m.p.=ca. 36.0° C.; Freezing point=ca. 32.4° C.; $H_2O$ content (%, KF)=ca. 0.03.

Poly(ethylene-glycols) are used in some embodiments as the agent for dispersing and/or dissolving the ophthalmic drug in the ointment base according to the present disclosure. Suitable poly(ethylene-glycol)s are typically mixtures of polymeric compounds of the general formula $H-(OCH_2-CH_2)_nOH$, wherein the index n typically range from 4 to 230 and the mean molecular weight from about 200 to about 10000. Preferably n is a number from about 6 to about 22 and the mean molecular weight between about 300 and about 1000, more preferably n ranges from about 6 to about 13 and the mean molecular weight from about 300 to about 600, most preferably n has a value of about 8.5 to about 9 and the relative molecular weight is about 400. Suitable poly(ethylene-glycols) are readily available commercially, for example poly(ethylene-glycols) having a mean molecular weight of about 200, 300, 400, 600, 1000, 1500, 2000, 3000, 4000, 6000, 8000, and 10000.

The poly(ethylene-glycols), in particular the preferred types described in the foregoing paragraph, are preferably used in amounts of 1 to 10, more preferably 1 to 5 percent by weight of the entire semisolid ophthalmic composition.

An especially preferred embodiment of the compositions according to the instant disclosure comprises an agent for dispersing and/or dissolving of the drug in the ointment base which is selected from a poly(ethylene-glycol), a polyethoxylated castor oil and preferably a mixture of said components.

Gel/Ointment Viscosity

In some embodiments, the composition has a Brookfield RVDV viscosity of from about 10,000 to about 300,000 cps at about 20° C. and sheer rate of 1 $s^{-1}$. In some embodiments, the composition has a Brookfield RVDV viscosity of from about 15,000 to about 200,000 cps at about 20° C. and sheer rate of 1 $s^{-1}$. In some embodiments, the composition has a Brookfield RVDV viscosity of from about 50,000 to about 150,000 cps at about 20° C. and sheer rate of 1 $s^{-1}$. In some embodiments, the composition has a Brookfield RVDV viscosity of from about 70,000 to about 130,000 cps at about 20° C. and sheer rate of 1 $s^{-1}$. In some embodiments, the composition has a Brookfield RVDV viscosity of from about 90,000 to about 110,000 cps at about 20° C. and sheer rate of 1 $s^{-1}$.

In some embodiments, the ophthalmic gel formulation contains a viscosity enhancing agent sufficient to provide a viscosity of between about 500 and 1,000,000 centipoise; between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise. In some embodiments, the ophthalmic gel formulation contains a viscosity enhancing agent sufficient to provide a viscosity of between about 50,0000 and 1,000,000 centipoise.

In some embodiments, the compositions described herein are low viscosity compositions at body temperature. In some embodiments, low viscosity compositions contain from about 1% to about 10% of a viscosity-enhancing agent (e.g., gelling components such as polyoxyethylene-polyoxypropylene copolymers). In some embodiments, low viscosity compositions contain from about 2% to about 10% of a viscosity-enhancing agent (e.g., gelling components such as polyoxyethylene-polyoxypropylene copolymers). In some embodiments, low viscosity compositions contain from about 5% to about 10% of a viscosity enhancing agent (e.g., gelling components such as polyoxyethylene-polyoxypropylene copolymers). In some embodiments, low viscosity compositions are substantially free of a viscosity enhancing agent (e.g., gelling components such as polyoxyethylene-polyoxypropylene copolymers). In some embodiments, a low viscosity ophthalmic agent composition described herein provides an apparent viscosity of from about 100 cP to about 10,000 cP. In some embodiments, a low viscosity ophthalmic agent composition described herein provides an apparent viscosity of from about 500 cP to about 10,000 cP. In some embodiments, a low viscosity ophthalmic agent composition described herein provides an apparent viscosity of from about 1000 cP to about 10,000 cP.

In some embodiments, the compositions described herein are viscous compositions at body temperature. In some embodiments, viscous compositions contain from about 10% to about 25% of a viscosity-enhancing agent (e.g., gelling components such as polyoxyethylene-polyoxypropylene copolymers). In some embodiments, the viscous compositions contain from about 14% to about 22% of a viscosity-enhancing agent (e.g., gelling components such as polyoxyethylene-polyoxypropylene copolymers). In some embodiments, the viscous compositions contain from about 15% to about 21% of a viscosity-enhancing agent (e.g., gelling components such as polyoxyethylene-polyoxypropylene copolymers). In some embodiments, a viscous ophthalmic composition described herein provides an apparent viscosity of from about 100,000 cP to about 1,000,000 cP. In some embodiments, a viscous ophthalmic composition described herein provides an apparent viscosity of from about 150,000 cP to about 500,000 cP. In some embodiments, a viscous ophthalmic composition described herein provides an apparent viscosity of from about 250,000 cP to about 500,000 cP. In some of such embodiments, a viscous ophthalmic composition is a liquid at room temperature and gels at about between room temperature and body temperature (including an individual with a serious fever, e.g., up to about 42° C.). In some embodiments, a viscous ophthalmic composition is administered as monotherapy for treatment of an ophthalmic disease or condition described herein.

In some embodiments, the viscosity of the gel formulations presented herein is measured by any means described. For example, in some embodiments, an LVDV-II+CP Cone Plate Viscometer and a Cone Spindle CPE-40 is used to calculate the viscosity of the gel formulation described herein. In other embodiments, a Brookfield (spindle and cup) viscometer is used to calculate the viscosity of the gel formulation described herein. In some embodiments, the viscosity ranges referred to herein are measured at room temperature. In other embodiments, the viscosity ranges referred to herein are measured at body temperature (e.g., at the average body temperature of a healthy human).

Gel/Ointment Dose-To-Dose Uniformity

Typical ophthalmic gels are packaged in eye drop bottles and administered as drops. For example, a single administration (i.e., a single dose) of an ophthalmic gel includes a single drop, two drops, three drops or more into the eyes of the patient. Furthermore, typical ophthalmic ointments are packaged in tubes or other squeezable containers with a dispensing nozzle through which strips of the ointment are delivered. For example, a single administration (i.e., a single dose) of an ophthalmic ointment includes a single strip, or multiple strips into the eyes of the patient. In some embodiments, one dose of the ophthalmic gel described herein is one drop of the gel composition from the eye drop bottle. In some embodiments, one dose of the ophthalmic ointment is one strip of the ointment composition dispensed through the nozzle of a dispersing tube.

In some cases, described herein include ophthalmic gel compositions which provide a dose-to-dose uniform concentrations. In some instances, the dose-to-dose uniform concentration does not present significant variations of drug content from one dose to another. In some instances, the dose-to-dose uniform concentration does provide consistent drug content from one dose to another.

In some cases, described herein include ophthalmic ointment compositions, which provide a dose-to-dose uniform concentrations. In some instances, the dose-to-dose uniform concentration does not present significant variations of drug content from one dose to another. In some instances, the dose-to-dose uniform concentration does provide consistent drug content from one dose to another.

In some embodiments, the composition has a dose-to-dose ophthalmic agent concentration variation of less than 50%. In some embodiments, the composition has a dose-to-dose ophthalmic agent concentration variation of less than 40%. In some embodiments, the composition has a dose-to-dose ophthalmic agent concentration variation of less than 30%. In some embodiments, the composition has a dose-to-dose ophthalmic agent concentration variation of less than 20%. In some embodiments, the composition has a dose-to-dose ophthalmic agent concentration variation of less than 10%. In some embodiments, the composition has a dose-to-dose ophthalmic agent concentration variation of less than 5%.

In some embodiments, the dose-to-dose ophthalmic agent concentration variation is based on 10 consecutive doses. In some embodiments, the dose-to-dose ophthalmic agent concentration variation is based on 8 consecutive doses. In some embodiments, the dose-to-dose ophthalmic agent concentration variation is based on 5 consecutive doses. In some embodiments, the dose-to-dose ophthalmic agent concentration variation is based on 3 consecutive doses. In some embodiments, the dose-to-dose ophthalmic agent concentration variation is based on 2 consecutive doses.

In some embodiments, the ophthalmic gel compositions and ophthalmic ointment compositions described herein are "no-shake" formulations.

In some embodiments, the composition is stored in a plastic container. In some embodiments, the material of the plastic container comprises low-density polyethylene (LDPE).

The compounds (e.g., VAP-1 inhibitor) contemplated by the present disclosure may be in the form of any other suitable pharmaceutical composition currently known or developed in the future.

IV. Methods of Use

Inhibition of Vascular Adhesion Protein-1

VAP-1 is a therapeutic target for the treatment of vascular and inflammatory-related diseases. Approaches to inhibit VAP-1 include, but are not limited to, small interfering RNAs, function blocking antibodies, and small molecule inhibitors. Clinical trials using orally administered VAP-1 inhibitors have been conducted and have been shown to be safe. Examples of VAP-1 inhibitors include, but are not limited to ASP8232, BTT-1029, PXS-4728A, BTT-1023, LJP-1207, LJP-1586, SZE5302, antibody 7-88, BTT-2052, PXS-4681A, PXS-4159A, BTT-2027, mofegiline hydrochloride, aminohexoses, hydrazine derivatives, propenyl- and propargylamines, 4-substituted-2-butynylamines, haloallylamines, pyrroline derivatives, propargyldiamines, allylamines, diamines, 4,5,6,7-tetrahydroimidazo[4,5-c]pyridine derivatives, thiocarbamoyl derivatives, carboxamides, sulfonamides, thiazole and/or guanidine derivatives, oxime derivatives, dihydrazine, arylalkylamines, oxazolidinones, haloalkylamines, benfotiamine, and imidazopyridine derivatives.

Uveitis is a general term describing a group of inflammatory diseases that produces swelling and destroys eye tissues. The term "uveitis" is used because the diseases often affect a part of the eye called the uvea. Nevertheless, uveitis is not limited to the uvea. These diseases also affect the lens, retina, optic nerve, and vitreous, producing reduced vision or blindness. Common symptoms of uveitis include decreased vision, pain, light sensitivity, and increased floaters.

The uvea is the middle layer of the eye which contains much of the eye's blood vessels. This is one way that inflammatory cells can enter the eye. Located between the sclera, the white outer coat of the eye, and the inner layer of the eye, called the retina, the uvea consists of the iris, ciliary body, and choroid. Uveitis disrupts vision by primarily causing problems with the lens, retina, optic nerve, and vitreous. Specific types of Uveitis, classified by where it occurs in the eye, include, anterior uveitis, intermediate uveitis, posterior uveitis, and panuveitis uveitis.

Uveitis is primarily caused by inflammatory responses inside the eye. Exemplary inflammatory responses that lead to uveitis include an attack from the body's own immune system, infections or tumors occurring within the eye or in other parts of the body, bruises to the eye, and toxins that may penetrate the eye.

Diagnosis of uveitis may include a thorough examination and the recording of the patient's complete medical history. Laboratory tests may be done to rule out an infection or an autoimmune disorder. A central nervous system evaluation is often be performed on patients with a subgroup of intermediate uveitis, called pars planitis, to determine whether they have multiple sclerosis which is often associated with pars planitis. Exemplary eye exams used, include, an eye chart or visual acuity test which measures whether a patient's vision has decreased, a funduscopic exam where the pupil is dilated with eye drops and then a light is shown through with an instrument called an ophthalmoscope to noninvasively inspect the back, inside part of the eye, measurement of ocular pressure, and a slit lamp exam which non-invasively inspects much of the eye.

Uveitis treatments primarily try to eliminate inflammation, alleviate pain, prevent further tissue damage, and restore any loss of vision. Treatments depend on the type of uveitis a patient displays.

Treatment can also depend on the specific type of uveitis the patient is suffering from. Anterior uveitis is treated, for example, by taking eye drops that dilate the pupil to prevent muscle spasms in the iris and ciliary body or by taking eye drops to reduce inflammation. Intermediate, posterior, and pan-uveitis are often treated with injections around the eye, medications given by mouth, or, in some instances, time-release capsules that are surgically implanted inside the eye.

In an aspect, is provided a method of inhibiting vascular adhesion protein-1 (VAP-1), the method comprising contacting VAP-1 with a compound, comprising structural Formula (IV), (IV-A), (IV-B), (V-A), (V-B), (VI-A), (VI-B), (VII-A), and/or (VII-B) or an alkene isomer, tautomer, or an isotopic variant thereof, or a pharmaceutically acceptable salt, solvate, hydrate, or prodrug thereof. In an aspect is provided a method of inhibiting vascular adhesion protein-1 (VAP-1), comprising contacting VAP-1 with a pharmaceutical composition including a compound of structural Formula (IV), (IV-A), (IV-B), (V-A), (V-B), (VI-A), (VI-B), (VII-A), and/or (VII-B) or an alkene isomer, tautomer, or an isotopic variant thereof, or a pharmaceutically acceptable salt, solvate, hydrate, or prodrug thereof, and at least one pharmaceutically acceptable excipient.

In an aspect, there is provided a method of treating or preventing a disease or disorder mediated by VAP-1, comprising administering to a subject in need thereof a therapeutically effective amount of a compound, comprising structural Formula (IV), (IV-A), (IV-B), (V-A), (V-B), (VI-A), (VI-B), (VII-A), and/or (VII-B) or an alkene isomer, tautomer, or an isotopic variant thereof; or a pharmaceutically acceptable salt, solvate, hydrate, or prodrug thereof is provided. In an aspect is provided a method of treating or preventing a disease or disorder mediated by VAP-1, comprising administering to a subject in need thereof a therapeutically effective amount of a pharmaceutical composition including a compound of structural Formula (IV), (IV-A), (IV-B), (V-A), (V-B), (VI-A), (VI-B), (VII-A), and/or (VII-B) or an alkene isomer, tautomer, or an isotopic variant thereof; or a pharmaceutically acceptable salt, solvate, hydrate, or prodrug thereof, and at least one pharmaceutically acceptable excipient.

In an aspect, there is provided a method of treating or preventing an ophthalmic disease or disorder in a subject in need thereof, comprising administering to the subject a therapeutically effective amount of a compound of structural Formula (IV), (IV-A), (IV-B), (V-A), (V-B), (VI-A), (VI-B), (VII-A), and/or (VII-B) or an alkene isomer, tautomer, or an isotopic variant thereof; or a pharmaceutically acceptable salt, solvate, hydrate, or prodrug thereof is provided. In an aspect is provided a method of treating or preventing an ophthalmic disease or disorder in a subject in need thereof, comprising administering to the subject a therapeutically effective amount of a pharmaceutical composition including a compound of structural Formula (IV), (IV-A), (IV-B), (V-A), (V-B), (VI-A), (VI-B), (VII-A), and/or (VII-B) or an alkene isomer, tautomer, or an isotopic variant thereof, or a pharmaceutically acceptable salt, solvate, hydrate, or prodrug thereof, and at least one pharmaceutically acceptable excipient.

In some embodiments, the disease or disorder mediated by VAP-1 is uveitis. In some embodiments, the ophthalmic disease or disorder is uveitis. In some embodiments, the compounds or compositions disclosed herein are administered topically.

The compounds of the present disclosure may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the $ED_{50}$ is commonly used as a measure of reasonable expectance of an agent's effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

In addition, an effective dose of the compounds of the present disclosure may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In some embodiments, the compounds contemplated by the present disclosure may be administered (e.g., orally) at dosage levels of about 0.01 mg/kg to about 1000 mg/kg, or about 1 mg/kg to about 100 mg/kg, of subject body weight per day, one, two, three, four or more times a day, to obtain the desired therapeutic effect. For administration of an oral agent, the compositions can be provided in the form of tablets, capsules and the like containing from 0.05 to 1000 milligrams of the active ingredient, particularly 0.05, 0.1, 0.25, 0.5, 0.75, 1.0, 1.25, 1.5, 1.75, 2.0, 2.5, 5.0, 7.5, 10.0, 15.0, 20.0, 25.0, 50.0, 75.0, 100.0, 125.0, 150.0, 175.0, 200.0, 250.0, 300.0, 400.0, 500.0, 600.0, 750.0, 800.0, 900.0, and 1000.0 milligrams of the active ingredient. A pharmaceutically acceptable carrier(s), diluent(s) and/or excipient(s) may be present in an amount of from about 0.1 g to about 10 g.

In some embodiments, the dosage of the desired compound is contained in a "unit dosage form." The phrase "unit dosage form" refers to physically discrete units, each unit including a predetermined amount of the compound (e.g., VAP-1 inhibitor), sufficient to produce the desired effect. It will be appreciated that the parameters of a unit dosage form will depend on the particular agent and the effect to be achieved.

In some embodiments, the ophthalmic composition is formulated as an ophthalmic solution for the treatment of uveitis.

In some embodiments, disclosed herein is a method of arresting uveitis development that comprises administering to an eye of an individual in need thereof an effective amount of an ophthalmic composition described herein. In some embodiments, described herein is a method of arresting or preventing uveitis development, comprising administering to an eye of an individual in need thereof an effective amount of an ophthalmic composition comprising from about 0.001 wt % to about 50 wt % of a VAP-1 compound. In some embodiments, the ophthalmic composition is administered at predetermined time intervals over an extended period of time. In some embodiments, the ophthalmic composition is administered once every day. In some embodiments, the ophthalmic composition is administered every other day. In some embodiments, the ophthalmic composition is administered over 1 week, 2 weeks, 1 month, 2 months, 3 months, 6 months, 1 year, 2 years, 3 years, 4 years, 5 years, 6 years, 7 years, 8 years, 9 years, 10 years, 11 years, or 12-15 years.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. Examples

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Identification of VAP-1 Inhibitors

In some embodiments, compounds described herein possess at least one property or characteristic that is of therapeutic relevance. Candidate inhibitors may be identified by using, for example, an art-accepted assay or model. The Example section described assay(s) that were used to determine the VAP-1 inhibitory activity of the compounds described herein, as well as assays that could be used to evaluate one or more characteristics of the compounds; the skilled artisan is aware of other procedures, assay formats, and the like that can be employed to generate data and information useful to assess the VAP-1 inhibitors described herein.

After identification, candidate inhibitors can be further evaluated by using techniques that provide data regarding characteristics of the inhibitors (e.g., pharmacokinetic parameters). Comparisons of the candidate inhibitors to a reference standard (which may the "best-of-class" of current inhibitors) are indicative of the potential viability of such candidates. VAP-1 inhibitors that can serve as reference or benchmark compounds include those shown to demonstrate desired activity and characteristics. Other means of analyzing candidate inhibitors will be apparent to the skilled artisan.

Synthesis Details

The following general schemes represent synthetic methods that may be used in the preparation of the compounds of the present disclosure, as well as common chemical intermediates generated in the preparation thereof. The skilled artisan will recognize that these schemes are representative only, and that in many instances alternative synthetic means may be employed.

The following examples are put forth so as to provide those of ordinary skill in the art with a complete disclosure and description of how to make and use the present disclosure, and are not intended to limit the scope of what the inventors regard as their disclosure, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; psi=pounds per square inch; HPLC=high performance liquid chromatography; BW=body weight; U=unit; ns=not statistically significant; HATU=(1-[Bis(dimethylamino)methylene]-1H-1,2,3-triazolo[4,5-b]pyridinium 3-oxid hexafluorophosphate); TFA=trifluoroacetic acid; MBTE=methyl t-butyl ether; DCM=dichloromethane; PBS=phosphate-buffered saline; IHC=immunohistochemistry; DMSO=dimethylsulfoxide; EtOAc=ethyl acetate; EtOH=ethanol; DMEM=Dulbeco's Modification of Eagle's Medium; EDTA=ethylenediaminetetraacetic acid; Me=methyl; Et=ethyl; S—singlet; D—doublet; dd—doublet of doublet; m—multiplet.

General Preparation of the Hydrazine Starting Material:

General Experimental Procedure A: BBr$_3$ Mediated Demethylation

To a stirring solution of a (hetero)aryl methoxy (1 eq) in DCM was added BBr$_3$ (3 eq). The reaction was stirred for 1 hr at 18° C. MeOH was added and the volatiles were removed under reduced pressure. The residue obtained was partitioned between sat. aq. NaHCO$_3$ and EtOAc, the layers were separated, the aqueous phase was washed with EtOAc, combined organics were dried over Na$_2$SO$_4$, filtered and concentrated under reduced pressure to afford the desired product.

General Experimental Procedure B: Alkylation with Fluoro Allylic Amine

To a stirring solution of a (hetero)aryl alcohol (1.1 eq) in DMF was added K$_2$CO$_3$ (1.2 eq) followed by tert-butyl (2-(bromomethyl)-3-fluoroallyl)carbamate (1 eq). The reaction was stirred at 70° C. for 15 hr. The mixture was filtered, the filtrate was concentrated under reduced pressure and the crude residue obtained was purified by automated flash column chromatography to afford the desired product.

General Experimental Procedure C: HCl Mediated Boc Deprotection/TsOH Salt Formation To an N-Boc amine was added 4M HCl in dioxane. The reaction was stirred for 15 hr at 18° C. The volatiles were removed under reduced pressure, the residue obtained was passed free based with SCX-2 and purified by automated flash column chromatography. To the residue obtained 1 eq or 2 eq of p-toluenesulfonic acid (tosylic acid or TsOH) in MeOH (2 mL) was added and the solvent was removed under reduced pressure to afford the desired product.

General Experimental Procedure D: 6,5-Heteroaromatic Ring Formation with Alpha-Bromo-Ketone To a stirring solution of heteroarylamine (1 eq) in EtOH was added an alpha bromo-ketone (1.2 eq). The solution was heated to 80° C. for 1.5 hr. The reaction was worked up; the solvent was removed under reduced pressure, the residue was dissolved in DCM, washed with sat. NaHCO$_3$, brine, dried over Na$_2$SO$_4$, filtered and concentrated under reduced pressure. The crude residue obtained was purified by automated flash column chromatography to the desire product.

General Experimental Procedure E part 1: N-Amination with O-(mesitylsulfonyl)hydroxylamine To a suspension of heteroaryl amine (1 eq) in DCM was added portion wise O-(mesitylsulfonyphydroxylamine (2 eq), keeping the temperature below 22° C. The suspension was stirred for 15 hr at 18° C. The solids were filtered off and washed with DCM. The residue was dried under reduced pressure at 18° C. to afford the desired product.

General Experimental Procedure E part 2: 6,5-Heteroaromatic Ring Formation with Valeroyl Chloride To a mixture of N-amino heteroaryl amine (1 eq) in pyridine was added valeroyl chloride (2 eq). The mixture was stirred at 100° C. under nitrogen overnight. The mixture was concentrated in vacuo and the residue was stirred in a mixture of sat. aq. Na$_2$CO$_3$ and DCM. After 1 hr, the aqueous layer was extracted with DCM. The combined organic layers were dried over Na$_2$SO$_4$, filtered and concentrated under reduced pressure. The residue obtained was purified by automated flash column chromatography to the desired product.

LCMS

The instrument employed was the Agilent 1290 series with UV detector and HP 6130 MSD mass detector equipped with a Waters XBridge BEH C18 XP (2.1×50 mm, 2.5 μm) column. The mass detector the employed atmosphere pressure ionization via electrospray for both positive and negative conjugates.

LCMS Method "28817C TFA LCMS-5 C-3.M"
The method employed was as follows:
Mobile phase A: Trifluoroacetic acid (aq; 0.05%)
Mobile phase B: Acetonitrile
Pump Flow: 0.6 ml/min
UV Detection: 215, 268 nm
Injection Volume: 0.2 μl
Run Time: 3.5 min
Column Temperature: 35° C.
Pump Program: Gradient

| Time (min) | % A | % B |
|---|---|---|
| 0.0 | 95 | 5 |
| 0.5 | 95 | 5 |
| 2.5 | 10 | 90 |

LCMS Method "General 3"
Mobile phase A: 10 mM NH4Ac in a 20:1, water:MeCN solution
Mobile phase B: MeCN
Pump Flow: 0.6 ml/min
UV Detection: 215, 268 nm Injection Volume: 0.2 μl
Run Time: 3.0 min
Column Temperature: 30° C.
Pump Program: Gradient

| Time (min) | % A | % B |
|---|---|---|
| 0.0 | 80 | 20 |
| 1.5 | 5 | 95 |
| 2.5 | 5 | 95 |
| 2.6 | 80 | 20 |

LCMS Method "General 4"
Mobile phase A: 10 mM NH4Ac in a 20:1, water:MeCN solution
Mobile phase B: MeCN
Pump Flow: 0.6 ml/min
UV Detection: 215, 268 nm
Injection Volume: 0.2 μl
Run Time: 3.0 min
Column Temperature: 30° C.
Pump Program: Gradient

| Time (min) | % A | % B |
|---|---|---|
| 0.0 | 95 | 5 |
| 1.5 | 5 | 95 |
| 2.5 | 5 | 95 |
| 2.6 | 95 | 5 |

LCMS Method "General+–"
The method employed was as follows:
Mobile phase A: Trifluoroacetic acid (aq; 0.05%)
Mobile phase B: Acetonitrile
Pump Flow: 1 ml/min
UV Detection: 220, 254 nm
Injection Volume: 5 μl
Run Time: 24 min
Column Temperature: 35° C.
Pump Program: Gradient

| Time (min) | % A | % B |
|---|---|---|
| 0.0 | 90 | 10 |
| 15.0 | 30 | 70 |
| 17.0 | 5 | 95 |
| 20.0 | 5 | 95 |
| 20.01 | 90 | 10 |
| 24.0 | 90 | 10 |

Exemplary Compounds

Example 1

(E)-2-(((2-butylimidazo[1,2-a]pyridin-6-yl)oxy)methyl)-3-fluoroprop-2-en-1-amine bis(4-methylbenzenesulfonate)

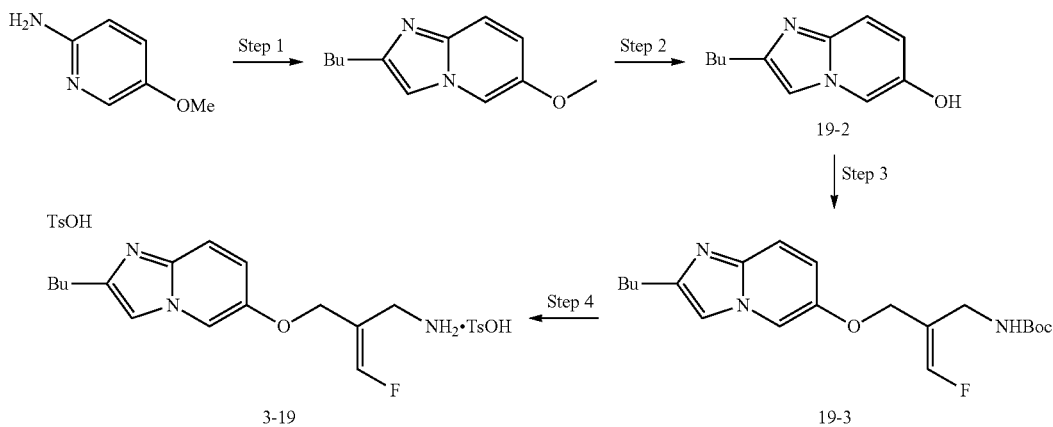

Step 1. 2-butyl-6-methoxyimidazo[1,2-a]pyridine was prepared according to General Experimental Procedure D. 5-methoxypyridin-2-amine (500 mg, 4.03 mmol) gave 2-butyl-6-methoxyimidazo[1,2-a]pyridine (760 mg, 40%) as a yellow oil. LCMS (General 3) RT: 0.89 min; Yield: 75%; m/z 205.1 (M+H$^+$).

Step 2. 2-butylimidazo[1,2-a]pyridin-6-ol was prepared according to General Experimental Procedure A. 2-butyl-6-methoxyimidazo[1,2-a]pyridine (1.25 g, 6.12 mmol) gave 2-butylimidazo[1,2-a]pyridin-6-ol (870 mg, 70%) as an off-white solid. LCMS (General 3) RT: 0.60 min; Yield: 88%; m/z 191.4 (M+H$^+$).

Step 3. tert-butyl (E)-(2-(((2-butylimidazo[1,2-a]pyridin-6-yl)oxy)methyl)-3-fluoroallyl)carbamate was prepared according to General Experimental Procedure B. 2-butylimidazo[1,2-a]pyridin-6-ol (181 mg, 0.95 mmol) gave tert-butyl (E)-(2-(((2-butylimidazo[1,2-a]pyridin-6-yl)oxy)methyl)-3-fluoroallyl)carbamate (192 mg, 53%) as a light yellow oil. LCMS (General 3) RT: 1.18 min; Yield: 66%; m/z 378.1 (M+H$^+$).

Step 4. (E)-2-(((2-butylimidazo[1,2-a]pyridin-6-yl)oxy)methyl)-3-fluoroprop-2-en-1-amine bis(4-methylbenzenesulfonate) was prepared according to General Experimental Procedure C. tert-butyl (E)-(2-(((2-butylimidazo[1,2-a]pyridin-6-yl)oxy)methyl)-3-fluoroallyl)carbamate (192 mg, 0.51 mmol) gave (E)-2-(((2-butylimidazo[1,2-a]pyridin-6-yl)oxy)methyl)-3-fluoroprop-2-en-1-amine bis(4-methylbenzenesulfonate) (73 mg, 23%) as a beige solid. LCMS: (28817C TFA LCMS-5 C-3.M) RT: 1.230 min; Yield: 94.2%; m/z 278.2 (M+H$^+$). $^1$H NMR (300 MHz, DMSO-d$_6$) δ 8.35 (d, J=2.3 Hz, 1H), 8.10 (s, 3H), 7.70 (s, 1H), 7.55-7.43 (m, 4H), 7.29-7.00 (m, 3H), 4.58 (d, J=3.5 Hz, 2H), 3.62 (d, J=2.2 Hz, 2H), 2.67 (t, J=7.6 Hz, 2H), 2.26 (s, 3H), 1.63 (p, J=7.5 Hz, 2H), 1.32 (q, J=7.4 Hz, 2H), 0.89 (t, J=7.3 Hz, 3H).

Example 2

(E)-2-(((2-butylimidazo[1,2-a]pyridin-7-yl)oxy)methyl)-3-fluoroprop-2-en-1-amine 4-methylbenzenesulfonate imidazo[1,2-a]pyridin-7-yl)oxy)methyl)-3-fluoroallyl)carbamate (140 mg, 0.37 mmol) gave (E)-2-(((2-butylimidazo[1,2-a]pyridin-7-yl)oxy)methyl)-3-fluoroprop-2-en-1-amine 4-methylbenzenesulfonate (64 mg, 38%) as a beige solid. LCMS: (28817C TFA LCMS-5 C-3.M) RT: 1.323 min; Yield: 93.3%; m/z 278.2 (M+H$^+$). $^1$H NMR (300 MHz, DMSO-d$_6$) δ 8.35 (d, J=7.5 Hz, 1H), 8.05 (s, 3H), 7.63-7.38 (m, 3H), 7.33-6.86 (m, 4H), 6.65 (dd, J=7.5, 2.5 Hz, 1H), 4.65 (d, J=3.5 Hz, 2H), 3.61 (s, 2H), 2.61 (t, J=7.5 Hz, 2H), 2.26 (s, 3H), 1.61 (p, J=7.5 Hz, 2H), 1.32 (q, J=7.4 Hz, 2H), 0.88 (t, J=7.3 Hz, 3H).

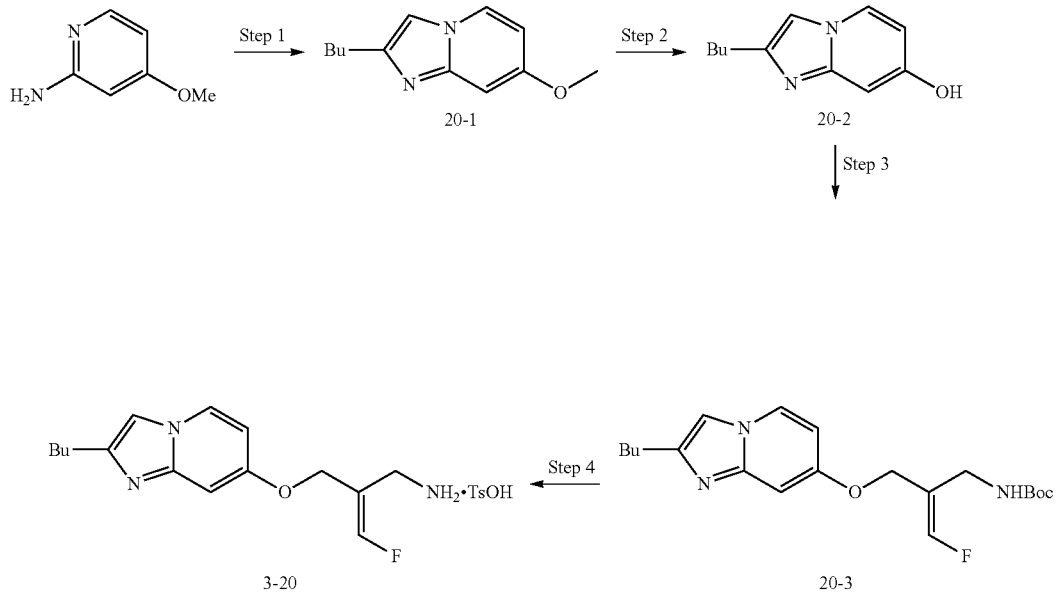

Step 1. 2-butyl-7-methoxyimidazo[1,2-a]pyridine was prepared according to General Experimental Procedure D. 4-methoxypyridin-2-amine (500 mg, 4.03 mmol) gave 2-butyl-7-methoxyimidazo[1,2-a]pyridine (760 mg, 40%) as a yellow oil. LCMS (General 3) RT: 0.82 min; Yield: 75%; m/z 205.2 (M+H$^+$).

Step 2. 2-butylimidazo[1,2-a]pyridin-7-ol was prepared according to General Experimental Procedure A. 2-butyl-7-methoxyimidazo[1,2-a]pyridine (760 mg, 3.72 mmol) gave 2-butylimidazo[1,2-a]pyridin-7-ol (167 mg, 24%) as an off-white solid. LCMS (General 3) RT: 0.49 min; Yield: 64%; m/z 191.4 (M+H$^+$).

Step 3. tert-butyl (E)-(2-(((2-butylimidazo[1,2-a]pyridin-7-yl)oxy)methyl)-3-fluoroallyl)carbamate was prepared according to General Experimental Procedure B. 2-butylimidazo[1,2-a]pyridin-7-ol (167 mg, 0.87 mmol) gave tert-butyl (E)-(2-(((2-butylimidazo[1,2-a]pyridin-7-yl)oxy)methyl)-3-fluoroallyl)carbamate (140 mg, 43%) as a light yellow oil. LCMS (General 3) RT: 1.17 min; Yield: 79%; m/z 378.2 (M+H$^+$). Step 4. (E)-2-(((2-butylimidazo[1,2-a]pyridin-7-yl)oxy)methyl)-3-fluoroprop-2-en-1-amine 4-methylbenzenesulfonate was prepared according to General Experimental Procedure C. tert-butyl (E)-(2-(((2-butyl-

Example 3

(E)-2-(((2-butyl-[1,2,4]triazolo[1,5-a]pyridin-7-yl)oxy)methyl)-3-fluoroprop-2-en-1-amine 4-methylbenzenesulfonate

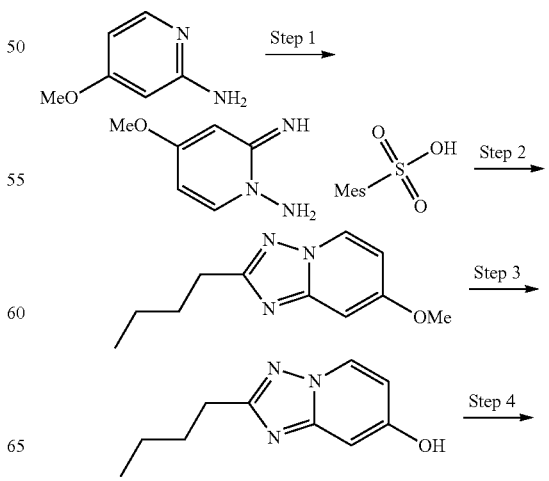

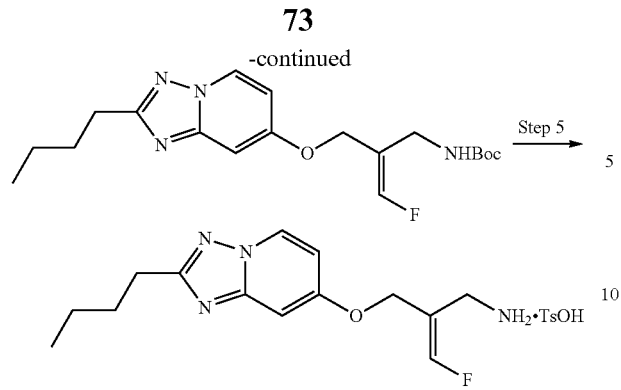

Yield: 98%; m/z 279.2 (M+H⁺). ¹H NMR (299 MHz, Methanol-d₄) δ 8.56 (d, J=7.5 Hz, 1H), 7.77-7.62 (m, 2H), 7.29 (d, J=80.7 Hz, 1H), 7.26-7.18 (m, 2H), 7.12 (d, J=2.6 Hz, 1H), 6.92 (dd, J=7.5, 2.6 Hz, 1H), 4.79-4.73 (m, 2H), 3.88-3.82 (m, 2H), 2.86 (t, J=7.6 Hz, 2H), 2.36 (s, 3H), 1.80 (q, J=7.6 Hz, 2H), 1.51-1.35 (m, 2H), 0.97 (t, J=7.4 Hz, 3H).

Example 4

(E)-2-(((2-butyl-[1,2,4]triazolo[1,5-a]pyridin-6-yl)oxy)methyl)-3-fluoroprop-2-en-1-amine 4-methylbenzenesulfonate

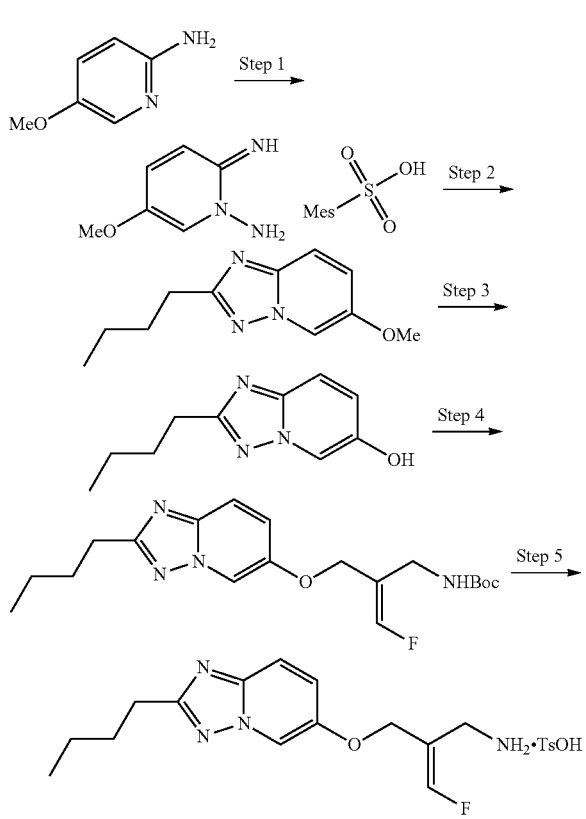

Step 1. 2-imino-4-methoxypyridin-1(2H)-amine 2,4,6-trimethylbenzenesulfonate was prepared according to General Experimental Procedure E part 1. To a suspension of 2-amino-4-methoxypyridine (0.75 g, 6.06 mmol) in DCM (35 mL) was added portion wise O-(mesitylsulfonyl)hydroxylamine (2.8 g, 2 eq, 12.1 mmol), keeping the temperature below 22° C. The suspension was stirred for 15 hr at 18° C. The solids were filtered off and washed with DCM (40 mL). The residue was dried under reduced pressure at 18° C. to afford 2-imino-4-methoxypyridin-1(2H)-amine 2,4,6-trimethylbenzenesulfonate (1.84 g, 43%) as a white solid. LCMS (General 3) RT: 0.41 min; Yield: 80%; m/z 140.4 (M+H⁺).

Step 2. 2-butyl-7-methoxy-[1,2,4]triazolo[1,5-a]pyridine was prepared according to General Experimental Procedure E part 2. To a mixture of 2-imino-4-methoxypyridin-1(2H)-amine 2,4,6-trimethylbenzenesulfonate (1.84 g, 5.18 mmol) in pyridine (21 mL) was added valeroyl chloride (1.24 mL, 2 eq, 10.4 mmol). The mixture was stirred at 100° C. under a nitrogen for 15 hr. The mixture was concentrated under reduced pressure and the residue was stirred in a mixture of sat. aq. Na₂CO₃ (20 mL) and DCM (20 mL). After 1 h the aqueous layer was extracted with DCM (2×20 mL). The combined organic layers were dried over Na₂SO₄, filtered and concentrated to give 0.70 g dark red solid. The residue was purified by automated flash column chromatography to afford 2-butyl-7-methoxy-[1,2,4]triazolo[1,5-a]pyridine (325 mg, 31%) as a white solid. LCMS (General 3) RT: 0.80 min; Yield: 95%; m/z 206.4 (M+H⁺).

Step 3. 2-butyl-[1,2,4]triazolo[1,5-a]pyridin-7-ol was prepared according to General Experimental Procedure A. 2-butyl-7-methoxy-[1,2,4]triazolo[1,5-a]pyridine (470 mg, 2.3 mmol) gave 2-butyl[1,2,4]triazolo[1,5-a]pyridin-7-ol (291 mg, 66%) as an off-white solid. LCMS (General 3) RT: 0.57 min; Yield: 99%; m/z 192.4 (M+H⁺).

Step 4. tert-butyl (E)-(2-(((2-butyl-[1,2,4]triazolo[1,5-a]pyridin-7-yl)oxy)methyl)-3-fluoroallyl)carbamate was prepared according to General Experimental Procedure B. 2-butyl-[1,2,4]triazolo[1,5-a]pyridin-7-ol (291 mg, 1.52 mmol) gave tert-butyl (E)-(2-(((2-butyl-[1,2,4]triazolo[1,5-a]pyridin-7-yl)oxy)methyl)-3-fluoroallyl)carbamate (405 mg, 70%) as a white solid. LCMS (General 3) RT: 1.14 min; Yield: 86%; m/z 379.3 (M+H⁺).

Step 5. (E)-2-(((2-butyl-[1,2,4]triazolo[1,5-a]pyridin-7-yl)oxy)methyl)-3-fluoroprop-2-en-1-amine 4-methylbenzenesulfonate was prepared according to General Experimental Procedure C. tert-butyl (E)-(2-(((2-butyl-[1,2,4]triazolo[1,5-a]pyridin-7-yl)oxy)methyl)-3-fluoroallyl)carbamate (405 mg, 1.07 mmol) gave (E)-2-(((2-butyl-[1,2,4]triazolo[1,5-a]pyridin-7-yl)oxy)methyl)-3-fluoroprop-2-en-1-amine 4-methylbenzenesulfonate (158 mg, 32%) as an off-white solid. LCMS (28817C TFA LCMS-5 C-3M) RT: 1.37 min;

Step 1. 2-imino-5-methoxypyridin-1(2H)-amine 2,4,6-trimethylbenzenesulfonate was prepared according to General Experimental Procedure E part 1. 2-amino-5-methoxypyridine (0.75 g, 6.06 mmol) gave 2-imino-5-methoxypyridin-1(2H)-amine 2,4,6-trimethylbenzenesulfonate (383 mg, 13%) as an off-white solid. LCMS (General 3) RT: 0.32 min; Yield: 76%; m/z 140.4 (M+H⁺).

Step 2. 2-butyl-6-methoxy-[1,2,4]triazolo[1,5-a]pyridine was prepared according to General Experimental Procedure E part 2. 2-imino-5-methoxypyridin-1(2H)-amine 2,4,6-trimethylbenzenesulfonate (265 mg, 0.781 mmol) gave 2-butyl-6-methoxy-[1,2,4]triazolo[1,5-a]pyridine (39 mg, 24%) as a white solid. LCMS (General 3) RT: 0.82 min; Yield: 88%; m/z 206.2 (M+H⁺).

Step 3. 2-butyl[1,2,4]triazolo[1,5-a]pyridin-6-ol was prepared according to General Experimental Procedure A. 2-butyl-6-methoxy-[1,2,4]triazolo[1,5-a]pyridine (1.25 g, 6.09 mmol) gave 2-butyl[1,2,4]triazolo[1,5-a]pyridin-6-ol (0.69 g, 59%) as a white solid. LCMS (General 3) RT: 0.59 min; Yield: 99%; m/z 192.3 (M+H⁺).

Step 4. Tert-butyl (E)-(2-(((2-butyl-[1,2,4]triazolo[1,5-a]pyridin-6-yl)oxy)methyl)-3-fluoroallyl)carbamate was prepared according to General Experimental Procedure B. 2-butyl-[1,2,4]triazolo[1,5-a]pyridin-6-ol (250 mg, 1.31 mmol) gave tert-butyl (E)-(2-(((2-butyl-[1,2,4]triazolo[1,5-a]pyridin-6-yl)oxy)methyl)-3-fluoroallyl)carbamate (454 mg, 92%) as a yellow oil. LCMS (General 3) RT: 1.15 min; Yield: 97%; m/z 379.3 (M+H+).

Step 5. (E)-2-(((2-butyl-[1,2,4]triazolo[1,5-a]pyridin-6-yl)oxy)methyl)-3-fluoroprop-2-en-1-amine 4-methylbenzenesulfonate was prepared according to General Experimental Procedure C. tert-butyl (E)-(2-(((2-butyl-[1,2,4]triazolo[1,5-a]pyridin-6-yl)oxy)methyl)-3-fluoroallyl)carbamate (454 mg, 1.20 mmol) gave (E)-2-(((2-butyl-[1,2,4]triazolo[1,5-a]pyridin-6-yl)oxy)methyl)-3-fluoroprop-2-en-1-amine 4-methylbenzenesulfonate (156 mg, 29%) as an off-white solid. LCMS (28817C TFA LCMS-5 C-3.M) RT: 1.39 min; Yield: 96%; m/z 279.2 (M+H+). $^1$H NMR (299 MHz, Chloroform-d) δ 8.01 (s, 1H), 7.54 (dd, J=9.6, 0.8 Hz, 1H), 6.77 (d, 1H), 4.72 (s, 1H), 4.44 (dd, J=3.7, 1.1 Hz, 2H), 4.09-3.95 (m, 2H), 2.93-2.83 (m, 2H), 1.93-1.75 (m, 2H), 1.54-1.35 (m, 11H), 0.96 (t, J=7.3 Hz, 3H).

Example 5

(Z)-2-(((2-butylimidazo[1,2-a]pyridin-6-yl)oxy)methyl)-3-fluoroprop-2-en-1-amine 4-methylbenzenesulfonate methoxyimidazo[1,2-a]pyridine (1.75 g, 6.12 mmol) gave 2-butylimidazo[1,2-a]pyridin-6-ol (870 mg, 70%) as an off-white solid. LCMS (General 3) RT: 0.60 min; Yield: 88%; m/z 191.4 (M+H+).

Step 3. Tert-butyl (Z)-(2-(((2-butylimidazo[1,2-a]pyridin-6-yl)oxy)methyl)-3-fluoroallyl)carbamate was prepared according to General Experimental Procedure B. 2-butyl-imidazo[1,2-a]pyridin-6-ol (178 mg, 0.94 mmol) gave tert-butyl (Z)-(2-(((2-butylimidazo[1,2-a]pyridin-6-yl)oxy)methyl)-3-fluoroallyl)carbamate (65 mg, 18%) as a brown oil. LCMS (General 3) RT: 1.19 min; Yield: 82%; m/z 378.4 (M+H+).

Step 4. (Z)-2-(((2-butylimidazo[1,2-a]pyridin-6-yl)oxy)methyl)-3-fluoroprop-2-en-1-amine 4-methylbenzenesulfonate was prepared according to General Experimental Procedure C. tert-butyl (Z)-(2-(((2-butylimidazo[1,2-a]pyridin-6-yl)oxy)methyl)-3-fluoroallyl)carbamate (65 mg, 0.17 mmol) gave (Z)-2-(((2-butylimidazo[1,2-a]pyridin-6-yl)oxy)methyl)-3-fluoroprop-2-en-1-amine 4-methylbenzenesulfonate (17.5 mg, 23%) as a brown oil. LCMS: (28817C TFA LCMS-5 C-3.M) RT: 1.35 min; Yield: 88.9%; m/z 278.2 (M+H+). $^1$H NMR (300 MHz, DMSO-d$_6$) δ 8.24 (d, J=2.3 Hz, 1H), 7.76-7.53 (m, 3H), 7.46 (d, J=8.1 Hz, 2H), 7.42-7.27 (m, 2H), 7.15-6.93 (m, 4H), 4.66 (d, J=2.7 Hz, 2H), 3.52 (d, J=3.0 Hz, 2H), 2.62 (t, J=7.6 Hz, 2H), 2.27 (s, 3H), 1.68-1.56 (m, 2H), 1.32 (q, J=7.4 Hz, 2H), 0.89 (t, J=7.3 Hz, 3H)

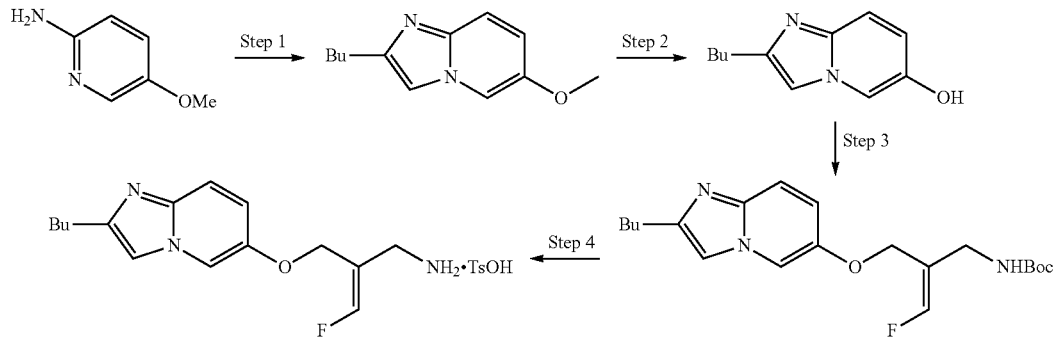

Step 1. 2-butyl-6-methoxyimidazo[1,2-a]pyridine was prepared according to General Experimental Procedure D. 5-methoxypyridin-2-amine (1.0 g, 8.05 mmol) gave 2-butyl-6-methoxyimidazo[1,2-a]pyridine (1.42 g, 72%) as an orange oil. LCMS (General 3) RT: 0.89 min; Yield: 75%; m/z 205.1 (M+H+).

Step 2. 2-butylimidazo[1,2-a]pyridin-6-ol was prepared according to General Experimental Procedure A. 2-butyl-6-

Example 6

((E)-2-(((2-butylpyrazolo[1,5-a]pyridin-6-yl)oxy)methyl)-3-fluoroprop-2-en-1-amine bis(4-methylbenzenesulfonate)

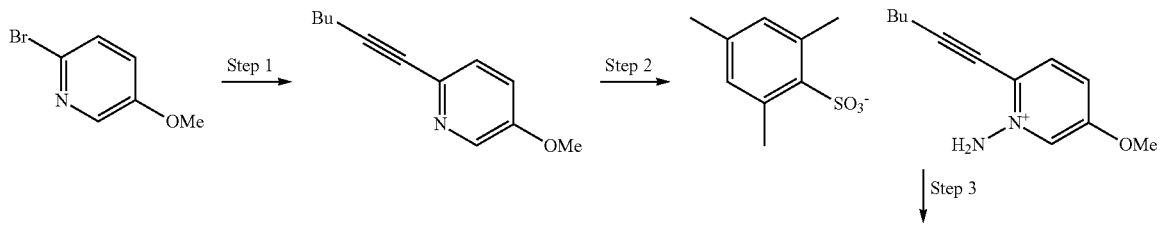

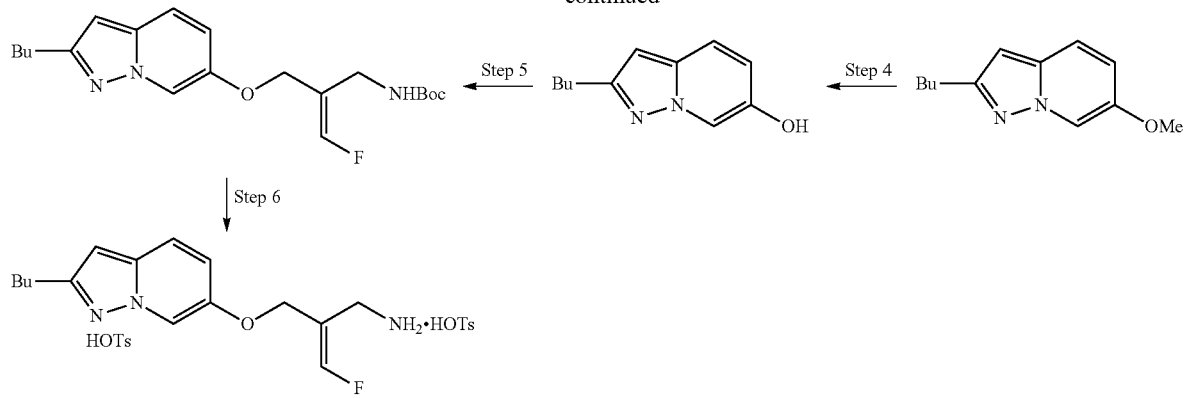

Step 1. 2-(hex-1-yn-1-yl)-5-methoxypyridine was prepared according to the following procedure. A stirring solution of 2-bromo-5-methoxypyridine (1.88 g, 1 eq, 10 mmol), [(Ph$_3$P)$_2$PdCl$_2$] (351 mg, 0.05 eq, 50 μmol) and copper(I) iodide (190 mg, 0.1 eq, 1.0 mmol) in MeCN (50 mL) was sparged with N$_2$ for 30 min. hex-1-yne (1.64 g, 2.30 mL, 2.0 eq, 20 mmol) and NEt$_3$ (4.2 mL, 3.0 eq, 30 mmol) were added and the reaction was heated at 60° C. for 16 hr. The reaction was concentrated under reduced pressure and purified by automated flash column chromatography to afford t2-(hex-1-yn-1-yl)-5-methoxypyridine as a brown oil (1.60 g, 85%). LCMS (General 3) RT: 1.21 min; Yield: 98.9%; m/z 190.3 (M+H$^+$). $^1$H NMR (300 MHz, Chloroform-d) δ 8.25-8.20 (m, 1H), 7.33-7.23 (m, 1H), 7.10 (dd, J=8.6, 3.0 Hz, 1H), 3.85 (s, 3H), 2.41 (t, J=7.0 Hz, 2H), 1.66-1.40 (m, 4H), 0.93 (t, J=7.2 Hz, 3H).

Step 2. 1-amino-2-(hex-1-yn-1-yl)-5-methoxypyridin-1-ium 2,4,6-trimethylbenzenesulfonate was prepared according to the following procedure. To a stirring solution of 2-(hex-1-yn-1-yl)-5-methoxypyridine (1.60 g, 1 eq, 8.5 mmol) dissolved in DCM (17 mL) cooled to 0° C. was added O-(mesitylsulfonyl)hydroxylamine (2.18 g, 1.2 eq, 10.1 mmol) suspended in DCM (40 mL). The mixture was stirred at 0° C. for 2.5 hr then Et$_2$O (228 mL, 4V) was added. The resulting solid was filtered, the feed was washed with Et$_2$O (57 mL), air dried and then vacuum dried to afford 1-amino-2-(hex-1-yn-1-yl)-5-methoxypyridin-1-ium 2,4,6-trimethylbenzenesulfonate as an off-white solid (2.21 g, 65%). LCMS (General 3) RT: 0.40 min; Yield: 21.5%; m/z 199.4 (M−H)$^−$; RT=0.60, Yield: 78.5%; m/z 205.4 (M+H$^+$). $^1$H NMR (299 MHz, Chloroform-d) δ 9.44 (d, J=2.4 Hz, 1H), 7.53 (d, J=9.1 Hz, 1H), 7.39 (dd, J=9.1, 2.4 Hz, 1H), 6.83 (s, 2H), 4.11 (s, 3H), 2.71 (s, 6H), 2.60 (t, J=7.1 Hz, 2H), 2.23 (s, 3H), 1.73-1.60 (m, 2H), 1.56-1.39 (m, 2H), 0.97 (t, J=7.3 Hz, 3H).

Step 3. 2-butyl-6-methoxypyrazolo[1,5-a]pyridine was prepared according to the following procedure. A solution of 1-amino-2-(hex-1-yn-1-yl)-5-methoxypyridin-1-ium 2,4,6-trimethylbenzenesulfonate (2.21 g, 1 eq, 5.46 mmol) in acetic acid (15.6 mL, 50 eq, 273 mmol) was stirred at 80° C. for 16 hr. The reaction mixture was concentrated under reduced pressure, diluted with EtOAc (55 mL), and washed with sat. NaHCO$_3$ satd. (2×11 mL) and brine (11 mL), dried over Na$_2$SO$_4$, filtered and concentrated under reduced pressure to afford 2-butyl-6-methoxypyrazolo[1,5-a]pyridine (1.07 g, 95.9%) as a dark red oil. LCMS (General 3) RT: 1.25 min; Yield: 100%; m/z 205.4 (M+H$^+$). $^1$H NMR (299 MHz, Chloroform-d) δ 7.99 (dt, J=2.1, 0.8 Hz, 1H), 7.28 (dd, J=9.6, 0.8 Hz, 1H), 6.85 (dd, J=9.6, 2.2 Hz, 1H), 6.21 (s, 1H), 3.79 (s, 3H), 2.83-2.73 (m, 2H), 1.72 (tt, J=7.6, 6.4 Hz, 2H), 1.50 1.34 (m, 2H), 0.95 (t, J=7.3 Hz, 3H).

Step 4. 2-butylpyrazolo[1,5-a]pyridin-6-ol was prepared according to General Experimental Procedure A. 2-butyl-6-methoxypyrazolo[1,5-a]pyridine gave 2-butylpyrazolo[1,5-a]pyridin-6-ol as a brown solid (993 mg, 97%). LCMS (General 3) RT: 0.97 min; Yield: 94.4%; m/z 191.4, m/z 189.4 (M−H)$^−$. $^1$H NMR (300 MHz, Chloroform-d) δ 7.87 (dt, J=2.0, 1.0 Hz, 1H), 7.16 (dd, J=9.5, 0.8 Hz, 1H), 6.77 (dd, J=9.5, 2.0 Hz, 1H), 6.14 (d, J=0.8 Hz, 1H), 2.78-2.68 (m, 2H), 1.75-1.60 (m, 2H), 1.45-1.30 (m, 2H), 0.90 (t, J=7.3 Hz, 3H).

Step 5. tert-butyl (E)-(2-(((2-butylpyrazolo[1,5-a]pyridin-6-yl)oxy)methyl)-3-fluoroallyl)carbamate was prepared according to General Experimental Procedure B. 2-butylpyrazolo[1,5-a]pyridin-6-ol gave tert-butyl (E)-(2-(((2-butylpyrazolo[1,5-a]pyridin-6-yl)oxy)methyl)-3-fluoroallyl)carbamate (98 mg, 47%) as a pale yellow wax. LCMS (General 3) RT: 1.46 min; Yield: 90.8%; m/z 378.3 (M+H$^+$). $^1$H NMR (299 MHz, Chloroform-d) δ 8.04-7.99 (m, 1H), 7.31 (dd, J=9.5, 0.8 Hz, 1H), 6.91-6.84 (m, 1H), 6.76 (d, J=81.8 Hz, 1H), 6.23 (s, 1H), 4.74 (s, 1H), 4.40 (dd, J=3.7, 1.1 Hz, 2H), 4.06-3.96 (m, 2H), 2.84-2.72 (m, 2H), 1.79-1.65 (m, 2H), 1.50-1.34 (m, 11H), 0.95 (t, J=7.3 Hz, 3H). $^{19}$F NMR (282 MHz, Chloroform-d) δ-127.57 (d, J=82.3 Hz).

Step 6. ((E)-2-(((2-butylpyrazolo[1,5-a]pyridin-6-yl)oxy)methyl)-3-fluoroprop-2-en-1-amine bis(4-methylbenzenesulfonate) was prepared according to General Experimental Procedure C. Tert-butyl (E)-(2-(((2-butylpyrazolo[1,5-a]pyridin-6-yl)oxy)methyl)-3-fluoroallyl)carbamate gave ((E)-2-(((2-butylpyrazolo[1,5-a]pyridin-6-yl)oxy)methyl)-3-fluoroprop-2-en-1-amine bis(4-methylbenzenesulfonate) (77 mg, 53%) as a white solid. LCMS (28817C TFA LCMS-5 C-3.M) RT: 1.76 min; Yield: 98.2%; m/z 278.1 (M+H$^+$). $^1$H NMR (300 MHz, DMSO-d$_6$) δ 8.43-8.35 (m, 1H), 7.99 (s, 3H), 7.53-7.16 (m, 6H), 7.13-7.06 (m, 4H), 7.00 (dd, J=9.6, 2.2 Hz, 1H), 6.32 (s, 1H), 4.58 (d, J=3.8 Hz, 2H), 3.69-3.54 (m, 2H), 2.69 (t, J=7.6 Hz, 2H), 2.27 (s, 6H), 1.71-1.55 (m, 2H), 1.41-1.25 (m, 2H), 0.89 (t, J=7.3 Hz, 3H). $^{19}$F NMR (282 MHz, DMSO-d$_6$) δ-122.07 (d, J=82.1 Hz).

Example 7

(E)-2-(((2-butylimidazo[1,2-b]pyridazin-6-yl)oxy)methyl)-3-fluoroprop-2-en-1-amine 4-methylbenzenesulfonate

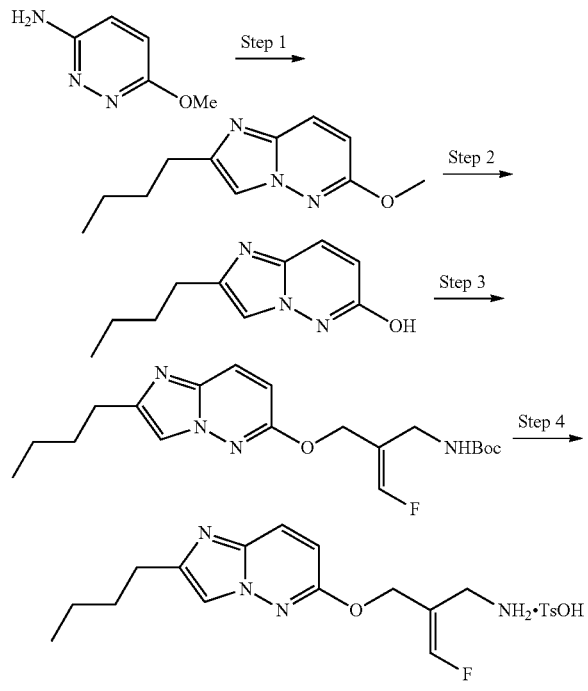

Step 1. 2-butyl-6-methoxyimidazo[1,2-b]pyridazine was prepared according to General Experimental Procedure D. To a stirring solution of 6-methoxypyridazin-3-amine (428 mg, 1 eq, 3.42 mmol) in EtOH (20 mL) was added 1-bromohexan-2-one (735 mg, 1.2 eq, 4.10 mmol). The solution was heated to 80° C. for 1.5 hr. The reaction was worked up; the solvent was removed under reduced pressure, the residue was dissolved in DCM (20 mL), washed with sat. NaHCO₃ (10 mL), brine (10 mL), dried over Na₂SO₄, filtered and concentrated under reduced pressure. The crude residue obtained was purified by automated flash column chromatography to afford 2-butyl-6-methoxyimidazo[1,2-b]pyridazine (384 mg, 55%) as a colorless oil. LCMS (General 3) RT: 1.07 min; Yield: 98%; m/z 206.2 (M+H⁺).

Step 2. 2-butylimidazo[1,2-b]pyridazin-6-ol was prepared according to General Experimental Procedure A. 2-butyl-6-methoxyimidazo[1,2-b]pyridazine (171 mg, 0.83 mmol) gave 2-butylimidazo[1,2-b]pyridazin-6-ol (137 mg, 86%) as a brown oil. LCMS (General 3) RT: 0.64 min; Yield: 74%; m/z 190.4 (M+H⁺).

Step 3. tert-butyl (E)-(2-(((2-butylimidazo[1,2-b]pyridazin-6-yl)oxy)methyl)-3-fluoroallyl)carbamate was prepared according to General Experimental Procedure B. 2-butylimidazo[1,2-b]pyridazin-6-ol (89 mg, 0.47 mmol) gave tert-butyl (E)-(2-(((2-butylimidazo[1,2-b]pyridazin-6-yl)oxy)methyl)-3-fluoroallyl)carbamate (89 mg, 50%) as a yellow oil. ¹H NMR (300 MHz, Chloroform-d) δ 7.69 (d, J=9.6 Hz, 1H), 7.49 (s, 1H), 6.80 (d, J=82.1 Hz, 1H), 6.60 (d, J=9.6 Hz, 1H), 4.85-4.66 (m, 3H), 4.08-3.89 (m, 3H), 2.76 (t, J=7.7 Hz, 2H), 1.82-1.63 (m, 3H), 1.53-1.32 (m, 13H), 0.95 (t, J=7.3 Hz, 3H).

Step 4. (E)-2-(((2-butylimidazo[1,2-b]pyridazin-6-yl)oxy)methyl)-3-fluoroprop-2-en-1-amine 4-methylbenzenesulfonate was prepared according to General Experimental Procedure C.

tert-butyl (E)-(2-(((2-butylimidazo[1,2-b]pyridazin-6-yl)oxy)methyl)-3-fluoroallyl)carbamate (89 mg, 0.24 mmol) gave (E)-2-(((2-butylimidazo[1,2-b]pyridazin-6-yl)oxy)methyl)-3-fluoroprop-2-en-1-amine 4-methylbenzenesulfonate (36.8 mg, 35%) as an orange solid. LCMS: (28817C TFA LCMS-5 C-3.M) RT: 1.299 min; Yield: 88.45%; m/z 279.20 (M+H⁺), ¹H NMR (300 MHz, DMSO-d₆) δ 8.15 (d, J=10.4 Hz, 2H), 8.00 (s, 3H), 7.60-7.25 (m, 3H), 7.16 (d, J=9.7 Hz, 1H), 7.09 (d, J=7.9 Hz, 3H), 4.88 (d, J=3.5 Hz, 2H), 3.67 (d, J=6.3 Hz, 4H), 2.74 (t, J=7.3 Hz, 3H), 2.27 (s, 5H), 1.66 (p, J=7.6 Hz, 2H), 1.41-1.25 (m, 3H), 0.90 (t, J=7.3 Hz, 3H)

Example 8

(E)-2-(((2-butylpyrazolo[1,5-a]pyridin-5-yl)oxy)methyl)-3-fluoroprop-2-en-1-amine bis(4-methylbenzenesulfonate)

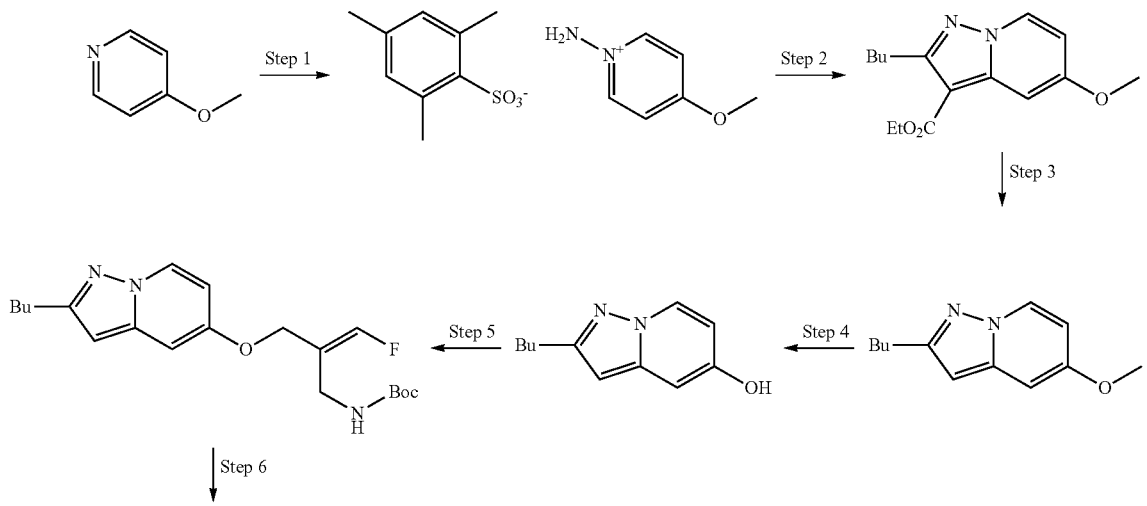

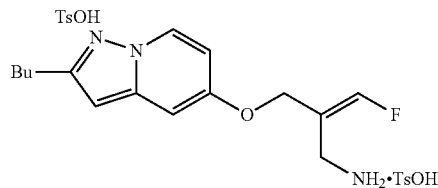

Step 1. 1-amino-4-methoxypyridin-1-ium 2,4,6-trimethylbenzenesulfonate was prepared according to the following procedure. To a stirring solution of 4-methoxypyridine (1.09 g, 1 eq, 10 mmol) in DCM (20 mL) cooled to 0° C. was slowly added O-(mesitylsulfonyl)hydroxylamine (2.58 g, 1.2 eq, 12 mmol) suspended in DCM (24 mL). The mixture was stirred for 3 hr at 0° C., then extra MesSO$_3$NH$_2$ (0.65 g) in DCM (6 mL) was added and the mixture was stirred for 2.5 days. Et$_2$O (200 mL, 4V) was added; a white paste separated. The liquid layer was decanted, the paste was washed with Et$_2$O (50 mL) and vacuum dried to afford crude 1-amino-4-methoxypyridin-1-ium 2,4,6-trimethylbenzenesulfonate (3.51 g, 45%). Purity determined by H NMR: 42%. $^1$H NMR (300 MHz, DMSO-d$_6$) δ 8.63-8.57 (m, 2H), 7.35-7.29 (m, 2H), 6.71 (s, 2H), 4.04 (s, 3H), 2.53 (s, 6H), 2.14 (s, 3H).

Step 2. Ethyl 2-butyl-5-methoxypyrazolo[1,5-a]pyridine-3-carboxylate was prepared according to the following procedure. 1-amino-4-methoxypyridin-1-ium 2,4,6-trimethylbenzenesulfonate (3.51 g, 1 Eq, 4.5 mmol) was dissolved in anhydrous DMF (15.5 mL) then ethyl hept-2-ynoate (1.9 g, 2.1 mL, 2.7 Eq, 12 mmol) and potassium carbonate (1.7 g, 2.7 Eq, 12 mmol) were successively added. The mixture was stirred at 100° C. overnight. Additional ethyl hept-2-ynoate (2.8 g, 3.1 mL, 4.0 Eq, 18 mmol) was added and the mixture for stirred at 100° C. for another day. No further reaction was observed by HPLC. The mixture was allowed to cool to room temperature, then it was treated with water (62 mL, 4V), brine (16 mL) and extracted with AcOEt (4×62 mL). The organic layers were washed with water/brine 1:1 (2×62 mL), brine (62 mL), dried on Na2SO4, filtered and evaporated to yield 5.12 g of a dark oil. Purification by automated flash chromatography gave ethyl 2-butyl-5-methoxypyrazolo[1,5-a]pyridine-3-carboxylate as an orange solid (410 mg, 33%). LCMS (General 3) RT: 1.39 min; Yield: 97.5%; m/z 277.3 (M+H$^+$). $^1$H NMR (300 MHz, Chloroform-d) δ 8.22 (dd, J=7.5, 0.7 Hz, 1H), 7.41 (d, J=2.8 Hz, 1H), 6.54 (dd, J=7.5, 2.8 Hz, 1H), 4.37 (q, J=7.1 Hz, 2H), 3.91 (s, 3H), 3.07-2.97 (m, 2H), 1.82-1.67 (m, 2H), 1.42 (td, J=7.4, 3.8 Hz, 5H), 0.96 (t, J=7.3 Hz, 3H).

Step 3. 2-butyl-5-methoxypyrazolo[1,5-a]pyridine was prepared according to the following procedure. Over solid ethyl 2-butyl-5-methoxypyrazolo[1,5-a]pyridine-3-carboxylate (410 mg, 1 Eq, 1.48 mmol), Water (3.0 mL), 95% H$_2$SO$_4$ (1.7 mL, 20 eq, 29.7 mmol) and 1,4-Dioxane (6.0 mL) were sequentially added. The warm mixture was further heated at 100° C. for 40 h. After cooling to room temperature, the mixture was diluted with water (33 mL) and carefully basified with solid sodium carbonate (3.46 g, 22 Eq, 32.6 mmol). The resulting mixture was extracted with AcOEt (3×45 mL), dried on Na$_2$SO$_4$ and evaporated to dryness. Purification by automated flash chromatography yielded 2-butyl-5-methoxypyrazolo[1,5-a]pyridine as an orange oil (161 mg, 53%). LCMS (General 3) RT: 1.18 min; Yield: 99.6%; m/z 205.2 (M+H$^+$). $^1$HNMR (300 MHz, Chloroform-d) δ 8.17 (dt, J=7.5, 0.8 Hz, 1H), 6.63 (dd, J=2.7, 0.7 Hz, 1H), 6.34 (dd, J=7.6, 2.7 Hz, 1H), 6.10 (d, J=0.8 Hz, 1H), 3.82 (s, 3H), 2.82-2.70 (m, 2H), 1.79-1.63 (m, 2H), 1.49-1.33 (m, 2H), 0.95 (t, J=7.3 Hz, 3H).

Step 4. 2-butylpyrazolo[1,5-a]pyridin-5-ol was prepared according to General Experimental Procedure A. 2-butyl-5-methoxypyrazolo[1,5-a]pyridine (161 mg, 0.79 mmol) gave 2-butylpyrazolo[1,5-a]pyridin-5-ol as a brown solid (144 mg, 89%). LCMS (General 3) RT: 0.89 min; Yield: 95.6%; m/z 191.4, m/z 189.3 (M−H)$^-$. $^1$H NMR (300 MHz, Chloroform-d) δ 9.50 (s, 1H), 8.14 (dt, J=7.5, 0.8 Hz, 1H), 6.72 (dd, J=2.6, 0.7 Hz, 1H), 6.36 (dd, J=7.5, 2.6 Hz, 1H), 6.04 (d, J=0.8 Hz, 1H), 2.81-2.71 (m, 2H), 1.78-1.63 (m, 2H), 1.48-1.31 (m, 2H), 0.91 (t, J=7.3 Hz, 3H).

Step 5. tert-butyl (E)-(2-(((2-butylpyrazolo[1,5-a]pyridin-5-yl)oxy)methyl)-3-fluoroallyl)carbamate was prepared according to General Experimental Procedure B. The procedure afforded tert-butyl (E)-(2-(((2-butylpyrazolo[1,5-a]pyridin-5-yl)oxy)methyl)-3-fluoroallyl)carbamateas a pale yellow wax (28 mg, 24%). LCMS (General 3) RT: 1.36 min; Yield: 96.7%; m/z 378.4, m/z 376.5 (M−h)$^-$). $^1$HNMR (300 MHz, Chloroform-d) δ 8.18 (dt, J=7.6, 0.8 Hz, 1H), 6.76 (dt, J=81.9, 1.1 Hz, 1H), 6.65 (d, J=2.7 Hz, 1H), 6.34 (dd, J=7.5, 2.7 Hz, 1H), 6.10 (d, J=0.8 Hz, 1H), 4.76 (s, 1H), 4.47-4.40 (m, 2H), 4.00 (dd, J=6.6, 2.3 Hz, 2H), 2.82-2.70 (m, 2H), 1.79-1.64 (m, 2H), 1.49-1.36 (m, 2H), 1.41 (s, 9H), 0.94 (t, J=7.3 Hz, 3H). $^{19}$F NMR (282 MHz, Chloroform-d) δ-128.06 (d, J=81.9 Hz).

Step 6. (E)-2-(((2-butylpyrazolo[1,5-a]pyridin-5-yl)oxy)methyl)-3-fluoroprop-2-en-1-amine bis(4-methylbenzenesulfonate) was prepared according to General Experimental Procedure C. tert-butyl (E)-(2-(((2-butylpyrazolo[1,5-a]pyridin-5-yl)oxy)methyl)-3-fluoroallyl)carbamate (28 mg, 0.074 mmol) gave (E)-2-(((2-butylpyrazolo[1,5-a]pyridin-5-yl)oxy)methyl)-3-fluoroprop-2-en-1-amine bis(4-methylbenzenesulfonate) as a white solid (29 mg, 63%). LCMS (28817C TFA LCMS-5 C-3.M) RT: 1.67 min; Yield: 94.9%; m/z 278.2 (M+H$^+$). $^1$H NMR (300 MHz, DMSO-d$_6$) δ 8.45 (d, J=7.5 Hz, 1H), 8.00 (s, 3H), 7.51-7.46 (m, 4H), 7.38 (d, J=81.8 Hz, 1H), 7.13 (d, J=7.9 Hz, 4H), 6.99 (d, J=2.7 Hz, 1H), 6.52 (dd, J=7.5, 2.7 Hz, 1H), 6.22 (s, 1H), 4.63 (d, J=3.6 Hz, 2H), 3.73-3.61 (m, 2H), 2.69 (t, J=7.6 Hz, 2H), 2.30 (s, 6H), 1.66 (p, J=7.7 Hz, 2H), 1.36 (h, J=7.3 Hz, 2H), 0.92 (t, J=7.3 Hz, 3H). $^{19}$F NMR (282 MHz, DMSO-d$_6$) δ-121.98 (d, J=81.4 Hz).

Example 9

(Z)-2-(((2-cyclopentylimidazo[1,2-a]pyridin-6-yl)oxy)methyl)-3-fluoroprop-2-en-1-amine 4-methylbenzenesulfonate

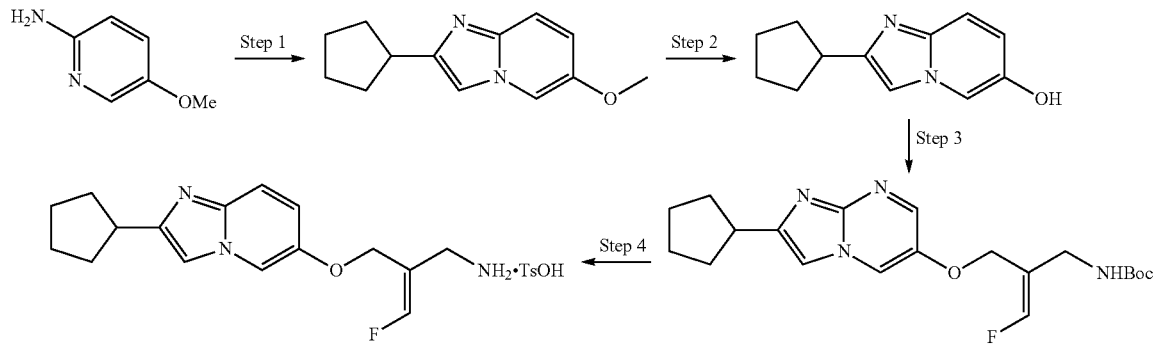

Step 1. 2-cyclopentyl-6-methoxyimidazo[1,2-a]pyridine was prepared according to General Experimental Procedure D. using 2-bromo-1-cyclopentylethan-1-one. LCMS (General 3) RT: 0.90 min; Yield: 85%; m/z 217.4 (M+H$^+$).

Step 2. 2-cyclopentylimidazo[1,2-a]pyridin-6-ol was prepared according to General Experimental Procedure A. 2-cyclopentyl-6-methoxyimidazo[1,2-a]pyridine (725 mg, 3.35 mmol) gave 2-cyclopentylimidazo[1,2-a]pyridin-6-ol (315 mg, 47%) as a brown solid. LCMS (General 3) RT: 0.60 min; Yield: 77%; m/z 203.4 (M+H$^+$).

Step 3. tert-butyl (Z)-(2-(((2-cyclopentylimidazo[1,2-a]pyridin-6-yl)oxy)methyl)-3-fluoroallyl)carbamate was prepared according to General Experimental Procedure B. 2-cyclopentylimidazo[1,2-a]pyridin-6-ol (190 mg, 0.94 mmol) gave tert-butyl (Z)-(2-(((2-cyclopentylimidazo[1,2-a]pyridin-6-yl)oxy)methyl)-3-fluoroallyl)carbamate (94 mg, 26%) as a brown oil. LCMS (General 3) RT: 1.16 min; Yield: 83%; m/z 390.3 (M+H$^+$).

Step 4. (Z)-2-(((2-cyclopentylimidazo[1,2-a]pyridin-6-yl)oxy)methyl)-3-fluoroprop-2-en-1-amine 4-methylbenzenesulfonate was prepared according to General Experimental Procedure C. tert-butyl (Z)-(2-(((2-cyclopentylimidazo[1,2-a]pyridin-6-yl)oxy)methyl)-3-fluoroallyl)carbamate (94 mg, 0.24 mmol) gave (Z)-2-(((2-cyclopentylimidazo[1,2-a]pyridin-6-yl)oxy)methyl)-3-fluoroprop-2-en-1-amine 4-methylbenzenesulfonate (38 mg, 34%) as a beige solid. LCMS: (28817C TFA LCMS-5 C-3.M) RT: 1.357 min; Yield: 93%; m/z 290.1 (M+H$^+$). NMR: $^1$H NMR (300 MHz, DMSO-d$_6$) δ 8.40 (d, J=2.3 Hz, 1H), 8.05 (s, 3H), 7.79 (s, 1H), 7.58 (d, J=9.7 Hz, 1H), 7.46 (d, J=8.1 Hz, 2H), 7.42-7.25 (m, 1H), 7.09 (d, J=8.0 Hz, 3H), 4.72 (d, J=2.7 Hz, 2H), 3.57 (d, J=3.0 Hz, 2H), 3.24-3.08 (m, 1H), 2.27 (s, 3H), 2.12-1.89 (m, 2H), 1.85-1.52 (m, 6H).

Example 10 tert-butyl (E)-(2-(((2-butylimidazo[1,2-a]pyrimidin-6-yl)oxy)methyl)-3-fluoroallyl)carbamate

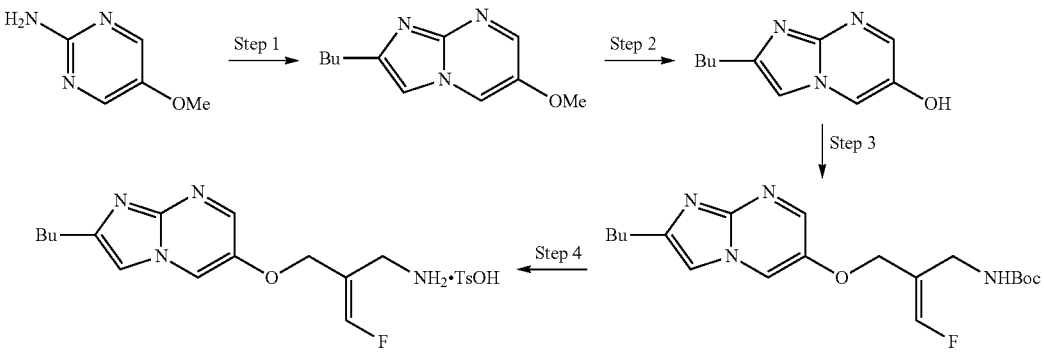

Step 1. 2-butyl-6-methoxyimidazo[1,2-a]pyrimidine was prepared according to General Experimental Procedure 16. 5-methoxypyrimidin-2-amine (594 mg, 4.75 mmol) gave 2-butyl-6-methoxyimidazo[1,2-a]pyrimidine (178 mg, 16%) as a yellow solid. LCMS (General 3): RT: 0.71 min, Yield: 90%, m/z 206.4 (M+H$^+$).

Step 2. 2-butylimidazo[1,2-a]pyrimidin-6-ol was prepared according to General Experimental Procedure 2. 2-butyl-6-methoxyimidazo[1,2-a]pyrimidine (178 mg, 0.867 mmol) gave tert-butyl (E)-(2-(((2-butylimidazo[1,2-a]pyrimidin-6-yl)oxy)methyl)-3-fluoroallyl)carbamate (105 mg, 61%) as a light brown solid. LCMS (General 3): RT: 0.52 min, Yield: 97%, m/z 192.4 (M+H$^+$).

Step 3. tert-butyl (E)-(2-(((2-butylimidazo[1,2-a]pyrimidin-6-yl)oxy)methyl)-3-fluoroallyl)carbamate was prepared according to General Experimental Procedure 3. tert-butyl (E)-(2-(((2-butylimidazo[1,2-a]pyrimidin-6-yl)oxy) methyl)-3-fluoroallyl)carbamate (105 mg, 0.55 mmol) gave tert-butyl (E)-(2-(((2-butylimidazo[1,2-a]pyrimidin-6-yl) oxy)methyl)-3-fluoroallyl)carbamate (30 mg, 15%) as a brown solid. LCMS (General 3): RT: 1.03 min, Yield: 99%, m/z 379.3 (M+H$^+$).

Step 3. (E)-2-(((2-butylimidazo[1,2-a]pyrimidin-6-yl) oxy)methyl)-3-fluoroprop-2-en-1-amine 4-methylbenzenesulfonate was prepared according to General Experimental Procedure 5. tert-butyl (E)-(2-(((2-butylimidazo[1,2-a]pyrimidin-6-yl)oxy)methyl)-3-fluoroallyl)carbamate (30 mg, 0.79 mmol) gave (E)-2-(((2-butylimidazo[1,2-a]pyrimidin-6-yl)oxy)methyl)-3-fluoroprop-2-en-1-amine 4-methylbenzenesulfonate (28 mg, 79%) as a brown solid. LCMS (28817C TFA LCMS-5 C-3.M) RT: 1.224 min; Yield: 98.52%; m/z 279.20 (M+H$^+$). $^1$H NMR (299 MHz, Methanol-d4) δ 8.61 (d, J=2.9 Hz, 1H), 8.47 (d, J=2.9 Hz, 1H), 7.72-7.66 (m, 2H), 7.59 (s, 1H), 7.27 (d, J=80.6 Hz, 1H), 7.25-7.19 (m, 2H), 4.68 (dd, J=3.5, 1.0 Hz, 2H), 3.91-3.83 (m, 2H), 2.79 (t, J=7.6 Hz, 2H), 2.35 (s, 3H).

Example 11

Biological Samples and Assays

The following general materials and methods were used, where indicated, or may be used in the Examples. Standard methods in molecular biology are described in the scientific literature (see, e.g., Sambrook and Russell (2001) Molecular Cloning, 3$^{rd}$ ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

VAP-1 Assay

The capability of compounds described herein to inhibit the enzymatic activity of vascular adhesion protein-1 (VAP-1) was determined by fluorometric assay. The assay procedure provided by R&D Systems was modified slightly for use as an inhibitor screening assay. The assay measured the H$_2$O$_2$ generated from the oxidative deamination of benzylamine by rhVAP-1 by converting Amplex® Red to the fluorescent product, resorufin, via horseradish peroxidase (HRP) and H$_2$O$_2$. Reaction buffer was 10 mM NaHCO$_3$, pH 7.4. A standard curve was prepared by serially diluting H$_2$O$_2$ in reaction buffer. A 10 μM solution of resorufin was prepared in reaction buffer and was dispensed to 2 wells. These wells served as positive control for maximum fluorescence. Reaction buffer was added to the individual wells so that the final volume in each well was 100 μL. Amplex Red was diluted to 1 mM in reaction buffer. A 10U stock of HRP was prepared in reaction buffer. A reaction cocktail was prepared by mixing equal parts 1 mM Amplex Red with 10U HRP with 3 parts reaction buffers. The reaction cocktail was added to the appropriate wells, so that that final concentration in the well was 0.05 mM Amplex Red and 0.5U HRP. A 200 μM solution of benzylamine was prepared in reaction buffer. Benzylamine was added to the appropriate wells so that the final concentration was 50 μM. Inhibitors were diluted in DMSO to 20× and distributed to the appropriate wells. UP-1207 served a positive control. rhVAP-1 was purchased from R&D Systems. The concentration used for each lot was determined so that the activity was equal to the first lot. Two wells were left blank as controls. The plate was incubated for 30 minutes at 37° C., protected from light under foil. The plate was read at 530/35 emission and 590/35 excitation. Data processing was performed using Excel and Prism software.

MAO Assay

The capability of compounds described herein to inhibit MAO was determined using a modified Promega MAO-Glo™ assay kit. The substrate ((4S)-4,5-dihydro-2-(6-hydroxybenzothiazolyl)-4-thiazolecarboxylic acid) was converted by MAO to produce methyl ester luciferin. The luciferin was then converted by luciferase to produce oxyluciferin and light. The light was measured using a luminescence setting on the plate reader. A standard curve was prepared by serially diluting luciferin in reaction buffer. The standard kit reaction buffer was used—100 mM HEPES (pH 7.5), 5% glycerol. The substrate was dispensed into the wells so that the final concentration for MAO-A inhibition assay would be 10 μM and MAO-B inhibition assay would be 1 μM. Inhibitors were diluted in DMSO to 4× and distributed to the appropriate wells. Clorgyline and Deprenyl served as positive controls. rhMAO-A and rhMAO-B were purchased from Sigma. MAO-A or MAO-B was added to the appropriate wells. The plate was incubated for 1 hour, at room temperature with gentle shaking (90 rpm). The detection agent was added at equal volume (48 μL detection agent to 48 μL reaction). The plate was incubated for 20 minutes, at room temperature with gentle shaking (90 rpm). The plate luminescence was read. Data processing was performed using Prism software.

The capability of compounds described herein to inhibit MAO was determined using a modified Promega MAO-Glo™ assay. Test compounds, substrate and enzyme were incubated per manufacturer instructions for 1hour, at room temperature with gentle shaking (90 rpm) before addition of detection agent. The detection agent was added at equal volume (48 μL detection agent to 48 μL reaction). The plate was incubated for 20 minutes, at room temperature with gentle shaking (90 rpm). The plate luminescence was read. Data processing was performed using Prism software.

The capability of compounds described herein to inhibit the enzymatic activity of vascular adhesion protein-1 (VAP-1) was determined by fluorometric assay. The assay procedure provided by R&D Systems was modified slightly for use as an inhibitor screening assay. The assay measured the H$_2$O$_2$ generated from the oxidative deamination of benzylamine by rhVAP-1 by converting Amplex® Red to the fluorescent product, resorufin, via horseradish peroxidase (HRP) and H$_2$O$_2$. Amplex Red, HRP, Benzylamine, inhibitors (with DMSO as vehicle, 0.5% v/v) and rhVAP-1 were added to the wells. Assay was conducted in 10 mM NaHCO$_3$, pH 7.4. A standard curve was prepared by serially diluting H$_2$O$_2$ in reaction buffer. The plate was incubated for 30 minutes at 37° C., protected from light under foil. The plate was read at 530/35 emission and 590/35 excitation. Data processing was performed using Prism software.

Using the assays described herein, the activity for several compounds of the disclosure was determined. The potency levels are set forth in Table 1.

TABLE 1

| EX. | STRUCTURE | NAME | VAP-1 IC$_{50}$ (nM) | MAO A IC$_{50}$ (nM) | MAO B IC$_{50}$ (nM) |
|---|---|---|---|---|---|
| 1 | 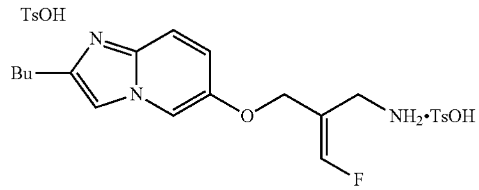 | (E)-2-(((2-butylimidazo[1,2-a]pyridin-6-yl)oxy)methyl)-3-fluoroprop-2-en-1-amine bis(4-methylbenzenesulfonate) | A | D | C |
| 2 | 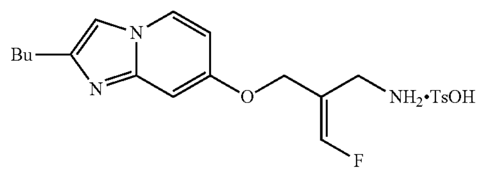 | (E)-2-(((2-butylimidazo[1,2-a]pyridin-7-yl)oxy)methyl)-3-fluoroprop-2-en-1-amine 4-methylbenzenesulfonate | A | D | D |
| 3 | 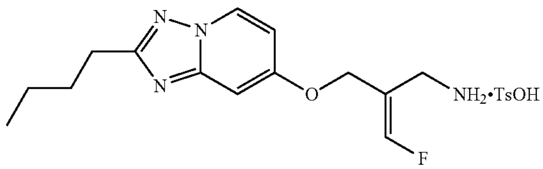 | (E)-2-(((2-butyl-[1,2,4]triazolo[1,5-a]pyridin-7-yl)oxy)methyl)-3-fluoroprop-2-en-1-amine 4-methylbenzenesulfonate | A | D | C |
| 4 | 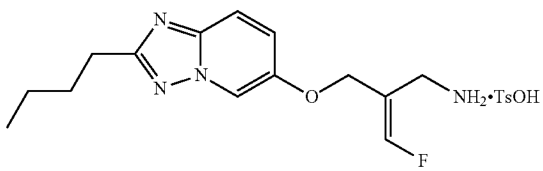 | (E)-2-(((2-butyl-[1,2,4]triazolo[1,5-a]pyridin-6-yl)oxy)methyl)-3-fluoroprop-2-en-1-amine 4-methylbenzenesulfonate | A | D | B |
| 5 | 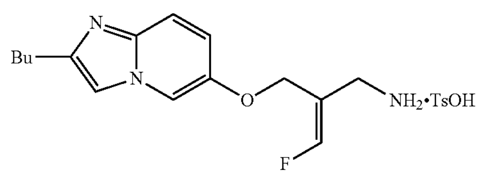 | (Z)-2-(((2-butylimidazo[1,2-a]pyridin-6-yl)oxy)methyl)-3-fluoroprop-2-en-1-amine 4-methylbenzenesulfonate | A | D | C |
| 6 | 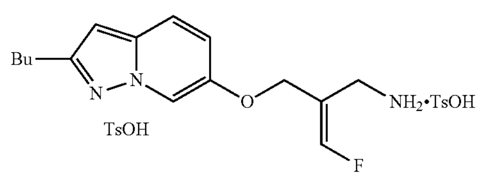 | ((E)-2-(((2-butylpyrazolo[1,5-a]pyridin-6-yl)oxy)methyl)-3-fluoroprop-2-en-1-amine bis(4-methylbenzenesulfonate) | A | D | B |
| 7 | 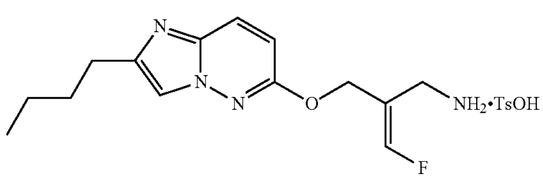 | (E)-2-(((2-butylimidazo[1,2-b]pyridazin-6-yl)oxy)methyl)-3-fluoroprop-2-en-1-amine 4-methylbenzenesulfonate | A | >50 μM | B |
| 8 | 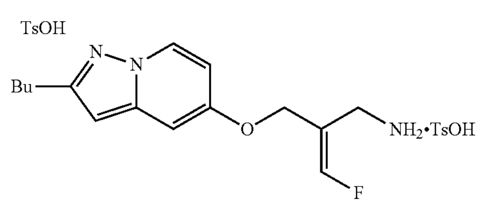 | (E)-2-(((2-butylpyrazolo[1,5-a]pyridin-5-yl)oxy)methyl)-3-fluoroprop-2-en-1-amine bis(4-methylbenzenesulfonate) | A | C | B |

TABLE 1-continued

| EX. | STRUCTURE | NAME | VAP-1 IC$_{50}$ (nM) | MAO A IC$_{50}$ (nM) | MAO B IC$_{50}$ (nM) |
|---|---|---|---|---|---|
| 9 | 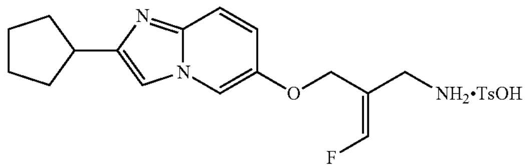 | (Z)-2-(((2-cyclopentylimidazo[1,2-a]pyridin-6-yl)oxy)methyl)-3-fluoroprop-2-en-1-amine 4-methylbenzenesulfonate | A | C | C |
| 10 | 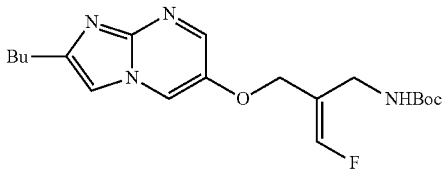 | tert-butyl (E)-(2-(((2-butylimidazo[1,2-a]pyrimidin-6-yl)oxy)methyl)-3-fluoroallyl)carbamate | A | >50 μM | C |

Biochemical assay IC$_{50}$ data are designated within the following ranges:

A: ≤0.10 μM
B: >0.10 μM to ≤1.0 μM
C: >1.0 μM to ≤10 μM
D: >10 μM to 30 μM

Although the disclosure has been described with reference to the above examples, it will be understood that modifications and variations are encompassed within the spirit and scope of the disclosure. Accordingly, the disclosure is limited only by the following claims.

What is claimed is:
1. A compound having structural Formula (IV):

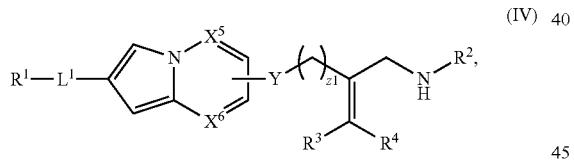

(IV)

or an alkene isomer, tautomer, or an isotopic variant thereof; or a pharmaceutically acceptable salt, solvate, or hydrate thereof;
wherein:
X$^1$ and X$^4$ are independently =N or =CH—;
X$^5$ is =N or —CR$^5$—;
X$^6$ is =N or —CR$^6$—;
Y is —O—;
z1 is 1;
n1, n5, n6, and n7 are independently an integer from 0 to 4;
m5, m6, v1, v2, v5, and v6 are independently 1 or 2;
L$^1$ is a bond, —O—, —S—, —NR$^{1L}$—, substituted or unsubstituted alkylene, substituted or unsubstituted heteroalkylene, substituted or unsubstituted cycloalkylene, or substituted or unsubstituted heterocycloalkylene, substituted or unsubstituted arylene, or substituted or unsubstituted heteroarylene;
R$^{1L}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^1$ is independently hydrogen, halogen, —CX$^{1.1}_3$, —CHX$^{1.1}_2$, —CH$_2$X$^{1.1}$, —CN, —SO$_{n1}$R$^{1A}$, —SO$_{v1}$NR$^{1B}$R$^{1C}$, —NHNR$^{1B}$R$^{1C}$, —ONR$^{1B}$R$^{1C}$, —NHC(O)NHNR$^{1B}$R$^{1C}$, —NHC(O)NR$^{1B}$R$^{1C}$, —N(O)$_{m1}$, —NR$^{1B}$R$^{1C}$, —C(O)R$^{1D}$, —C(C)OR$^{1D}$, —C(O)NR$^{1B}$R$^{1C}$, —OR$^{1A}$, —NR$^{1B}$SO$_2$R$^{1A}$, —NR$^{1B}$C(O)R$^{1D}$, —NR$^{1B}$C(O)OR$^{1D}$, —NR$^{1B}$OR$^{1D}$, —OCX$^{1.1}_3$, —OCHX$^{1.1}_2$, R$^{12}$-substituted or unsubstituted alkyl, R$^{12}$-substituted or unsubstituted heteroalkyl, R$^{12}$-substituted or unsubstituted cycloalkyl, R$^{12}$-substituted or unsubstituted heterocycloalkyl, R$^{12}$-substituted or unsubstituted aryl, or R$^{12}$-substituted or unsubstituted heteroaryl, or at least one amino acid;
R$^2$ is hydrogen
R$^3$ and R$^4$ are independently hydrogen or —F;
R$^5$ is hydrogen, halogen, —CX$^{5.1}_3$, —CHX$^{5.1}_2$, —CH$_2$X$^{5.1}$, —CN, —N$_3$, —SO$_{n5}$R$^{5A}$, —SO$_{v5}$NR$^{5B}$R$^{5C}$, —NHNR$^{5B}$R$^{5C}$, —ONR$^{5B}$R$^{5C}$, —NHC(O)NHNR$^{5B}$R$^{5C}$, —NHC(O)NR$^{5B}$R$^{5C}$, —N(O)$_{m5}$, —NR$^{5B}$R$^{5C}$, —C(O)R$^{5D}$, —C(O)OR$^{5D}$, —C(O)NR$^{5B}$R$^{5C}$, —OR$^{5A}$, —NR$^{5B}$SO$_2$R$^{5A}$, —NR$^{5B}$C(O)R$^{5D}$, —NR$^{5B}$C(O)OR$^{5D}$, —NR$^{5B}$OR$^{5D}$, —OCX$^{5.1}_3$, —OCHX$^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^6$ is hydrogen, halogen, —CX$^{6.1}_3$, —CHX$^{6.1}_2$, —CH$_2$X$^{6.1}$, —CN, —N$_3$, —SO$_{n6}$R$^{6A}$, —SO$_{v6}$NR$^{6B}$R$^{6C}$, —NHNR$^{6B}$R$^{6C}$, —ONR$^{6B}$R$^{6C}$, —NHC(O)NHNR$^{6B}$R$^{6C}$, —NHC(O)NR$^{6B}$R$^{6C}$, —N(O)$_{m6}$, —NR$^{6B}$R$^{6C}$, —C(O)R$^{6D}$, —C(O)—OR$^{6D}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}_3$, —OCHX$^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^{12}$ is hydrogen, halogen, —CX$^{12.1}_3$, —CHX$^{12.1}_2$, —CH$_2$X$^{12.1}$, —CN, —NR$^{12B}$R$^{12C}$, —C(O)R$^{12D}$, —C(O)OR$^{12D}$, —C(O)NR$^{12B}$R$^{12C}$, —OR$^{12A}$, —OCX$^{12.1}_3$, —OCHX$^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$ is hydrogen, halogen, —$CF_3$, —$CCl_3$, —$CBr_3$, —$CI_3$, —COOH, —$CONH_2$, $R^{12A}$-substituted or unsubstituted alkyl, $R^{12A}$-substituted or unsubstituted heteroalkyl, $R^{12A}$-substituted or unsubstituted cycloalkyl, $R^{12A}$-substituted or unsubstituted heterocycloalkyl, $R^{12A}$-substituted or unsubstituted aryl, or $R^{12A}$-substituted or unsubstituted heteroaryl;

$R^{1B}$ is hydrogen, halogen, —$CF_3$, —$CCl_3$, —$CBr_3$, —$CI_3$, —COOH, —$CONH_2$, $R^{12B}$-substituted or unsubstituted alkyl, $R^{12B}$-substituted or unsubstituted heteroalkyl, $R^{12B}$-substituted or unsubstituted cycloalkyl, $R^{12B}$-substituted or unsubstituted heterocycloalkyl, $R^{12B}$-substituted or unsubstituted aryl, or $R^{12B}$-substituted or unsubstituted heteroaryl;

$R^{1C}$ is hydrogen, halogen, —$CF_3$, —$CCl_3$, —$CBr_3$, —$CI_3$, —COOH, —$CONH_2$, $R^{12C}$-substituted or unsubstituted alkyl, $R^{12C}$-substituted or unsubstituted heteroalkyl, $R^{12C}$-substituted or unsubstituted cycloalkyl, $R^{12C}$-substituted or unsubstituted heterocycloalkyl, $R^{12C}$-substituted or unsubstituted aryl, or $R^{12C}$-substituted or unsubstituted heteroaryl; or $R^{1B}$ and $R^{1C}$ substituents bonded to the same nitrogen atom may optionally be joined to form a substituted or unsubstituted heterocycloalkyl or substituted or unsubstituted heteroaryl;

$R^{1D}$ is hydrogen, halogen, —$CF_3$, —$CCl_3$, —$CBr_3$, —$CI_3$, —COOH, —$CONH_2$, $R^{12D}$-substituted or unsubstituted alkyl, $R^{12D}$-substituted or unsubstituted heteroalkyl, $R^{12D}$-substituted or unsubstituted cycloalkyl, $R^{12D}$-substituted or unsubstituted heterocycloalkyl, $R^{12D}$-substituted or unsubstituted aryl, or $R^{12D}$-substituted or unsubstituted heteroaryl;

$R^{5A}$, $R^{5B}$, $R^{5C}$, $R^{5D}$, $R^{6A}$, $R^{6B}$, $R^{6C}$, $R^{6D}$, $R^{12A}$, $R^{12B}$, $R^{12C}$, and $R^{12D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{5B}$ and $R^{5C}$; $R^{6B}$ and $R^{6C}$; $R^{12B}$ and $R^{12C}$ substituents bonded to the same nitrogen atom may optionally be joined to form a substituted or unsubstituted heterocycloalkyl or substituted or unsubstituted heteroaryl; and $X^{1.1}$, $X^{5.1}$, $X^{6.1}$, and $X^{12.1}$ are independently —Cl, —Br, —I, or —F.

2. The compound of claim 1, wherein the compound has structural Formula (V-A):

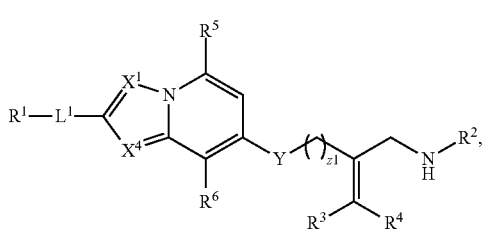

(V-A)

or an alkene isomer, tautomer, or an isotopic variant thereof; or a pharmaceutically acceptable salt, solvate, or hydrate thereof.

3. The compound of claim 1, wherein the compound has structural Formula (V-B):

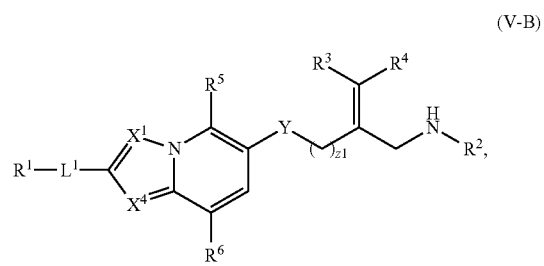

(V-B)

or an alkene isomer, tautomer, or an isotopic variant thereof; or a pharmaceutically acceptable salt, solvate, or hydrate thereof.

4. The compound of claim 1, wherein the compound has structural Formula (VI-A):

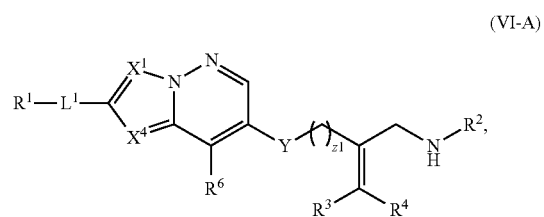

(VI-A)

or an alkene isomer, tautomer, or an isotopic variant thereof; or a pharmaceutically acceptable salt, solvate, or hydrate thereof.

5. The compound of claim 1, wherein the compound has structural Formula (VI-B):

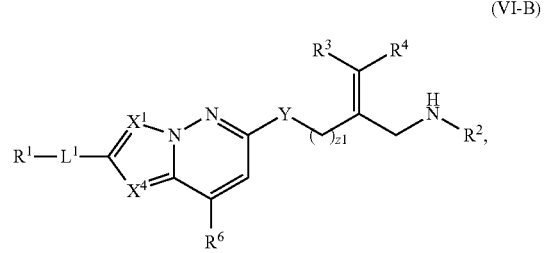

(VI-B)

or an alkene isomer, tautomer, or an isotopic variant thereof; or a pharmaceutically acceptable salt, solvate, or hydrate thereof, wherein X1 is =CH and X4 is =N—.

6. The compound of claim 1, wherein the compound has structural Formula (VII-A):

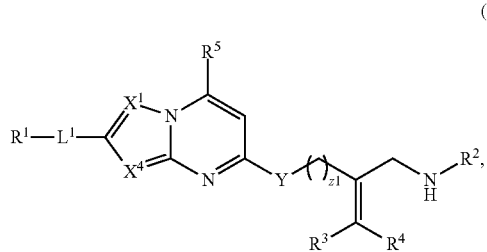

(VII-A)

or an alkene isomer, tautomer, or an isotopic variant thereof; or a pharmaceutically acceptable salt, solvate, or hydrate thereof.

7. The compound of claim 1, wherein the compound has structural Formula (VII-B):

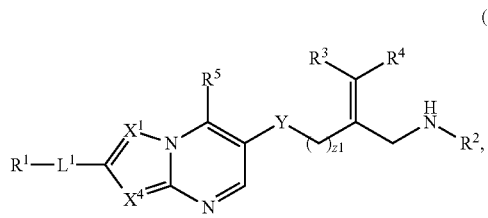

(VII-B)

or an alkene isomer, tautomer, or an isotopic variant thereof; or a pharmaceutically acceptable salt, solvate, or hydrate thereof.

8. The compound of claim 1, or an alkene isomer, tautomer, or an isotopic variant thereof; or a pharmaceutically acceptable salt, solvate, or hydrate thereof, wherein $R^5$ and $R^6$ are independently hydrogen, —F, —Br, or —CH$_3$.

9. The compound of claim 1, or an alkene isomer, tautomer, or an isotopic variant thereof; or a pharmaceutically acceptable salt, solvate, or hydrate thereof, comprising a mixture of compounds having:
$R^3$ is —F and $R^4$ is hydrogen; and
$R^3$ is hydrogen and $R^4$ is —F.

10. The compound of claim 1, or an alkene isomer, tautomer, or an isotopic variant thereof; or a pharmaceutically acceptable salt, solvate, or hydrate thereof, comprising a mixture of (E)- and (Z)-alkene isomers.

11. The compound of claim 1, or an alkene isomer, tautomer, or an isotopic variant thereof; or a pharmaceutically acceptable salt, solvate, or hydrate, or prodrug thereof, wherein $R^2$ is hydrogen.

12. The compound of claim 1, or an alkene isomer, tautomer, or an isotopic variant thereof; or a pharmaceutically acceptable salt, solvate, or hydrate thereof, wherein $L^1$ is a bond, —NR$^{1L}$—, substituted or unsubstituted alkylene, substituted or unsubstituted heteroalkylene, substituted or unsubstituted cycloalkylene, or substituted or unsubstituted heterocycloalkylene.

13. The compound of claim 1, or an alkene isomer, tautomer, or an isotopic variant thereof; or a pharmaceutically acceptable salt, solvate, or hydrate thereof, wherein $R^1$ is —NR$^{1B}$R$^{1C}$, C(O)NR$^{1B}$R$^{1C}$, OR$^{1A}$, R$^{12}$-substituted or unsubstituted alkyl, R$^{12}$-substituted or unsubstituted heteroalkyl, R$^{12}$-substituted or unsubstituted cycloalkyl, R$^{12}$-substituted or unsubstituted heterocycloalkyl, R$^{12}$-substituted or unsubstituted aryl, or R$^{12}$-substituted or unsubstituted heteroaryl.

14. The compound of claim 1, or an alkene isomer, tautomer, or an isotopic variant thereof; or a pharmaceutically acceptable salt, solvate, or hydrate thereof, wherein $R^1$ is R$^{12}$-substituted or unsubstituted C$_1$-C$_6$ alkyl or R$^{12}$-substituted or unsubstituted cycloalkyl.

15. A compound, wherein the compound is:

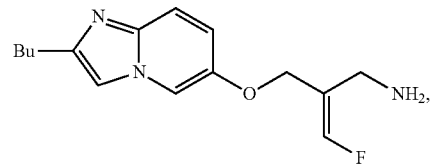

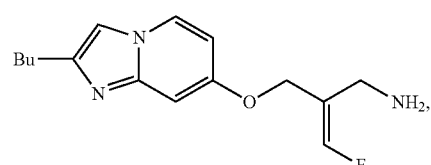

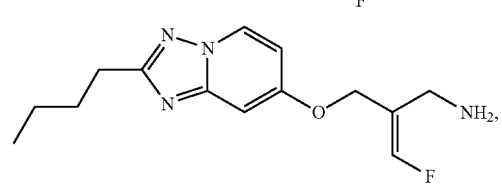

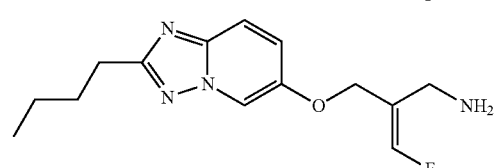

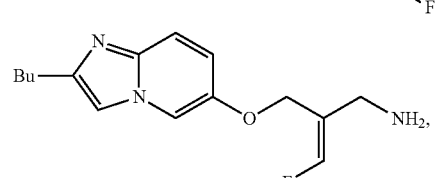

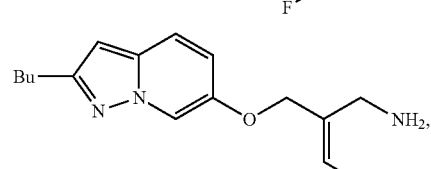

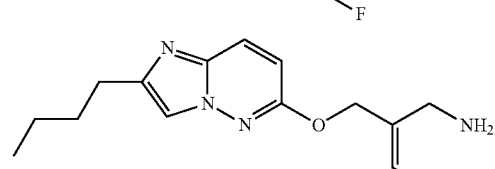

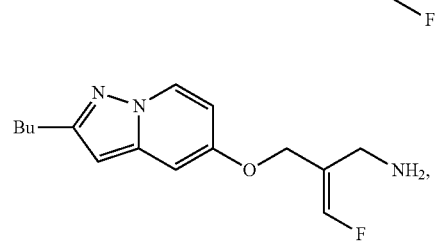

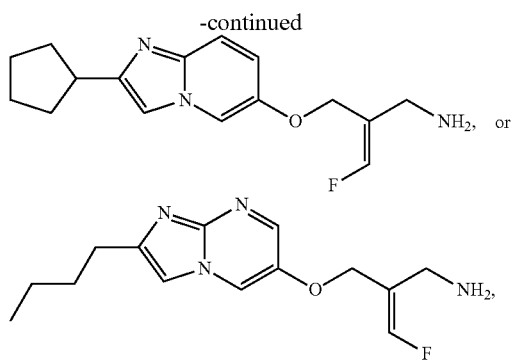

or an alkene isomer, tautomer, or an isotopic variant thereof; or a pharmaceutically acceptable salt, solvate, or hydrate thereof.

16. A pharmaceutical composition, comprising the compound claim 1, or an alkene isomer, tautomer, or an isotopic variant thereof; or a pharmaceutically acceptable salt, solvate, or hydrate thereof, and at least one pharmaceutically acceptable excipient.

17. A method of inhibiting vascular adhesion protein (VAP-1), comprising contacting VAP-1 with the compound of claim 1, or an alkene isomer, tautomer, or an isotopic variant thereof; or a pharmaceutically acceptable salt, solvate, or hydrate thereof.

18. A method of treating an ophthalmic disease or disorder in a subject in need thereof, comprising administering to the subject a therapeutically effective amount of the compound of claim 1, or an alkene isomer, tautomer, or an isotopic variant thereof; or a pharmaceutically acceptable salt, solvate, or hydrate thereof.

* * * * *